US008700176B2

(12) United States Patent
Azar et al.

(10) Patent No.: US 8,700,176 B2
(45) Date of Patent: Apr. 15, 2014

(54) APPARATUS AND METHOD FOR NON-INVASIVE TREATMENT OF SKIN TISSUE

(75) Inventors: Zion Azar, Shoham (IL); Pinchas Shalev, Herzlia (IL)

(73) Assignee: Pollogen Ltd., Tel-Aviv (IL)

( * ) Notice: Subject to any disclaimer, the term of this patent is extended or adjusted under 35 U.S.C. 154(b) by 1767 days.

(21) Appl. No.: 11/828,371

(22) Filed: Jul. 26, 2007

(65) Prior Publication Data
US 2008/0183251 A1 Jul. 31, 2008

Related U.S. Application Data

(60) Provisional application No. 60/833,474, filed on Jul. 27, 2006.

(51) Int. Cl.
*A61N 5/01* (2006.01)

(52) U.S. Cl.
USPC .......................................................... 607/101

(58) Field of Classification Search
USPC ........ 607/98, 99, 101, 102, 154–156; 606/27, 606/28, 32–35
See application file for complete search history.

(56) References Cited

U.S. PATENT DOCUMENTS

| 558,465 | A | 4/1896 | Bell |
|---|---|---|---|
| 589,445 | A | 9/1897 | Seide |
| 2,727,132 | A | 12/1955 | Hills |
| 3,093,724 | A | 6/1963 | Johnson |
| 3,474,224 | A | 10/1969 | Carter |
| 3,934,115 | A | 1/1976 | Peterson |
| 4,514,088 | A | 4/1985 | Coccoli |
| 4,631,400 | A | 12/1986 | Tanner et al. |
| 4,920,260 | A | 4/1990 | Victor et al. |
| 5,059,192 | A | 10/1991 | Zaias |
| 5,064,993 | A | 11/1991 | Hashimoto |
| 5,143,063 | A | 9/1992 | Fellner |

(Continued)

FOREIGN PATENT DOCUMENTS

| JP | 7-500025 T | 1/1995 |
|---|---|---|
| JP | 2002-5379391 T | 11/2002 |

(Continued)

OTHER PUBLICATIONS

English Translation of Office Action of Japanese Application No. 2009-521417 mailed on Jun. 26, 2012.

(Continued)

*Primary Examiner* — Cris L Rodriguez
*Assistant Examiner* — Matthew Seward
(74) *Attorney, Agent, or Firm* — Pearl Cohen Zedek Latzer Baratz LLP

(57) ABSTRACT

Skin treating devices and systems for delivering RF electromagnetic energy to the skin. The devices include one or more electromagnetic RF generating units, multiple RF electrode groups and a controller for controllably applying RF energy to the skin through any selected RF electrode group or any selected RF electrode group combination selected from the multiple groups. The electrodes may be stationary and/or movable electrodes. Different RF frequencies and/or frequency bands may be used. The alternation of energy application through different electrode groups at different times, and/or the changing of the inter-electrode distance and configuration by using movable RF electrodes may reduce or prevent electrode overheating, control RF energy distribution within the skin and enable use of the devices and/or for different skin treating applications.

39 Claims, 16 Drawing Sheets

(56) References Cited

U.S. PATENT DOCUMENTS

| | | | |
|---|---|---|---|
| 5,208,521 A | 5/1993 | Aoyama | |
| 5,235,514 A | 8/1993 | Matsuzaki | |
| 5,296,794 A | 3/1994 | Lang et al. | |
| 5,405,368 A | 4/1995 | Eckhouse | |
| 5,536,267 A | 7/1996 | Edwards et al. | |
| 5,542,916 A * | 8/1996 | Hirsch et al. | 604/22 |
| 5,620,481 A * | 4/1997 | Desai et al. | 607/101 |
| 5,660,836 A | 8/1997 | Knowlton | |
| 5,755,753 A | 5/1998 | Knowlton | |
| 5,871,524 A | 2/1999 | Knowlton | |
| 5,919,219 A | 7/1999 | Knowlton | |
| 5,948,011 A | 9/1999 | Knowlton | |
| 6,241,753 B1 | 6/2001 | Knowlton | |
| 6,273,884 B1 | 8/2001 | Altshuler et al. | |
| 6,307,181 B1 | 10/2001 | Hashimoto | |
| 6,311,090 B1 | 10/2001 | Knowlton | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,405,090 B1 | 6/2002 | Knowlton | |
| 6,413,255 B1 * | 7/2002 | Stern | 606/41 |
| 6,425,912 B1 | 7/2002 | Knowlton | |
| 6,430,446 B1 | 8/2002 | Knowlton | |
| 6,438,424 B1 | 8/2002 | Knowlton | |
| 6,453,202 B1 | 9/2002 | Knowlton | |
| 6,461,378 B1 | 10/2002 | Knowlton | |
| 6,470,216 B1 | 10/2002 | Knowlton | |
| 6,506,189 B1 | 1/2003 | Rittman, III et al. | |
| 6,533,775 B1 | 3/2003 | Rizoiu | |
| 6,662,054 B2 | 12/2003 | Kreindel et al. | |
| 6,702,808 B1 | 3/2004 | Kreindel | |
| 6,749,626 B1 | 6/2004 | Bhat et al. | |
| 6,766,202 B2 * | 7/2004 | Underwood et al. | 607/99 |
| 2002/0120261 A1 * | 8/2002 | Morris et al. | 606/41 |
| 2003/0195502 A1 * | 10/2003 | Garabedian et al. | 606/41 |
| 2004/0147978 A1 * | 7/2004 | Bernhard et al. | 607/50 |
| 2006/0064083 A1 | 3/2006 | Khalaj et al. | |
| 2006/0079887 A1 | 4/2006 | Buysse et al. | |
| 2007/0179490 A1 | 8/2007 | Azar et al. | |

FOREIGN PATENT DOCUMENTS

| | | |
|---|---|---|
| WO | WO 93/00958 A | 1/1993 |
| WO | WO 00/53113 A | 9/2000 |
| WO | WO2006/017666 | 2/2006 |
| WO | WO 2007/088541 | 8/2007 |
| WO | WO 2007/109194 | 9/2007 |
| WO | WO 2008/005477 | 1/2008 |
| WO | WO 2008/012827 | 1/2008 |

OTHER PUBLICATIONS

Australian Office Action of Application No. 2007278023 dated Jan. 3, 2012.
Israeli Office Action of Application No. 196707 dated Jan. 23, 2012.
U.S. Appl. No. 11/828,371, Co-Pending, Azar et al.
U.S. Appl. No. 11/955,416, Co-Pending, Shalev et al.
Supplementary European Search Report of Application No. EP 07 79 0000 mailed on Jan. 2, 2013.

* cited by examiner

APPARATUS AND METHOD FOR NON-INVASIVE TREATMENT OF SKIN TISSUE

CROSS-REFERENCE TO RELATED US APPLICATIONS

This application claims priority from and the benefit of U.S. Provisional Patent Application Ser. No. 60/833,474 filed on Jul. 27, 2006 entitled "APPARATUS AND METHOD FOR NON-INVASIVE TREATMENT OF SKIN TISSUE" incorporated herein by reference in its entirety.

FIELD OF THE INVENTION

This invention relates in general to the field of non-invasive treatment of skin tissue by electromagnetic radiation and more particularly to devices for skin treatment by application of RF energy.

BACKGROUND OF THE INVENTION

The skin is made up of three distinct layers. The top layer is called the epidermis. The epidermis is translucent. That is, it allows light to pass partially through it, rather as frosted glass does. The epidermis does not contain any blood vessels but gets its oxygen and nutrients from the deeper layers of the skin. At the bottom of the epidermis is a very thin membrane called the basement membrane which attaches the epidermis firmly, but not rigidly, to the underlying layer. The second layer lies deeper and is called the dermis. It contains blood vessels, nerves, hair roots and sweat glands. Below the dermis lies a layer of fat, the subcutaneous fat. The depth of this layer differs from one person to another. It contains larger blood vessels and nerves, and is made up of clumps of fat-filled cells called adipose cells.

The subcutaneous fat lies on the muscles and bones, to which the whole skin structure is attached by connective tissue. The attachment is quite loose, so the skin can move fairly freely. If the subcutaneous tissues fill up with too much fat, the areas of attachment become more obvious and the skin cannot move as easily. This is what gives rise to the notorious cellulite.

The junction between the epidermis and the dermis is not straight but undulates like rolling hills, more markedly so in some areas of the body than others. A series of finger-like structures called rete pegs project up from the dermis, and similar structures project down from the epidermis. These projections increase the area of contact between the layers of skin, and help to prevent the epidermis from being sheared off.

Excess adipose tissue is responsible for such medical problems as obesity, cellulites, loose skin, and wrinkles. By reducing the size of fat cells, the appearance of the outer layer of the skin can be improved. The reduction of adipose tissue in the sub-dermal layer often provides the following medical and cosmetic solutions: weight reduction, cellulite reduction, loose skin reduction, deep wrinkle reduction and body re-contouring. Reduction of the fat content may also cause skin tightening. Wrinkles are created in skin due to the breakage of collagen fibers and to the penetration of fat into the dermal layer of the skin.

Most existing wrinkle treatment methods target the collagen but do not have a significant effect on deep wrinkles. Radio frequency (RF) energy has been actively used for the treatment of epidermal and dermal layers of the skin. For example U.S. Pat. No. 6,749,626 describes the use of RF energy for collagen formation in the dermis. U.S. Pat. No. 6,241,753 describes a method for collagen scar formation. U.S. Pat. Nos. 6,470,216, 6,438,424, 6,430,446 and 6,461,378 disclose methods and devices for destroying the collagen matrix using RF, cooling and a special electrode structure that smoothes the skin surface. U.S. Pat. Nos. 6,453,202, 6,405,090, 6,381,497, 6,311,090, 5,871,524 and 6,425,912 describe methods and devices for delivering RF energy to the skin using membrane structure. U.S. Pat. Nos. 6,453,202 and 6,425,912 describe a method and a device for delivering RF energy to the skin using dielectric electrodes. U.S. Pat. Nos. 6,381,498, 6,377,855, 5,919,219, 5,948,011 and 5,755,753 describe methods of collagen contraction using RF energy, and a reverse temperature gradient on the skin surface. U.S. Pat. Nos. 6,378,380, 6,377,854 and 5,660,836 describe methods of lypo-sculpturing using RF energy and external cooling to affect the collagen inside the adipose tissue.

Another method to reduce and redistribute adipose tissue is skin massaging. This method is based on improving of blood circulation and increasing fat metabolism. U.S. Pat. No. 6,662,054 describes a method for skin massaging in combination with non-aggressive RF heating for increasing skin and fat metabolism.

U.S. Pat. No. 6,273,884 discloses simultaneous application of optical energy and negative pressure to the skin in order to treat a skin defect. This method is limited by the light penetration depth, which does not exceed a 1-2 millimeters.

U.S. Pat. No. 5,143,063 describes a method based on thermal destruction of fat using the focusing of microwave or ultrasound energy in adipose tissue. But both types of energy are very expensive and its safety limitations are not clear.

The above cited methods and devices attempt to solve the problems created by excess adipose tissue such as body contouring, loose skin, and deep wrinkles, by contracting the superficial collagen tissue at a defined depth. These methods are limited in their penetration depth. A more effective and longer lasting result would be achieved by simultaneously heating the dermis and adipose tissue of the skin. However, in order to reach these layers, it is necessary to deliver RF current into the dermis and fat tissue to a depth of over 2 mm without damaging the skin.

Recently, a new RF system was introduced into the market by ALMA lasers Florida, USA. The system uses two different RF electrode configurations for RF energy delivery to the skin: a monopolar electrode configuration and a bipolar electrode configuration. A monopolar hand-piece is used for deep tissue heating of skin tissues while a different bipolar hand-piece is used for superficial heating of the skin. The disadvantages of using this method and system is that the two different hand-pieces (monopolar and bipolar) have to be separately used, increasing the complexity and cost of the system and doubling the time required for treatment of the same skin region resulting in increased cost of treatment. Additionally, a monopolar configuration for deep tissue heating is less beneficial because the current may typically find a flow path of low resistance where fat cells would not be directly affected.

An additional problem which is common to most RF treatments of skin fat is the electrode heating problem. The density of an RF current is always higher around the surface of the RF electrode applied to the skin surface. In order to avoid overheating the skin, various different methods for skin cooling may have to be applied. Cooling may be applied prior the RF energy application or/and simultaneously. However, the use of a skin cooling device in combination with RF energy delivery device increases the cost of the combined system and result in a cumbersome and more expensive unit. Moreover, cooling of the skin reduces the efficacy of the treatment resulting in more treatment sessions and longer treatment time.

SUMMARY OF THE INVENTION

There is therefore provided, in accordance with another embodiment of the devices of the present application, a device for treatment of skin tissue. The device includes at least one RF electromagnetic energy generating unit, a plurality of electrodes electrically connectable to the RF electromagnetic energy generating unit for applying RF electromagnetic energy to the skin and at least one controller unit operatively connected to the at least one RF electromagnetic energy generating unit for controlling the application of electromagnetic energy by the at least one RF electromagnetic energy generating unit to at least one group of electrodes controllably selected from the plurality of electrodes and for controllably changing the selected group of electrodes during the operation of the device.

Furthermore, in accordance with another embodiment of the devices of the present application, the device may further include a power source for energizing the at least one RF electromagnetic energy generating unit and the at lease one controller unit.

Furthermore, in accordance with another embodiment of the devices of the present application, the at least one group of electrodes is selected from, a pair of electrodes in a bipolar configuration, three electrodes in a tripolar configuration and more than three electrodes in a multipolar configuration.

Further yet, in accordance with another embodiment of the devices of the present application, the at least one RF energy generating unit is adapted to operate at any frequency or frequency band in the range of 0.35 MHz-250 MHz.

Furthermore, in accordance with another embodiment of the devices of the present application, the device may include at least one sensor.

Furthermore, in accordance with another embodiment of the devices of the present application, the at least one sensor is connected to the at least one controller unit for providing output signals to the controller unit.

Furthermore, in accordance with another embodiment of the devices of the present application, the at least one sensor is selected from one or more skin temperature sensors, one or more electrode temperature sensors, one or more velocity sensors, one or more electrode contact sensors, and any combinations thereof.

Further yet, in accordance with another embodiment of the devices of the present application, the at least one sensor may be selected from a sensor for sensing at least one physical parameter of at least one electrode of the plurality of electrodes, a sensor for sensing the velocity of the device relative to the skin and a sensor for sensing at least one physical parameter of the skin.

Furthermore, in accordance with another embodiment of the devices of the present application the at least one physical parameter of the skin is the temperature of at least one region of said skin.

Furthermore, in accordance with another embodiment of the devices of the present application, the at least one physical parameter of the at least one electrode is selected from the temperature of at least one region of the electrode and the presence or absence of contact between the electrode and the skin.

Furthermore, in accordance with another embodiment of the devices of the present application, the at least one controller is configured for processing signals received by the at least one sensor to obtain processed data and for performing based on the data one or more actions selected from, terminating the application of RF electromagnetic energy to the skin through one or more groups of the electrodes, initiating the application of RF electromagnetic energy to the skin through one or more groups of the electrodes, terminating the application of RF electromagnetic energy to the skin through at least a first group of the electrodes and initiating the application of RF electromagnetic energy to the skin through at least a second group of electrodes different than the first group of electrodes, and terminating the application of RF electromagnetic energy to the skin through all currently energized electrodes of the device.

Furthermore, in accordance with another embodiment of the devices of the present application, the device further includes a housing for housing one or more components selected from the plurality of electrodes, the at least one controller unit, a power source, the at least one RF electromagnetic energy generating unit, one or more sensor units and any combinations thereof.

Furthermore, in accordance with another embodiment of the devices of the present application, the device includes an applicator unit configured to be applied to the skin. The applicator unit includes a housing for housing one or more components selected from the plurality of electrodes, the at least one controller unit, a power source, the at least one RF electromagnetic energy generating unit, one or more sensor units and any combinations thereof.

Furthermore, in accordance with another embodiment of the devices of the present application, the device includes an RF electrode assembly. The RF electrode assembly includes a housing and at least the plurality of RF electrodes attached to the housing.

Furthermore, in accordance with another embodiment of the devices of the present application, said one or more sensors are attached to said RF electrode assembly.

Furthermore, in accordance with another embodiment of the devices of the present application, the RF electrode assembly is selected from a fixed RF electrode assembly and a detachable RF electrode assembly detachably attachable to the device.

Furthermore, in accordance with another embodiment of the devices of the present application, the RF electrode assembly is a detachable RF electrode assembly detachably attachable to the device, and the housing of the RF electrode assembly includes electrical contacts for electrically connecting the RF electrodes to the at least one RF energy generating unit.

Furthermore, in accordance with another embodiment of the devices of the present application, the electrical contacts are also shaped to mechanically attach the RF electrode assembly to the device.

Furthermore, in accordance with another embodiment of the devices of the present application, the RF electrode assembly is selected from a re-useable RF electrode assembly and a disposable RF electrode assembly.

Furthermore, in accordance with another embodiment of the devices of the present application, the at least one controller unit is configured to control the application of RF electromagnetic energy to the skin through different groups of electrodes of the plurality of electrodes at different times during the application of the RF electromagnetic energy to the skin.

Furthermore, in accordance with another embodiment of the devices of the present application, at least one electrode of the plurality of electrodes is a movable electrode.

Furthermore, in accordance with another embodiment of the devices of the present application, the movable electrode is selected from an electrode movable in a direction generally perpendicular to the surface of the skin, an electrode laterally movable along the surface of the skin and an electrode movable in directions generally perpendicular to as well as generally lateral along the surface of the skin.

Furthermore, in accordance with another embodiment of the devices of the present application, the device further includes at least one electrode moving unit coupled to the at least one electrode for moving the at least one electrode relative to at least one other electrode of the plurality of electrodes.

Furthermore, in accordance with another embodiment of the devices of the present application, the electrode moving unit includes a an electrode moving mechanism selected from a motor, a linear motor, a non-linear motor, a gear coupled motor, an electromechanical moving mechanism, an electromagnetic moving mechanism and a solenoid actuated moving mechanism.

Furthermore, in accordance with another embodiment of the devices of the present application, the at least one controller unit is configured to controllably activate the electrode moving unit to change the distance between the at least one electrode coupled to the electrode moving mechanism and at least one other electrode of the plurality of electrodes.

Furthermore, in accordance with another embodiment of the devices of the present application, one or more electrodes of the plurality of electrodes is a spring mounted electrode.

Furthermore, in accordance with another embodiment of the devices of the present application, the at least one RF energy generating unit is a single RF generating unit operable at or about a single RF frequency or a single RF frequency band.

Furthermore, in accordance with another embodiment of the devices of the present application, the device also includes a phase shifting unit connected to at least one RF electrode and to the RF energy generating unit for shifting the phase of the RF electromagnetic waves applied to the skin through the at least a first RF electrode relative to the phase of an RF electromagnetic wave applied to the skin through at least a second RF electrode different than the first RF electrode.

Furthermore, in accordance with another embodiment of the devices of the present application, the at least one RF energy generating unit includes a plurality of RF energy generating units, each RF generating unit is operable at or about a single RF frequency or a single RF frequency band. The RF frequencies or the RF frequency of at least some of said plurality of RF energy generating units are different.

Furthermore, in accordance with another embodiment of the devices of the present application, the device also includes at least one phase shifting unit connected to at least one RF electrode and to one or more RF energy generating units of the plurality of RF energy generating units for shifting the phase of the RF electromagnetic waves applied to the skin through the at least a first RF electrode relative to the phase of an RF electromagnetic wave applied to the skin through at least a second RF electrode different than the first RF electrode.

Furthermore, in accordance with another embodiment of the devices of the present application, the device also includes a multiplexing switching unit connected to the plurality of RF energy generating units, the plurality of electrodes and the at least one controller unit for controllably applying RF energy from any combination of RF energy generating units selected from the plurality of RF energy generating units to any electrode or electrode combination selected from the plurality of electrodes.

Furthermore, in accordance with another embodiment of the devices of the present application, the multiplexing switching unit includes one or more phase shifting units.

Furthermore, in accordance with another embodiment of the devices of the present application, the device is configured for being controllably operable in a plurality of different operating modes, wherein, in each different operating mode the RF frequency or RF frequencies applied to the skin are different than the RF frequency or RF frequencies applied to the skin in other operating modes.

Furthermore, in accordance with another embodiment of the devices of the present application, the RF frequency or frequencies used in at lease some operating mode of the plurality of operating modes are selected to preferentially heat selected different types of skin tissues.

Furthermore, in accordance with another embodiment of the devices of the present application, the different types of skin tissues are selected from, fatty skin tissue, hypodermal adipose tissue, rete pegs, non-fatty dermal tissue, epidermal tissue and combinations thereof.

Furthermore, in accordance with another embodiment of the devices of the present application, the device is configured for simultaneously applying combinations of different RF frequencies or different RF frequency bands through any suitable electrodes for simultaneously heating combinations of different type of skin tissues.

Furthermore, in accordance with another embodiment of the devices of the present application, the RF frequency or RF frequencies applied to the skin in a first operating mode are in the range of 0.35-1.5 MHz and the RF frequency or RF frequencies applied to the skin in a second operating mode are in the range of 4-15 MHz.

Furthermore, in accordance with another embodiment of the devices of the present application, the RF frequency or RF frequencies applied to the skin in a first operating mode are in the range of 0.35-1.5 MHz, the RF frequency or RF frequencies applied to the skin in a second operating mode are in the range of 4-15 MHz, and the RF frequencies applied to the skin in a third operating mode include frequencies in the range of 0.35-1.5 MHz and in the range of 4-15 MHz.

There is also provided a method for treatment of skin tissue. The method includes the steps of providing a plurality of electrodes for applying RF electromagnetic energy to the skin, applying RF electromagnetic energy to the skin through at least a first group of electrodes selected from the plurality of electrodes for a first time period, and applying RF electromagnetic energy to the skin through at least a second group of electrodes different from the at least first group of electrodes selected from the plurality of electrodes for a second time period different than the first time period.

Furthermore, in accordance with another embodiment of the methods of the present application, the application of RF electromagnetic energy to the skin through the at least first group of electrodes is stopped during the second time period to allow the first group of electrodes to cool during the second time period.

Furthermore, in accordance with another embodiment of the methods of the present application, the method also includes repeating the first step of applying and the second step of applying a plurality of times.

Furthermore, in accordance with another embodiment of the methods of the present application, the RF electromagnetic energy is applied to the skin at any frequency or frequency band in the range of 0.35 MHz-250 MHz.

Furthermore, in accordance with another embodiment of the methods of the present application, the RF electromagnetic energy is applied to the skin at a frequency or frequency band selected from a first frequency range and at a second frequency or frequency band selected from a second frequency range.

Furthermore, in accordance with another embodiment of the methods of the present application, the first step of applying includes applying RF electromagnetic energy to the skin through the first group of electrodes at a frequency or frequencies selected from, a frequency or frequency band included in the first frequency range, a frequency or frequency band included in the second frequency range, and a combination of at least one frequency or frequency band included in the first frequency range and at least one frequency or frequency band included in the first frequency range.

Furthermore, in accordance with another embodiment of the methods of the present application, the second step of applying includes applying RF electromagnetic energy to the skin through the second group of electrodes at a frequency or frequencies selected from, a frequency or frequency band included in the first frequency range, a frequency or frequency band included in the second frequency range, and at least one frequency or frequency band included in the first frequency range and at least one frequency or frequency band included in the first frequency range.

Furthermore, in accordance with another embodiment of the methods of the present application, the said first frequency range is 0.35 MHz-1.5 MHz, and the second frequency range is 4 MHz-15 MHz.

Furthermore, in accordance with another embodiment of the methods of the present application, during the first step of applying and the second step of applying, the first group of electrodes and the second group of electrodes are operated at a configuration selected from, a pair of electrodes in a bipolar configuration, three electrodes in a tripolar configuration and more than three electrodes in a multipolar configuration.

Furthermore, in accordance with another embodiment of the methods of the present application, the method also includes the step of terminating the application of RF energy to the skin through any electrode group selected from the at least first group of electrodes and the at least second group of electrodes if the temperature of the skin or of at least one electrode of the electrodes exceeds a threshold value.

Furthermore, in accordance with another embodiment of the methods of the present application, the method also includes the step of terminating the application of RF energy to the skin through any electrode group selected from the at least first group of electrodes and the at least second group of electrodes if the velocity of the electrodes relative to the skin is lower than a threshold value.

Furthermore, in accordance with another embodiment of the methods of the present application, the method also includes the step of terminating the application of RF energy to the skin through any electrode group selected from the at least first group of electrodes and the at least second group of electrodes if any electrode of the plurality of electrodes does not contact the skin during the applying of RF energy to the skin.

Furthermore, in accordance with another embodiment of the methods of the present application, the method also includes the step of moving at least one electrode of the at least first group of electrodes relative to another electrode of the at least first group of electrodes before, during or after the first time period.

Furthermore, in accordance with another embodiment of the methods of the present application, the method also includes the step of moving at least one electrode of said at least second group of electrodes relative to another electrode of said at least second group of electrodes before, during or after said second time period.

Furthermore, in accordance with another embodiment of the methods of the present application, the method further includes the step of changing the distance between at least one electrode of the at least first group of electrodes relative to another electrode of the at least first group of electrodes before, during or after the first time period.

Furthermore, in accordance with another embodiment of the methods of the present application, the method also includes the step of changing the distance between at least one electrode of the at least second group of electrodes relative to another electrode of the at least second group of electrodes before, during or after the second time period.

There is also provided, in accordance with another embodiment of the methods of the present application, a method for treatment of skin tissue, the method includes the steps of providing a plurality of electrodes for applying RF electromagnetic energy to the skin, at least one electrode of the plurality electrodes is movable relative to at least a second electrode of said plurality of electrodes, applying electromagnetic energy to the skin through at least a first group of electrodes including the movable electrode, and moving the at least one movable electrode to change the distance between the at least one movable electrode and at least another electrode of the plurality of electrodes.

There is also provided, in accordance with an embodiment of the devices of the present application, a device for treatment of skin tissue. The device includes at least one RF electromagnetic energy generating unit, a plurality of electrodes electrically connectable to the at least one RF electromagnetic energy generating unit for applying RF electromagnetic energy to the skin, at least one electrode moving unit for moving at least one movable electrode of the plurality of electrodes relative to at least a second electrode of the plurality of electrodes, and at least one controller unit operatively connected to the at least one RF electromagnetic energy generating unit for controlling the application of RF electromagnetic energy by the at least one RF electromagnetic energy generating unit to at least one group of electrodes of the plurality of electrodes and for controlling the moving of the at least one movable electrode by the at least one electrode moving unit.

There is further provided, in accordance with an embodiment of the devices of the present application, a device for treatment of skin tissue. The device includes a plurality of electrodes for applying RF electromagnetic energy to the skin. At least a first electrode of the plurality of electrodes is movable relative to at least a second electrode of the remaining electrodes of the plurality of electrodes such that the distance between the at least first electrode and the at least a second electrode may be controllably varied. The device also includes one or more electromagnetic RF energy generating units and a controller unit operatively coupled to the plurality of electrodes and to the one or more RF electromagnetic energy generating units. The controller unit is configured for controlling the application of RF electromagnetic energy by the one or more RF electromagnetic energy generating units to at least one pair of electrodes selected from the plurality of electrodes.

There is also provided an RF electrode assembly for use in a skin treating device. The RF electrode assembly includes a housing and a plurality of RF electrodes attached to the housing. The RF electrode assembly is connectable to an RF energy generating unit of the device.

Finally, there is also provided kit including the skin treatment device and one or more attachable RF electrode assembly each including a plurality of electrodes. The one or more RF electrode assemblies are detachably attachable to the device.

BRIEF DESCRIPTION OF THE DRAWINGS

The devices systems and methods of the present application are described herein, by way of example only, with reference to the accompanying drawings, in which like components are designated by like reference numerals, wherein.

DETAILED DESCRIPTION OF THE INVENTION

Notation Used Throughout

Figure 1:
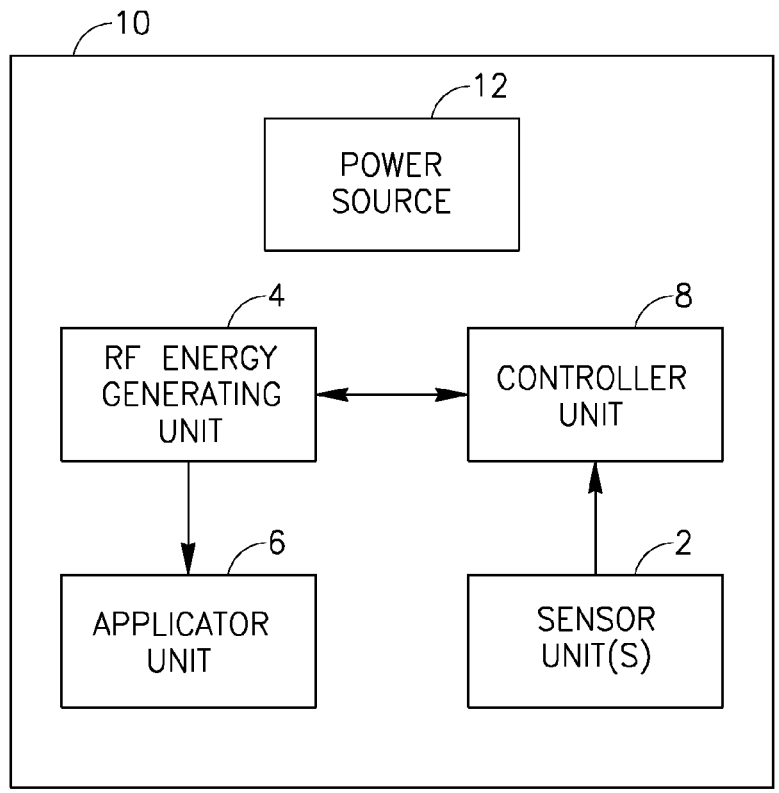
FIGS. 1-2 are schematic block diagrams illustrating the components of two devices for skin treatment, in accordance with two embodiments of the device.

The following notation is used throughout this document.

| Term | Definition |
| --- | --- |
| AC | Alternating current |
| DC | Direct current |
| EM | Electromagnetic |
| GHz | Gigahertz |
| LCD | Liquid crystal display |
| LED | Light emitting diode |
| MHz | Megahertz |
| MTBF | Mean time before failure |
| OLED | Organic light emitting diode |
| RF | Radio Frequency |

The present application provides methods, devices and systems using multiple RF electrodes, electrode pair switching methods, and electrode group switching methods for substantially reducing RF electrode heating.

The present application also provides methods, devices and systems using multiple RF electrodes and/or RF electrode groups including one or more controllably movable RF electrodes capable of providing variable RF electrode spatial configurations for obtaining better control of the depth of penetration of the applied RF energy to achieve better and more uniform distribution of RF energy application to superficial and deeper skin regions.

The present application also provides methods, devices and systems using multiple RF electrodes and/or RF electrode groups (either movable electrodes or stationary electrodes) controllably couplable to one or more RF energy generating units to enable the controlled application of one or more RF frequencies and/or one or more RF frequency bands to a any selected combination of RF electrodes for obtaining better control of RF induced heating of various different skin regions or skin layers based on the efficacy of RF energy absorption of different RF frequencies by different tissue types.

By controlling the RF frequency and/or RF frequencies applied through all or some of the RF electrodes and/or RF electrode groups the devices, methods and systems disclosed herein enable either preferential heating of different skin tissues (such as, but not limited to, preferential RF induced heating of fatty or sub-epidermal adipose skin tissues for cellulite reduction skin treatment, or more uniform heating of all skin layers for skin tightening application).

In order to prevent overheating of the electrodes and subsequently the undesirable overheating of the skin, the devices and systems of the present application apply the RF energy to the skin by using one or more pairs of electrodes for applying RF energy to the skin. One or more electrode pairs are used for RF energy application for a relatively short period of time which is insufficient to cause excessive heating of the electrodes of the pair(s). The device or system then switches the first pair(s) off while switching on for a similarly short period of time other different pair(s) of cool electrodes for delivery of RF energy to the skin while the first pair(s) is/are allowed to cool. Switching back and forth between pairs of electrodes let them cool down sufficiently to avoid undesirable electrode overheating. This method of switching between electrode pairs may also be implemented by sensing the temperature of the currently active electrodes or electrode pairs and when they reach a temperature above a certain threshold switching to the next and colder pair(s) of electrodes.

The distribution of RF current depends, inter alia, on the geometry of electrodes and the distance between them. For bipolar electrode configurations, the RF energy penetration using two long cylindrical shaped electrodes is approximately equal to half the distance between the electrodes, while for two point source electrodes the penetration depth is approximately the distance between the two electrodes. For predetermined electrode geometry the depth of penetration may be controlled by changing the distance between the electrodes. The changing of the distance between the electrodes of a pair may be accomplished by either moving one or both of the electrodes of the pair to change the distance between the electrodes (electrode separation) or by alternatingly switching between various electrode pairs separated by different distances as is described in detail hereinafter.

In accordance with yet other embodiments of the devices systems and methods disclosed in the present application, combinations of electrode pair switching and movable electrodes (variable pair geometry) methods and devices may be used to achieve better depth penetration and simultaneous or sequential heating of both superficial and deep skin tissues by RF energy and also safer RF energy application to the skin by avoiding electrode overheating.

Figure 2:
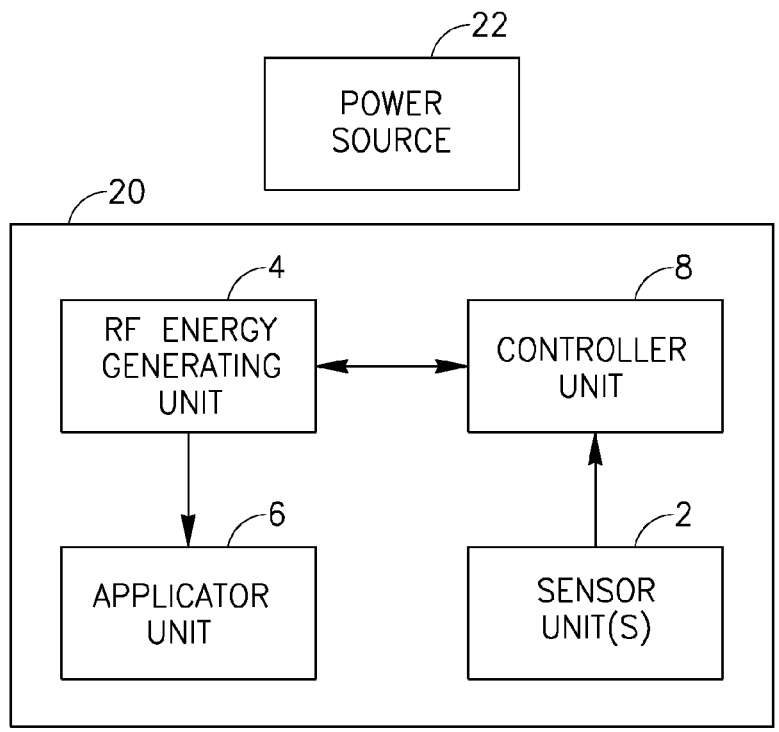

Reference is now made to FIGS. 1 and 2 which are schematic block diagrams illustrating the components of two devices for skin treatment in accordance with two embodiments of the device. The device 10 of FIG. 1 includes an RF energy generating unit 4, constructed and operative as is known in the art. The device 10 also includes an applicator unit 6 suitably electrically coupled to the RF energy generating unit 4 for transferring the RF energy to the skin tissue (not shown). The applicator unit 6 may be any type of applicator including a plurality of electrically conducting RF electrodes (the electrodes are not shown in detail in FIGS. 1 and 2, for the sake of clarity of illustration) as is well known in the art.

The device 10 also includes a controller unit 8 for controlling the RF energy generating unit 4 and its application to the electrodes included in the applicator unit 6 and (optionally) the arrangement and/or movement and/or operation of the electrodes included in the applicator unit 6 for applying RF energy to the skin. The device 10 may also (optionally, but not obligatorily) include one or more sensor units 2 for sensing the skin parameters (such as, for example, for sensing the temperature of one or more regions of the treated skin, as disclosed in detail hereinafter with respect to the skin treating device 220 of FIGS. 12A-12B), and/or the velocity (speed of movement) of the applicator unit 6 relative to the skin (not shown) and/or the temperature of one or more of the electrodes included in the applicator unit 6 as disclosed in detail hereinafter.

The device 10 also includes a power source 12 for providing power to the RF energy generating unit 4 and to the controller unit 8 and/or (optionally to the sensor(s) 2). The power source 12 is preferably an electrical power source. It is noted that while the power source 12 is shown as included within the device 10, this is not obligatory and the power source 12 may be disposed outside the device 10 and may provide power to the components of the device 10 via a suitable, preferably isolated electrically conducting wires, power cables, or the like (not shown in FIGS. 1-2 for the sake of clarity of illustration, but see FIG. 3 for an example). It is noted that the power source 12 may be any suitable type of DC or AC power source known in the art, including, but not limited to, a battery, a primary or a rechargeable electrochemical cell, a fuel cell, a photovoltaic cell or solar cell (coupled to a suitable charge storage element), a mains AC outlet, a DC (direct current) power supply or an AC (alternating current) power supply, or the like.

It is noted that the construction and operation of RF energy generating units is well known in the art, is not the subject matter of the present invention, and is therefore not described in detail hereinafter. Generally, any suitable type of RF energy generating unit known in the art or available commercially may be used in implementing the various different embodiments disclosed in the present application. For example, a model SURTRON 80 RF generator commercially available from LED Spa, Italy may be used for implementing the RF generating unit(s) disclosed herein (such as, but not limited to the RF energy generating unit 4 of FIGS. 1-2). In another example, a model BC 50M/M RF generator commercially available from ELMED Inc, U.S.A. may be used for implementing the RF generating unit(s) of the present application (such as, but not limited to, the RF energy generating unit 4 of FIGS. 1-2). In yet another example, a model Wet-Field® Diathermy coagulator commercially available from Medtronic Inc, U.S.A. may be used for implementing the RF generating unit(s) of the present application (such as, but not limited to the RF energy generating unit 4 of FIGS. 1-2).

Similarly, the construction and operation methods of controller units, such as, for example, the controller unit 8 of FIGS. 1-2 are well known in the art, are not the subject matter of the present application and are therefore not described in detail hereinafter. Briefly, any type of controller unit and or controller/processor unit known in the art may be used for implementing the controller units 8 and 13 of FIGS. 1-2 and FIGS. 14-15, respectively, including any suitably programmed commercially available controllers, microcontroller(s), microprocessor(s), data processor(s), digital signal processor(s), analog signal processor(s), hybrid digital/analog signal processor(s) and the like and any combinations thereof may be used.

It is noted that the controller units 8 and 13 may be used to control not only the RF energy generating unit(s) included in the skin treating devices described herein but may also (optionally be used to receive data from any sensor or sensors included in any of the devices and to process the data received from the sensors and use such processed data for controlling the operation of any RF energy generating unit(s) included in the device(s) and (optionally) for controlling the operation of any electrode moving mechanism or unit capable of moving the RF electrodes of the device (if such an electrode moving unit is included in the device or in the RF electrode assembly, for examples see the electrode moving units and motors illustrated in FIGS. 10A-10B, 11A-11B, 14 and 15). Such moving mechanisms may include but are not limited to the linear motor 200 of FIGS. 10A-10B or any other type of motor(s) or electrode moving mechanisms used to move the Electrode(s) included in the device.

Figure 12A:
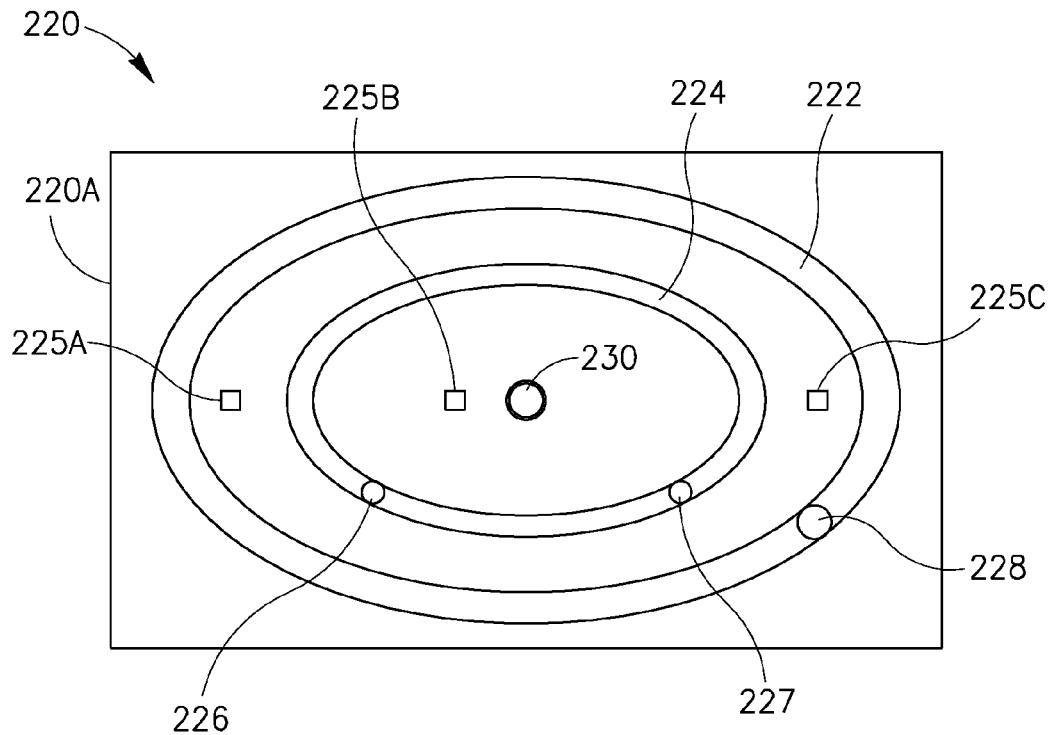
FIGS. 12A-12B are schematic top views illustrating two different electrode configurations of part of a skin treatment device having one stationary RF electrode and some RF electrodes that are movable within elliptically shaped openings, in accordance with still another embodiment of skin treating device.
Figure 12B:
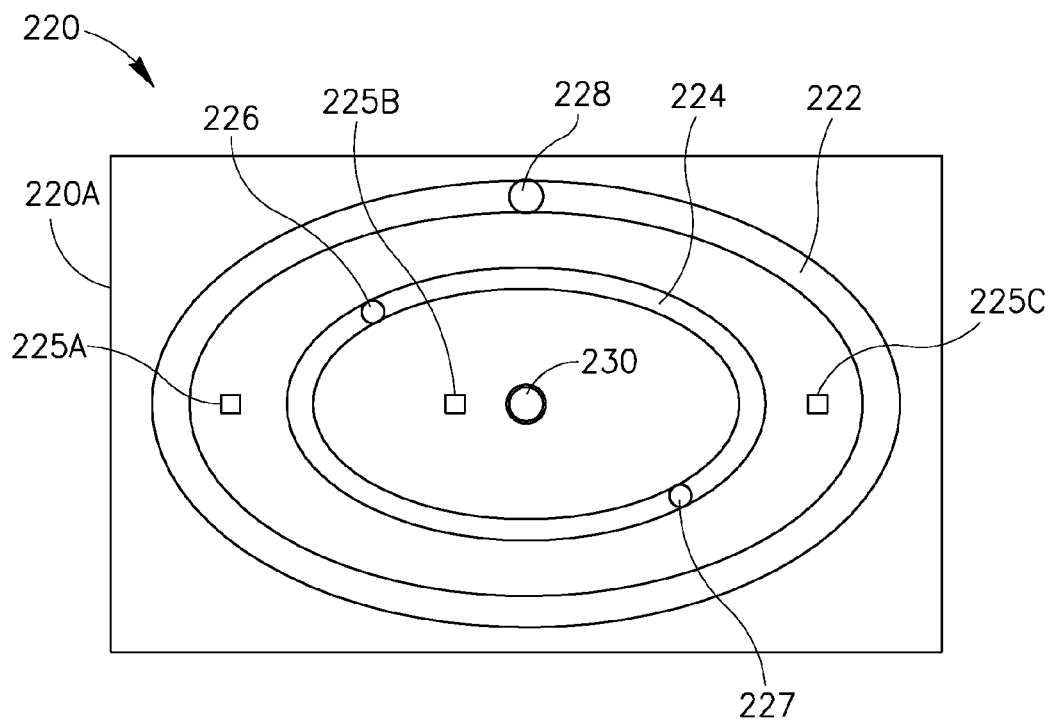

For example, the controller unit used in the devices may process signals received from temperature sensors (such as, but not limited to, the temperature sensors 225A, 225B and 225C of FIG. 12A-12B) to determine the temperature of the skin and to stop the application of RF energy to the skin through one or more electrode pair or electrode group when the determined skin temperature exceeds a threshold value. The temperature threshold value may be a fixed (factory set) threshold temperature value or may be a programmable threshold value which may be programmed or set by the user of the device through a suitable user interface, such as, but not limited to any suitable dial or other input device disposed on the applicator unit 36 (interface is not shown in FIG. 3 for the sake of clarity of illustration) or on the main unit 32 of the system 30 or by any other suitable input interface or device suitably included in any of the skin treating devices and systems described herein.

The applicator unit 6 may be any suitable RF energy transmitting unit for applying RF energy to the skin, preferably (but not obligatorily) in the frequency range of 0.35 MHz to 250 MHz. However, it may also be possible to use RF frequencies having a higher or lower frequency than the above indicated frequency range.

For example, in the RF frequency range of 0.5 MHz to 100 MHz, the applicator may include RF electrodes (not shown in FIGS. 1-2) adapted to applying RF currents through the skin. The RF electrodes may be implemented as two or more electrically conducting members adapted for contacting the skin and passing RF currents through the skin (for non-limiting examples, see the RF electrodes illustrated in FIGS. 4, 5, 6 7A-7B, 8A-8F, 9A-9C, 10A-10B, 11A-11B and 12) Typically, the RF electrodes may be arranged in pairs of bipolar arrangement (see FIG. 8 below) as is known in the art. However, the RF electrodes may also be configured in a tripolar arrangement (FIG. 7 below) where one electrode is put in contact with the skin at the site being treated while the other two electrodes may be put at a place relatively distant from the treated site.

Additionally, in embodiments having a sufficient number of RF electrodes multipolar RF electrode configurations may be used as is known in the art. For example, if there are eight different RF electrodes in the device (see for example in FIG. 13 hereinbelow), one electrode may be used in a multipolar configuration with three, four, five, six or seven other electrodes. Alternatively or additionally, if such eight RF electrodes (such as the electrodes 258A-258D and 260A-260D of FIG. 13) are used in two groups of four RF electrodes each, then within each group (such as, for example, the electrode group 258A-258D or the electrode group 260A-260D) one electrode (such as, for example, the RF electrode 260A) may be operated in a multipolar configuration in conjunction with the remaining three RF electrode of the same electrode group (i.e. the RF electrodes 260B-260D).

Alternatively or additionally larger RF electrode numbers in a device may be used in multiple RF electrode group using any suitable combinations of bipolar and/or tripolar and/or multipolar electrode configurations within each RF electrode group or between different RF electrode groups. Thus, any suitable RF electrode configuration may be used in the devices and systems of the present application, as is known in the art.

The device 20 of FIG. 2 is similar (but not identical) to the device 10 of FIG. 1 and includes the RF energy generating unit 4, the applicator unit 6, the controller unit 8 for controlling the RF energy generating unit 4, and (optionally, but not obligatorily) one or more sensor units 2 for sensing the skin parameters, and/or the velocity (speed of movement) of the applicator unit 6 relative to the skin (not shown) and/or the temperature of one or more of the electrodes included in the applicator unit 6. The construction and operation of these components may be as described for the device 10. In contrast to the device 10 which includes an internal power source 12 (FIG. 1), the device 20 is connected to an external power source 22.

The power source 22 provides power to the RF energy generating unit 4 and to the controller unit 8 and/or optionally to the sensor(s) 2. The power source 22 is preferably an electrical power source. It is noted that the power source 22 may be any suitable type of DC or AC power source known in the art, including, but not limited to, a battery, a primary or a rechargeable electrochemical cell, a fuel cell, a photovoltaic cell or solar cell (coupled to a suitable charge storage element), a mains AC outlet, a DC (direct current) power supply or an AC (alternating current) power supply, or the like.

The implementation and construction of the skin treatment devices of the present application may vary depending upon the specific treatment application. For example (FIG. 3), the device of the present application may be implemented as a tabletop or bedside system for use by a physician or cosmetician or another user. Such a system may include a main unit for housing some of the necessary electrical circuitry for providing power and control functions, safety functions providing components (optional) and/or other components of the system, and a hand-held part which may be applied to the treated skin area and which may include the applicator and optionally the sensor units.

Figure 3:
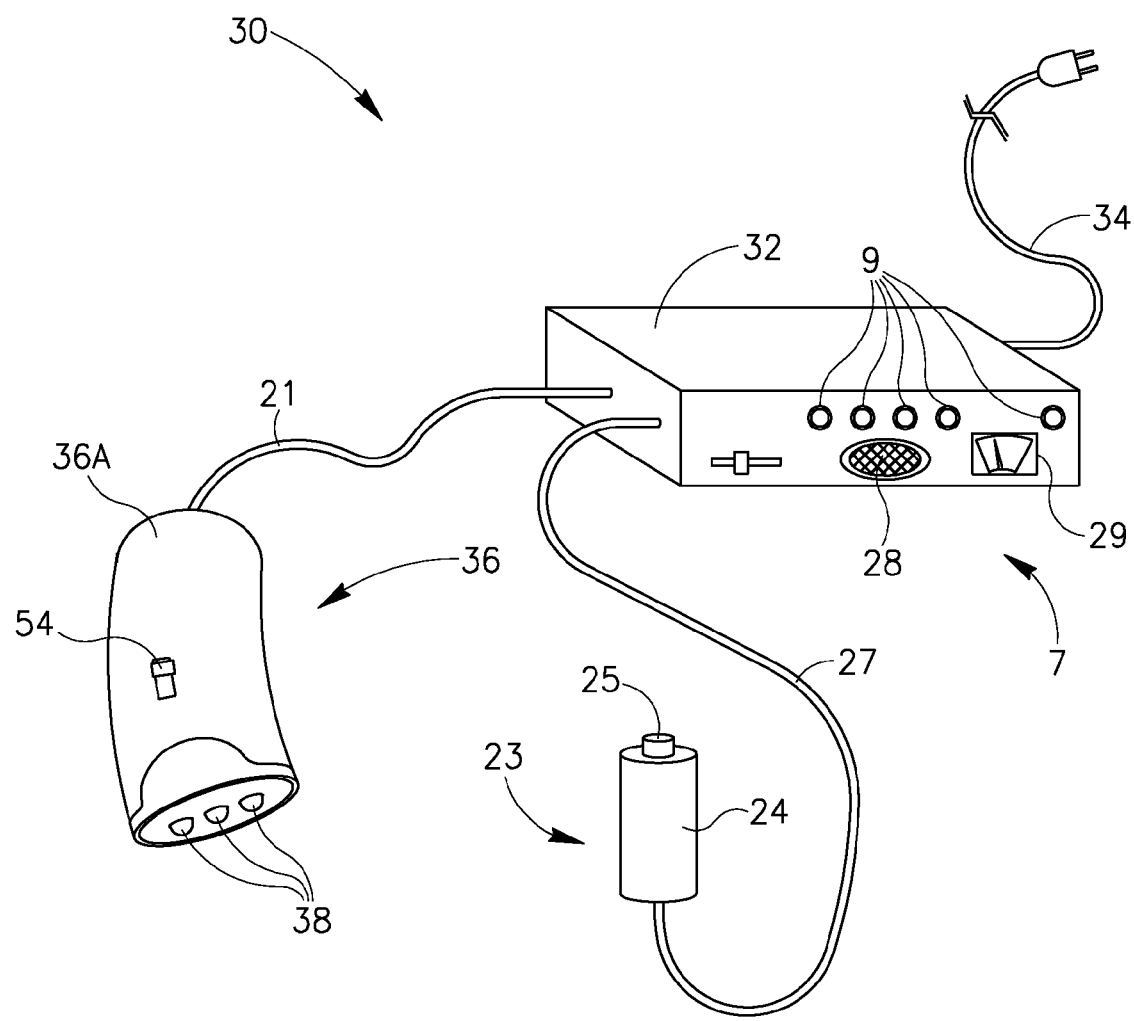
FIG. 3 is a schematic isometric view illustrating a skin treatment system including a base station and a hand held part, in accordance with an embodiment of the skin treating system.

Reference is now made to FIG. 3 which is a schematic isometric view illustrating a skin treatment system including a base station and a hand held part, in accordance with an embodiment of the systems of the present application. The system 30 includes a main unit 32 for providing power and/or for controlling various treatment parameters and safety features and a hand-held unit 36 which may include RF electrodes 38 for applying RF energy to the skin and one or more sensing units (not shown in detail). The hand-held unit 36 may include a housing 36A preferably (but not obligatorily) made from plastic or another suitable polymer based material, such as, for example, polycarbonate, Delrin®, and the like, or another suitable material, as is known in the art. The hand held unit 36 also includes a plurality of two or more RF electrodes 38 for delivering RF currents to the skin. The hand-held unit 36 is shaped and sized so that it may be conveniently held by the hand of an operator or user and applied to the skin for treating the skin. The hand-held unit 36 may also (optionally) include the electrical circuitry or part(s) of the electrical circuitry of the controller unit 8, the RF energy generating unit 4, and may also include the sensor unit(s) 2 as described hereinabove and hereinafter.

The hand held unit 36 may be connected to the main unit 32 by a suitable cable 21 which may include therein all the electrical wires (not shown) necessary for coupling the components housed within the main unit 32 to the electrical components included in the hand held unit 36.

However, preferably, in accordance with another embodiment of the system the main unit 32 may include one or more of the controller unit 8, the RF energy generating unit 4, or part(s) of the electrical circuitry thereof, and may also include electrical circuits (not shown) for processing signals or data from the sensor unit(s) 2. In the embodiment illustrated in FIG. 3, the main unit 32 includes a power cable 34, connectable to a mains AC power outlet for supplying electrical power to the device 30. However, in accordance with an embodiment of the system, the main unit 32 may include any suitable internal power source known in the art (such as, but not limited to, the power source 12 of FIG. 1).

The main unit 32 also includes a user interface 7 which may be used for communicating data and/or signals between the system 30 and the user of the system. The user interface 7 may include an (optional) display unit 29 for displaying the skin temperature or the RF electrode(s) temperature to the user of the system 30 as is disclosed in detail hereinafter. The user interface 7 may also include an (optional) speaker unit 28 for providing audible signals to the user of the system as disclosed in detail hereinafter. The user interface 7 may also include control dials 9 for controlling the operation of the system 30 by the user and for inputting data and/or control signals into the system 30 as disclosed in detail hereinafter.

The System 30 may also (optionally, but not obligatorily) include a switching unit 23. The switching unit 23 may be a hand held device configured to be comfortably hand held. The switching unit 23 has a housing 24 preferably made from a plastic material or the like. The housing 24 includes an electrical switch therein (the switch is not shown in detail for the sake of clarity of illustration). The switch included in the housing 24 may be actuated by a switching button 25 coupled to the electrical switch and movably attached within the housing 24. The switching unit 23 may be electrically coupled to the main unit 32 by a suitable cable 27 that includes all the necessary electrical wires for coupling the electrical switch included in the housing 24 to the main unit 32 to enable the switching on and off of RF power to the RF electrodes 38 of the hand held unit 36.

In operation, when the skin of a patient (not shown) is being treated by a user or operator (not shown) of the system, such as for example a cosmetician, a physician or the like, the switching unit 23 may be held by the hand of the treated patient. If the treated patient feels any type of discomfort during treatment (such as, but not limited to discomfort due to excessive heating of the skin by the RF electrodes or due to any other reason whatsoever), the patient may press the button 25 to switch off application of RF energy to the applicator 36. This arrangement is advantageous not only as an additional patient operated safety device but also due to the fact that psychologically the patient may feel better and be more relaxed during treatment just because the patient knows that the application of RF energy to his or her skin may be immediately terminated by him or her at his/her initiative.

Figure 4:
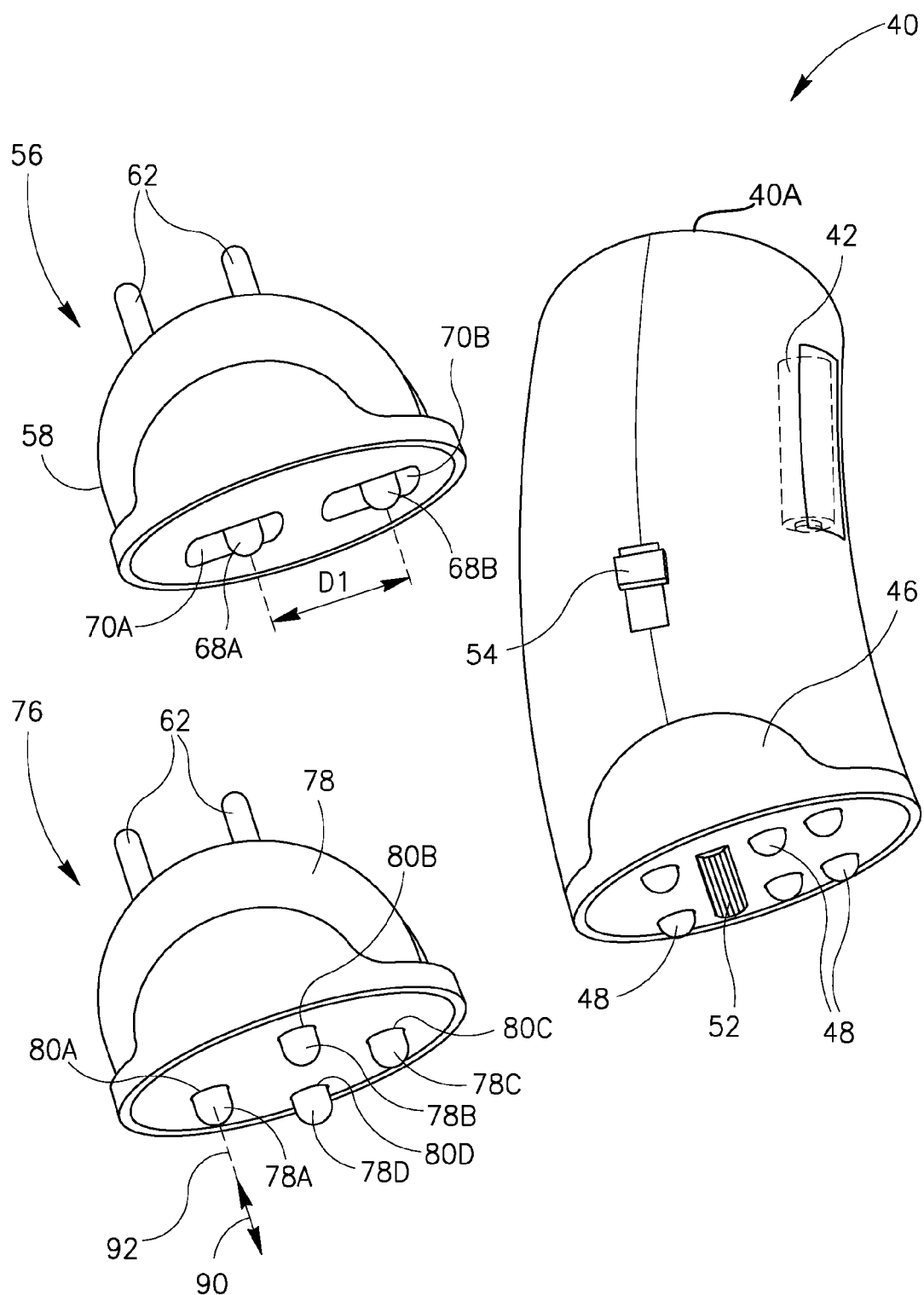
FIG. 4 is a schematic isometric view of a hand held skin treatment device, in accordance with another embodiment of skin treating device.

Reference is now made to FIG. 4 which is a schematic isometric view of a hand held skin treatment device, in accordance with another embodiment of the devices of the present application. The hand-held device 40 includes a housing 40A. The housing 40A is preferably (but not obligatorily) made from plastic or another suitable polymer based material such as, for example, polycarbonate, Delrin®, and the like, or any other suitable material, as is known in the art. The hand-held device 40 also includes an RF electrode assembly 46. The RF electrode assembly 46 includes six RF electrodes 48 for delivering RF currents to the skin. The device 40 includes a battery 42 for providing electrical power source to the components of the device 40. However, the device 40 may include any other suitable power source as is known in the art and/or as described with respect to FIGS. 1-2. The device 40 also includes a switch 54 for turning the device 40 on and off by the user.

The device 40 also includes an RF energy generating unit 4 (not shown in FIG. 4 for the sake of clarity of illustration) such as, for example the RF energy generating, and the controller unit 8 (not shown in FIG. 4 for the sake of clarity of illustration) for controlling the RF energy generating unit 4, and (optionally, but not obligatorily) one or more sensor units for sensing the skin parameters, and/or the velocity (speed of movement) of the RF electrode assembly 46 relative to the skin (not shown) and/or the temperature of one or more of the electrodes 48 included in RF electrode assembly 46. The construction and operation of these components may be as described for the device 10 hereinabove.

Figure 5:
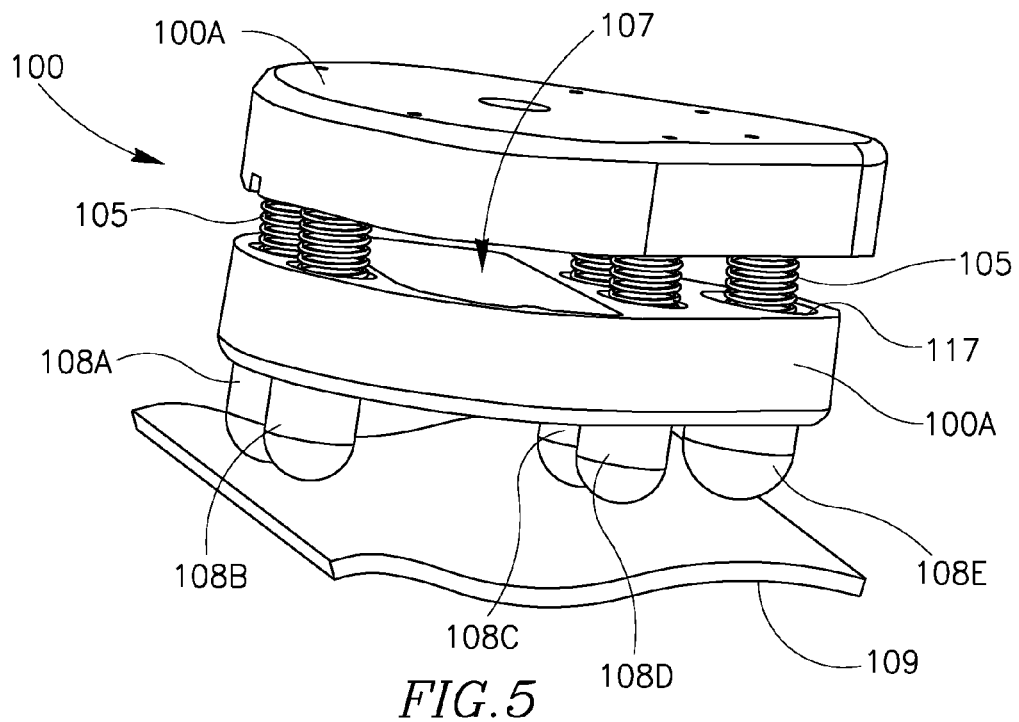
FIG. 5 is an isometric view illustrating an RF electrode assembly having five RF electrodes, in accordance with an embodiment of an RF electrode assembly.
Figure 6:
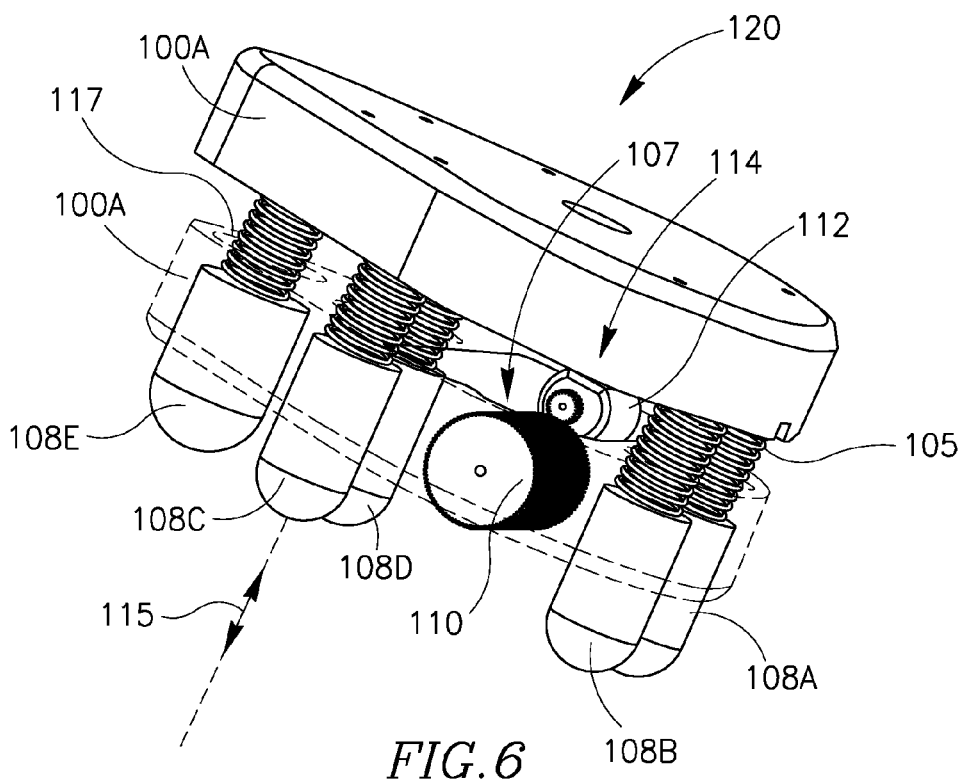
FIG. 6 is an isometric view illustrating an RF electrode assembly having five RF electrodes and a mechanical velocity sensor, in accordance with another embodiment of the of the RF electrode assembly.

The RF electrode assembly 46 includes a (optional) sensor 52 for determining the velocity of the RF electrode assembly 46 relative to the skin. The construction and operation of the sensor 52 is described in detail hereinafter and as illustrated in FIGS. 5 and 6. When the velocity of the RF electrode assembly 46 relative to the treated skin (not shown) is less than a preset or predetermined (or optionally factory preset) threshold value, the application of power to the RF electrodes may be stopped. This (optional) feature of the device 40 is an advantageous safety feature ensuring that if the RF electrodes 48 are left in contact with the skin while the device is stationary or moves too slowly with respect to the skin, the application of RF energy to the skin is interrupted to avoid excessive heating and/or burning of the skin.

Other sensors and safety mechanisms which may be included in the device 40 may include thermal sensors (not shown in FIG. 4) which may measure the temperature of the RF electrodes 48. The controller of the device 40 may be configured to interrupt the application of RF energy to the skin if the temperature of one or more of the electrodes 48 exceeds a preset or predetermined (or factory preset) value to avoid excessive heating and/or burning of the skin.

Additional safety mechanisms that may be included in the device 40 to prevent RF electrode sparking are described in detail hereinafter with respect to FIGS. 7A-7B.

In accordance with an embodiment of the device 40, the RF electrode assembly may be formed as a fixed part of the device 40, or may be non-detachably attached to the housing 40A of the device 40. Such multi-use electrode assemblies may be made from a suitable plastic such as polycarbonate, Teflon®, Delrin®, or the like, or from any other suitable electrically isolating material. The RF electrodes of such fixed multi-use electrode assemblies may be made of or may include any suitable electrically conducting substance such as, but not limited to, a metal, stainless steel 316, other types of stainless steel, bronze, Aluminum coated by Nickel, or any other type of electrically conducting material having suitable conductivity.

In accordance with another embodiment of the device 40, the RF electrode assembly 46 of the device 40 is configured as a detachable electrode assembly. The RF electrode assembly 46 may be detached from the housing 40A of the device 40 for cleaning and/or maintenance and/or replacement, as the need arises. In accordance with an embodiment of the device, the RF electrode assembly 46 is detachably attached to the housing 40A and may be detached and replaced with another new RF electrode assembly identical to the RF electrode assembly 46.

In accordance with another embodiment of the devices and systems of the present application, the device 40 may be configured to operate with a variety of different configurations of attachable/detachable and/or replaceable and/or disposable RF electrode assemblies.

Two additional exemplary differently configured detachable electrode assemblies 56 and 76 are illustrated in FIG. 4.

The RF electrode assembly 56 is a movable electrode assembly, including movable RF electrodes. The RF electrode assembly 56 includes an assembly housing 58 preferably (but not obligatorily) made from plastic or another suitable polymer based material such as, for example, polycarbonate, Delrin®, and the like, or any other suitable material, as is known in the art. The RF electrode assembly 56 also includes two movable RF electrodes 68A and 68B which are movably disposed within slot-like openings 70A and 70B formed within the housing 58. An internal mechanism (not shown in FIG. 4) allows one or more motors (not shown) included in the housing 58 to controllable move each of the RF electrodes 68A and 68B within the respective opening 70A and 70B. Thus, the distance D1 between the electrodes 68A and 68B may be varied by suitably controlling the operating of the motor(s). The motor(s) may be controlled by the controller unit 8 of the device 40.

The electrode assembly 56 also includes electrical contacts 62 which are used to electrically couple any electrical components included in the RF electrode assembly to the electrical components included in the housing 40A of the device 40. The electrical contacts 62 may provide power and/or control signals to any electrical circuits and or electromechanical parts and/or sensors included within the RF electrode assembly 56 (such as, but not limited to providing RF currents from the RF energy generator unit 4 to the RF electrodes 68A and 68B, providing control signals and/or electrical power from the controller unit 8 and/or the battery 42 to any electrical motor(s) coupled to the RF electrodes 68A and 68B, and the like).

The electrical contacts 62 may also provide a path for outputting any control signals and/or sensor generated signals or sensor generated data to any electrical circuits and or components included within the device 40 (such as, but not limited to providing electrical signals output by sensors included in the RF electrode assembly 56 to the controller circuit 8 of the device 40).

Besides operating as electrical contacts, the electrical contacts 62 may also be structurally configured to operate as and/or assist the mechanical attachment (and/or detachment) and/or locking and/or latching of the RF electrode assembly 56 onto the housing 40A of the device 40. Alternatively, the RF electrode assembly 56 may be attached to the device 40 through any suitable type of attachment mechanism (not shown in FIG. 4) as is known in the art.

By suitably changing the distance D1 between the RF electrodes 68A and 68B, the depth of penetration (and also, inter alia, the RF current and RF energy distribution pattern within the skin tissues) of the RF energy into the skin tissues may be varied. For example, increasing the distance D1 may cause the RF currents to penetrate deeper within the skin tissue and to deposit RF energy at a deeper level within the skin, resulting in controlled heating of deeper skin layers or tissues. Decreasing the distance D1 may lead to shallower penetration the RF currents within the skin tissue and to deposit RF energy at a more superficial layers or skin tissues, resulting in controlled heating of shallower or more superficial skin layers or tissues.

An advantage of using the device 40 with the RF electrode assembly 56 is that it may be possible to control and vary the distribution of RF energy into the skin. For example, it may be possible to apply RF energy to shallow or superficial skin tissue(s) or layers by keeping the distance D1 short. Similarly, it may be possible to apply RF energy to deeper skin tissue(s) or layers by keeping the distance D1 long (up to the maximal distance allowable by the dimensions and configuration of the openings 70A and 70B).

In accordance with yet another embodiment of the devices and systems of the present application it may be possible to continuously or discontinuously control the RF energy distribution and the resulting heat distribution within the skin tissues by constantly (continuously) or intermittently changing the distance D1 during the application of the RF electrode assembly 56 to the skin. For example, if one or both of the electrodes 68A and 68B are continuously or intermittently moved within their respective openings 70A and 70B, the heating may continuously or intermittently, respectively, shift between superficial and deeper skin tissue ensuring simultaneous (or at least on the average) heating of both shallow and deeper skin tissues.

It is noted that other different types of RF electrode assemblies with movable electrodes or devices with movable RF electrodes may be constructed and operated, in accordance with other embodiments of the devices and systems of the present application. Additional examples of such devices and their construction and operating methods are described in detail hereinafter (with reference to FIGS. 9A-9C, 10A-10B, 11A-11B, and 12A-12B).

Another type of different RF electrode assembly 76 is also illustrated in FIG. 4. The RF electrode assembly 76 includes electrical contacts 62 which are used to electrically couple any electrical components included in the RF electrode assembly 76 to the electrical components included in the housing 40A of the device 40 as disclosed in detail hereinabove with respect to the RF electrode assembly 56. The contacts 62 may or may not be used also for mechanically attaching the RF electrode assembly 76 to the device 76 as disclosed in detail hereinabove with respect to the RF electrode assembly 56.

The RF electrode assembly 76 also includes four RF electrodes 78A, 78B, 78C and 78D suitably attached to a housing 78 of the. The RF electrodes 78A, 78B, 78C and 78D are not movable laterally with respect to the housing 78 but may be disposed within in suitable openings 80A, 80B, 80C and 80D, formed within the housing 78 such that they may be moved in and out within the openings 80A, 80B, 80C and 80D respectively.

Thus, for example, the RF electrode 78A may be moved within the opening 80A in the directions represented by the double headed arrow labeled 90 which lies along the dashed line 92 representing the longitudinal axis of through the electrode 78A. The remaining RF electrodes 78B, 78C and 78D may be similarly movably disposed within their respective openings 80B, 80C and 80D. Preferably (but not obligatorily), the RF electrodes 78A, 78B, 78C and 78D are spring mounted (the spring is not shown in FIG. 4, but see FIGS. 5 and 6 for a description of such springs) to ensure proper contact with the skin when the device 40 is pressed onto the skin.

Reference is now made to FIGS. 5 and 6. FIG. 5 is an isometric view illustrating an RF electrode assembly having five RF electrodes, in accordance with an embodiment of the present invention. FIG. 6 is an isometric view illustrating an RF electrode assembly having five RF electrodes and a mechanical velocity sensor, in accordance with another embodiment of the RF electrode assemblies of the present application.

The RF electrode assembly 100 has a housing 100A preferably made of a plastic material or a suitable polymer, such as but not limited to, polycarbonate, Delrin®, or any other suitable structural material. The housing 100A is preferably made from an electrically non-conducting material. The housing 100A has five electrically conducting RF electrodes 108A, 108B, 108C, 108D and 108E that are movably disposed within five suitable passages 117) formed in the housing 100A (it is noted that only one of the passages 117 is labeled in FIG. 6 for the sake of clarity of illustration).

The RF electrodes 108A, 108B, 108C, 108D and 108E may be constructed and operative as is known in the art. For example, each of the RF electrodes 108A, 108B, 108C, 108D and 108E may be made of (or may include) an electrically conducting material, such as any suitable metal such as, but not limited to Stainless steel 316, bronze, Aluminum coated by Nickel, and the like. Alternatively, the RF electrodes may be made from a non-electrically conducting material such as a plastic or other polymer based material such as, but not limited to polycarbonate, Delrin®, and the like and the RF electrodes may be made electrically conducting by coating or plating the plastic or other non-electrically conducting electrode part with an appropriate electrically conducting material such as a suitable metal or metallic alloy, including but not limited to a Nickel-Cadmium based alloy, gold, platinum, nickel, or any other suitable electrically conducting material known in the art.

The RF electrode assembly 100 includes five springs 105. Each spring 105 is attached to the housing 100A and to one RF electrode of the RF electrodes 108A, 108B, 108C, 108D and 108E. Each RF electrode of the electrodes 108A, 108B, 108C, 108D and 108E is thus spring-loaded and can move within the passage 117 when the RF electrode is pressed against the skin 109. The RF electrode assembly 100 has an additional passage 107 formed therein. The passage 107 may be used for holding a sensor therein (see FIG. 6). Each of the electrodes 108A, 108B, 108C, 108D and 108E is suitably attached to a (preferably isolated) electrically conducting wire (the wires are not shown for the sake of clarity of illustration) for applying RF energy to the RF electrode. The electrically conducting wires may be connected to an RF energy generating unit (not shown in FIGS. 5-6) which may be included in the device to which the RF electrode assembly is attached (the entire device is not shown in FIGS. 5-6 for the sake of clarity of illustration but may be similar to the device 40 of FIG. 4, or to the hand-held unit 36 of the device 30 of FIG. 3).

When the RF electrode assembly 100 is pressed onto the skin, the RF electrodes 108A, 108B, 108C, 108D and 108E or at least some of them move within the openings 117 and firmly contact the skin 109 due to their being spring-loaded. The arrangement and spring mounting of the electrodes advantageously contribute to the ability of the individual electrodes 108A, 108B, 108C, 108D and 108E to follow the contours of the skin and to firmly make contact with the skin even when applied to substantially non planar skin regions, such as certain regions of the face, hands, feet or other body parts and enable the applying of RF currents to the skin 109 through two or more electrodes of the electrodes 108A, 108B, 108C, 108D and 108E.

Turning to FIG. 6, the RF electrode assembly 120 is similar to the RF electrode assembly 100, except that the RF electrode assembly 120 also includes a velocity sensor 114. The velocity sensor 114 includes a rotatable member 110 which is rotatably attached within the passage 107 of the housing 100A. The rotatable member 110 is rotatably coupled to a transducer 112. The transducer 112 may be any type of rotation sensing transducer known in the art. For example, the transducer 112 may be implemented as a small electrical motor capable of functioning as an alternator or dynamo when its rotor (not shown) is rotated. When the rotatable member 110 is rotated by being rolled along the skin, the motor will output an electrical signal indicative of the speed of rotation of the shaft of the electrical motor. This signal may be output by suitable electrical conductors to any type of electrical circuitry (not shown in FIG. 5-6) for processing. The processing may provide a signal or data indicative of the velocity of movement of the RF electrode assembly 120 along the skin.

In operation, when the RF electrode assembly 100 is pressed down on the skin, the RF electrodes 108A, 108B, 108C, 108D and 108E or at some of the electrode move inside the openings 117 of the housing 100A and the rotatable member 110 touches the skin 109. In this position, the operator of the system or device moves the RF electrode assembly 100 along the surface of the skin 109 and the rotatable member 110 rotates. The rotatable member 110 is coupled to the transducer 112 via a transmission mechanism 115. Thus, when the RF electrode assembly 120 is moved along the skin the electrical signal produced by the transducer 112 is proportional to the speed of movement of the rotatable member over the skin.

When the velocity of the RF electrode assembly 120 relative to the treated skin (not shown) is less than a preset or predetermined (or optionally factory preset) threshold value, the application of power to the RF electrodes 108A, 108B, 108C, 108D and 108E may be stopped. This (optional) feature is an advantageous safety feature ensuring that if some of the RF electrodes 108A, 108B, 108C, 108D and 108E are left in contact with the skin while the device is stationary or moves too slowly with respect to the skin, the application of RF energy to the skin is interrupted to avoid excessive heating and/or burning of the skin.

In accordance with other embodiments of the devices and systems of the present application, the velocity sensor 114 need not obligatorily be implemented as a mechanical sensor of the particular exemplary sensor illustrated in FIG. 6. Rather, the sensor or sensors (if more than one velocity sensor is used) may be any sensor(s) suitable for detecting the speed of motion (velocity) of the applicator unit (such as the applicator unit 6 of FIGS. 1-2) or of the RF electrode assembly unit (such as, but not limited to the RF electrode units 46 and 120 of FIGS. 4 and 6, respectively) along the skin. It is noted that methods and sensors for determining the velocity or speed of movement of an applicator or a device or part of a device relative to the skin are well known in the art, are not the subject matter of the present application and are therefore not disclosed in detail hereinafter. For example, methods and devices for such velocity determination may be implemented using a mechanical gyro (see, for example U.S. Pat. No. 5,296,794), an optical gyro (see, for example U.S. Pat. No. 4,514,088, incorporated herein by reference in its entirety), an optical mouse (see, for example U.S. Pat. Nos. 4,631,400 and 4,920,260, incorporated herein by reference in their entirety), other mechanical systems such as encoders (see, for example U.S. Pat. Nos. 5,235,514, and 5,208,521, incorporated herein by reference in their entirety).

However, it is noted that other suitable types of sensors and velocity determining methods known in the art may be used for performing the velocity determination of the devices of the present application and may be easily adapted for use in the devices and systems of the present application by those skilled in the art.

Typically, when the sensor(s) 2 of the devices 10 and 20 (FIGS. 1-2) include velocity sensors, the velocity sensors may be suitably coupled to an (optional) speed determining unit (not shown) included in the main unit (of FIG. 3) or in a hand-held device (such as, but not limited to, the device 40 of FIG. 4). The speed determining unit may receive signals from one or more of the sensor(s) 2 or 52 or 114 (of FIGS. 1-2, 4 and 6, respectively) and may process the signals to determine the speed of movement (velocity) of the applicator unit 6 or the RF electrode assemblies 46 or 120 relative to the skin. If the measured speed of movement of the hand-held device 40 relative to the skin is lower than a preset or predetermined speed threshold value, the supply of current to the RF electrodes of the applicator unit or the RF electrode assembly unit(s) may be interrupted to avoid excessive heating of the skin by RF energy in a slow moving or stationary hand held device, or applicator or electrode assembly unit. The speed determining unit (not shown) may be implemented as a separate electrical circuit (not shown) coupled to the controller unit 8 (FIGS. 1-2) or may also be coupled to the power source 12 or 22 (of FIGS. 1 and 2 respectively) or to the battery 42 (of FIG. 4) to control the application of electrical current from the power source to the RF generating unit 4 or to the RF electrodes of the device.

In accordance with another embodiment of the devices of the present application, the signals from the velocity sensor(s) may be processed by the controller unit 8, with or without being suitably conditioned by suitable electrical circuitry included in the skin treating device(s). Thus, the velocity determining unit may be implemented entirely or partially as part of the controller unit 8 and may be implemented within the controller unit 8 by suitable hardware or software or by a suitable combination of hardware and software, as is known in the art.

It is noted that in accordance with additional embodiments of the devices of the present application, other different safety devices and features may be included in the various devices and systems of the present application.

A common problem encountered when RF electrodes are used to heat the skin by delivering RF energy to the skin is that the electrical coupling of the RF electrodes to the skin may not always be optimal. For example, if some of the RF electrodes are not well coupled electrically to the underlying skin, sparking may occur between the RF electrodes and the skin which may be undesirable due to the increased possibility of burning of the skin. Therefore, in accordance with an embodiment of the devices and systems of the present application, a safety mechanism may (optionally) be included in the systems or devices to ensure proper electrical coupling of the RF electrodes to the skin during the delivery of RF currents to the skin. For example a micro-switch may be attached to the housing of the applicator or RF electrode assembly below the RF electrode if the micro-switch is open the controller switches the application of the RF energy only to those RF electrodes with closed micro switch. The micro switch may be attached to the device in such a way that when the RF electrode starts to detach from the skin and is moving outward from the housing, the micro-switch opens before the RF electrode losses contact with the skin and the controller already switches off the RF power to this particular electrode before the RF electrode actually detaches from the skin to prevent sparking.

Figure 7A:
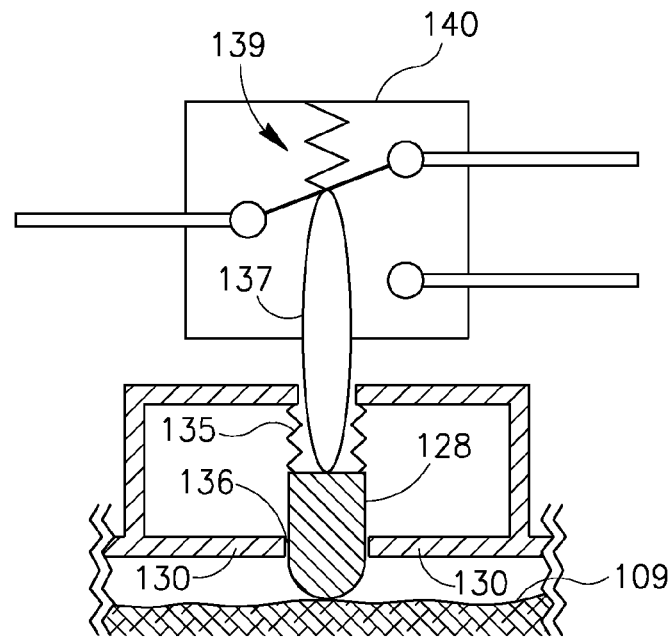
FIGS. 7A and 7B are schematic part cross-sectional diagrams illustrating two different positions of an RF electrode and an associated switching device, included in an embodiment of the skin treatment device.
Figure 7B:
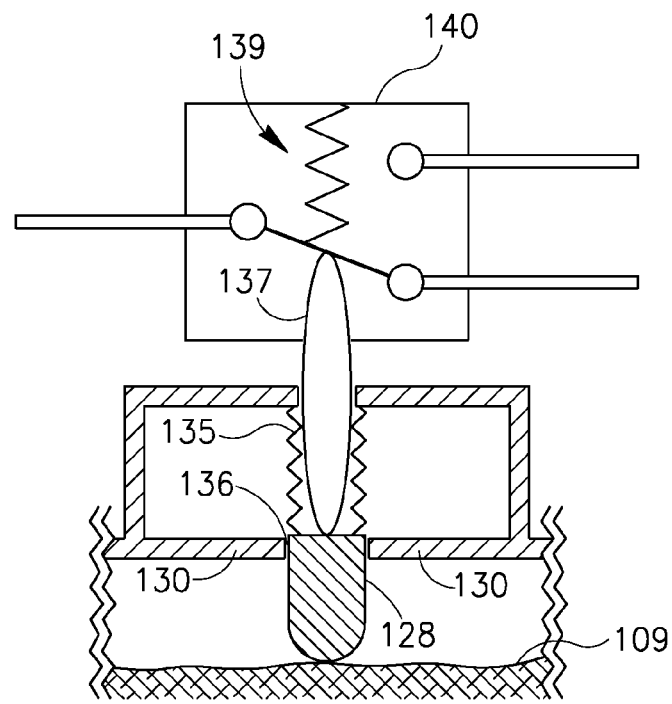

Reference is now made to FIGS. 7A and 7B which are a schematic part cross-sectional diagrams illustrating two different positions of an RF electrode and an associated switching device, included in a skin treatment device in accordance with another embodiment of the devices of the present application.

Turning to FIG. 7A, an RF electrode 128 is shown disposed within an opening 136 formed in the housing 130 of a skin treatment device (the device is not shown in its entirety) or part thereof (only part of the housing 130 is shown in FIGS. 7A and 7B for the sake of clarity of illustration). The RF electrode 128 is mechanically coupled to a coupling member 137 which is coupled to a switching element 139 of a micro-switch 140. The RF electrode 128 is also attached to a spring 135 which is also attached to another part of the housing 130.

In FIG. 7A, the housing 130 is shown as pressed against the skin 109. The RF electrode 128 is in good contact with the skin 109 and has moved within the opening 136, pushed against the spring 135 such that the coupling member 137 has pushed the switching element 139 of the micro-switch 140 to the closed position allowing the application of RF energy to the RF electrode 128 and through the RF electrode 128 and another electrode to the skin 109 (It is noted that the second RF electrode required for completing the circuit in a bipolar RF electrode configuration is not shown in FIGS. 7A and 7B for the sake of clarity of illustration)

As illustrated in FIG. 7B, when the housing 130 is lifted in a direction off the skin 109, the contracted spring 135 pushes against the RF electrode 128 and expands. The coupling member 137 is pulled in a direction toward the skin 109 by the spring 135 and by the RF electrode 128 coupled to the spring 135 and switches the switching element 139 of the micro-switch 140 to the open position turning off the application of RF energy to the RF electrode 128 even before the electrode 128 detaches from the skin.

It is noted that the micro-switch 140 as operated herein is actually a contact detecting sensor unit which detects whether the electrode 128 is or is not in contact with the skin 109.

Preferably, the micro-switch 140 is of the non-latching type that requires constant pushing of the coupling member 137 in order to remain in the closed position. This arrangement advantageously ensures that the RF current application to any RF electrode which is not in good contact with the skin 109 or that has traveled a predetermined or preset distance outward (in a direction towards the skin 109) is safely interrupted before any sparking can occur. However, any other different suitable switching arrangements and switching devices of any type known in the art may be used to implement the anti-sparking safety feature described herein, as will be easily implemented by those skilled in the art.

It is noted that the anti-sparking switching device 140 is given by way of example and that the type, structure and mode of operation of the switching device may be varied as will be easily apparent to those skilled in the art. For example, the position of the RF electrode 128 may be monitored by any type of sensor(s), such as but not limited to optical sensor(s), electro-optical sensor(s), electromagnetic sensor(s), or any other sensor(s) known in the art, and the output of the sensor(s) may be used for activating the switch 140 or any other switching device used in the device. Similarly, any type of suitable switching device known in the art may be used to instead of the micro-switch 140 for implementing the anti-sparking safety device of the various different embodiments of the devices and systems of the present application.

Reference is now made to FIGS. 8A-8F which are schematic diagrams pictorially illustrating different steps of a method of operation of a skin treatment device using electrode pair and/or electrode group switching, in accordance with an embodiment of the devices of the present application.

Figure 8A:
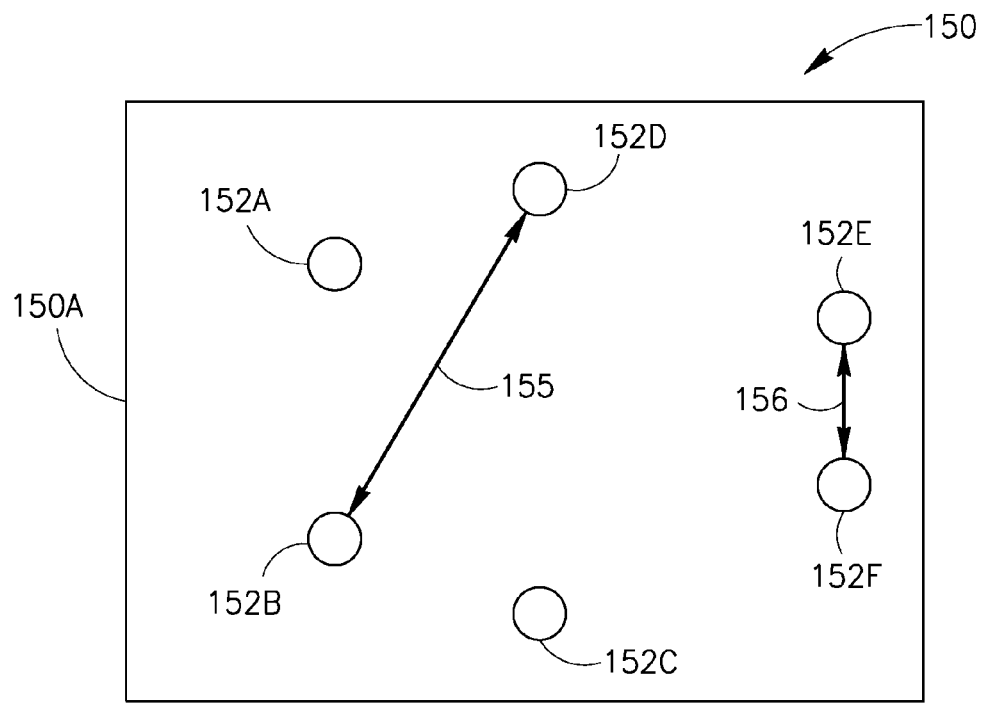
FIGS. 8A-8F are top schematic diagrams illustrating different steps of a method of operation of a skin treatment device using electrode pair and/or electrode group switching, in accordance with an embodiment of a method of skin treatment.

FIG. 8A schematically illustrates the arrangement of six electrodes 152A, 152B, 152C, 152D, 152E and 152F disposed in a housing 150A of a skin treatment device 150.

It is noted that for the sake of clarity, only the part of the housing 150A including the electrodes is shown. The RF electrodes 152A, 152B, 152C, 152D, 152E and 152F may be, but are not limited to RF electrodes of any suitable type as disclosed hereinabove and illustrated in the drawings and known in the art.

In operation of the device 150, a controller of the device 150 (such as, but not limited to, the controller 8 of FIGS. 1-2, or any other suitable type of controller and/or switching device) controls the application of RF currents to selected pairs of RF electrodes. For example, in FIG. 8A, RF currents are simultaneously applied to the skin by the pair of RF electrodes 152B, 152D and by the pair of electrodes 152E, 152F. The application of RF currents is schematically indicated by a double headed arrow connecting the RF electrodes of a selected pair of RF electrodes. For example, the double headed arrow 155 schematically indicates that RF currents are being applied to the skin through the RF electrodes 152B and 152D and the double headed arrow 156 schematically indicates that RF currents are being applied to the skin through the RF electrodes 152E and 152F.

It is noted that during RF current application, in each activated pair of electrodes one RF electrode of the pair operates as an anode and the second RF electrode of the pair operates as a cathode, depending on the polarity of the electrical potential applied to the electrodes of the pair. Thus, when the RF electrode pairs 152B, 152D and 152E, 152F are simultaneously operated to apply RF currents to the skin, an RF current will also flow between the anode of the pair 152B, 152D and the cathode of the pair 152E, 152F. Similarly, an RF current will also simultaneously flow between the cathode of the pair 152B, 152D and the anode of the pair 152E, 152F.

Figure 8B:
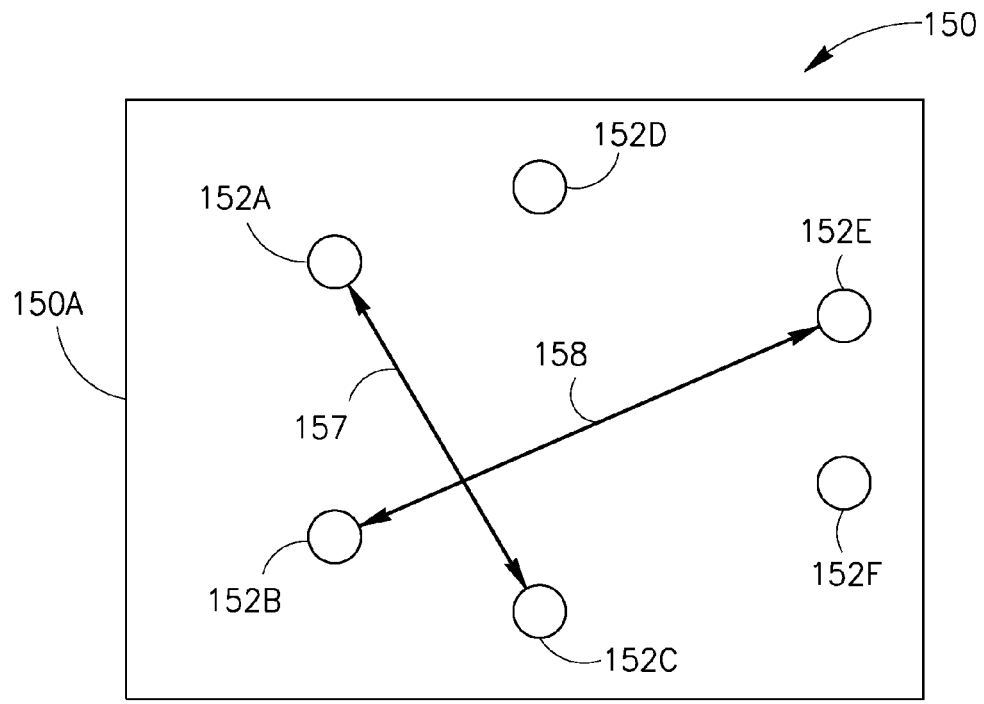

After RF currents have been applied to the skin through the electrode pairs 152B, 152D and 152E, 152F for a first time period, the controller or switching device included in the device 150 may terminate the application of RF currents through the RF electrode pairs 152B, 152D and 152E, 152F and may begin to apply RF currents to the skin through the electrode pair 152A, 152C and 152B, 152E, as is schematically indicated in FIG. 8B by the double headed arrows 157 and 158, respectively for the duration of a second period of time. It is noted that during the second time period no current is applied to the skin through the electrodes 152D and 152F (which were heated by the RF currents during the first time period), allowing these electrodes to cool during the entire duration of the second time period and avoids or reduces overheating of the electrodes 152D and 152F.

Figure 8C:
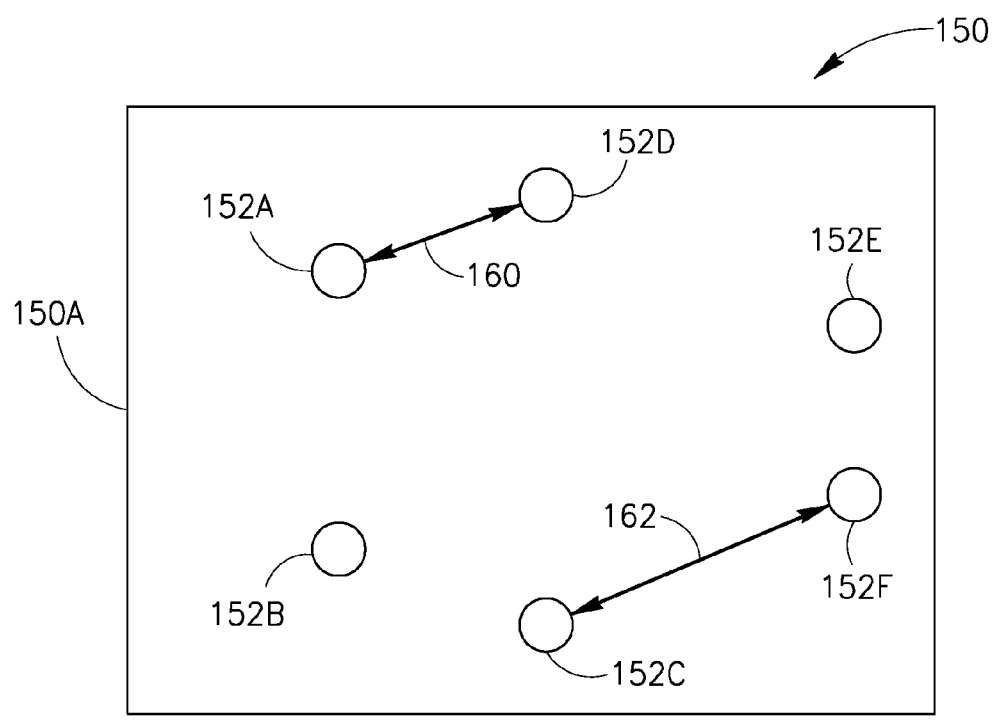

After RF currents have been applied to the skin through the electrode pairs 152A, 152C and 152B, 152E for the second time period, the controller or switching device included in the device 150 may terminate the application of RF currents through the RF electrode pairs 152A, 152C and 152B, 152E, and may begin to apply RF currents to the skin through the electrode pair 152A, 152D and 152C, 152F, as is schematically indicated in FIG. 8C by the double headed arrows 160 and 162, respectively for the duration of a third period of time. It is noted that during the third period of time no current is applied to the skin through the electrodes 152B and 152E (which were heated by the RF currents during the second time period), allowing these electrodes to cool during the entire duration of the third time period and avoids or reduces overheating of the electrodes 152B and 152E.

Figure 8D:
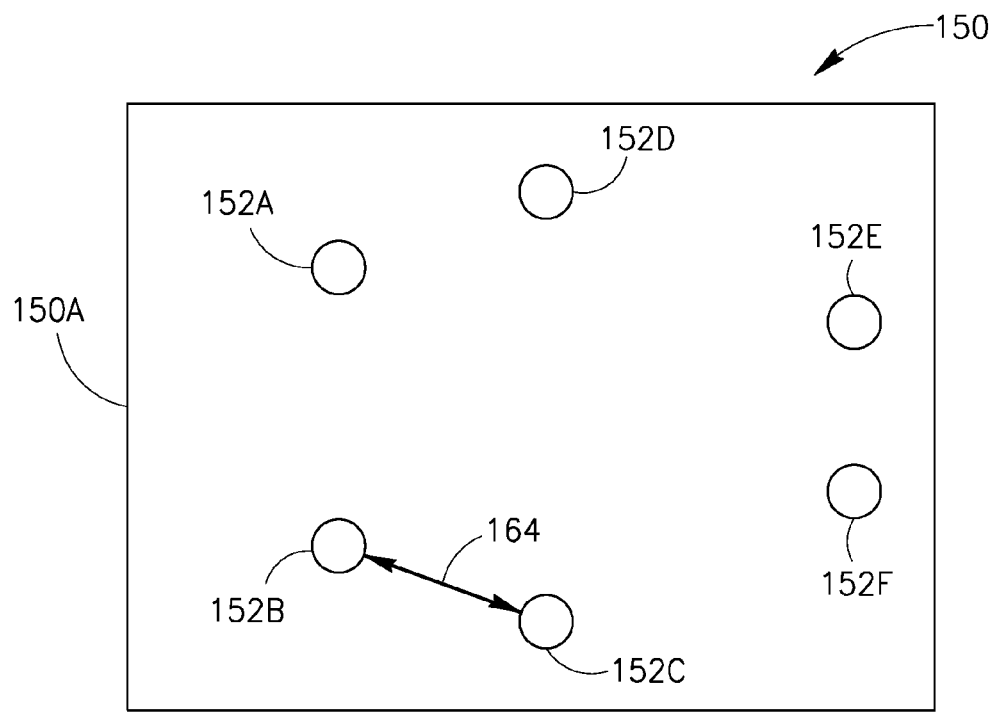

After RF currents have been applied to the skin through the electrode pairs 152A, 152D and 152C, 152F for the third time period, the controller or switching device included in the device 150 may terminate the application of RF currents through the RF electrode pairs 152A, 152D and 152C, 152F, and may begin to apply RF currents to the skin through the single electrode pair 152B, 152C for the duration of a fourth period of time as is schematically indicated by the double headed arrow 164 of FIG. 8D. It is noted that during the fourth period of time no current is applied to the skin through the electrodes 152A, 152D, 152E and 152F (which were heated by the RF currents during some of the previously described time periods), allowing these electrodes to cool during the entire duration of the fourth time period to avoid or reduce electrode overheating.

Figure 8E:
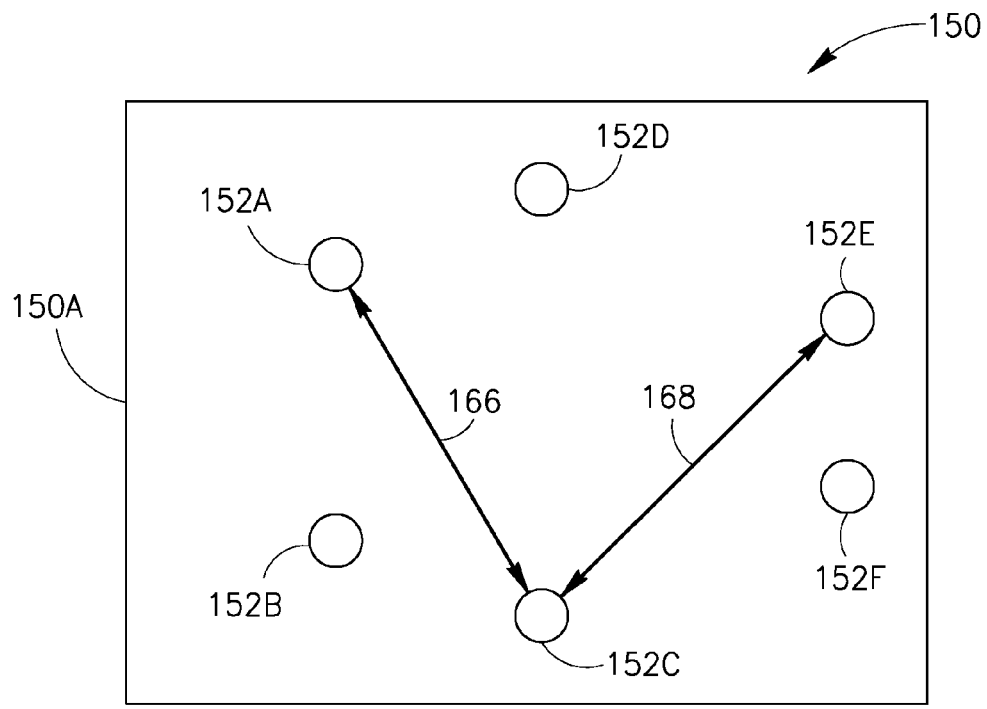

After RF currents have been applied to the skin through the single electrode pair 152B, 152C for the fourth time period, the controller or switching device included in the device 150 may terminate the application of RF currents through the RF single electrode pair 152B, 152C and may begin to apply RF currents to the skin through the electrode triplet 152A, 152C and 152E for the duration of a fifth period of time as is schematically indicated by the double headed arrows 166 and 168 of FIG. 8E. It is noted that when using the electrode triplet 152A, 152C and 152E to apply RF currents to the skin (such an electrode configuration is referred to as a tripolar electrode configuration hereinafter) any single electrode from the triplet 152A, 152C and 152E may be selected as the cathode while the remaining two electrodes are used as the anodes. Conversely, it may be possible to use any single electrode selected from the triplet 152A, 152C and 152E as the anode while the remaining two electrodes are used as the cathodes.

Figure 8F:
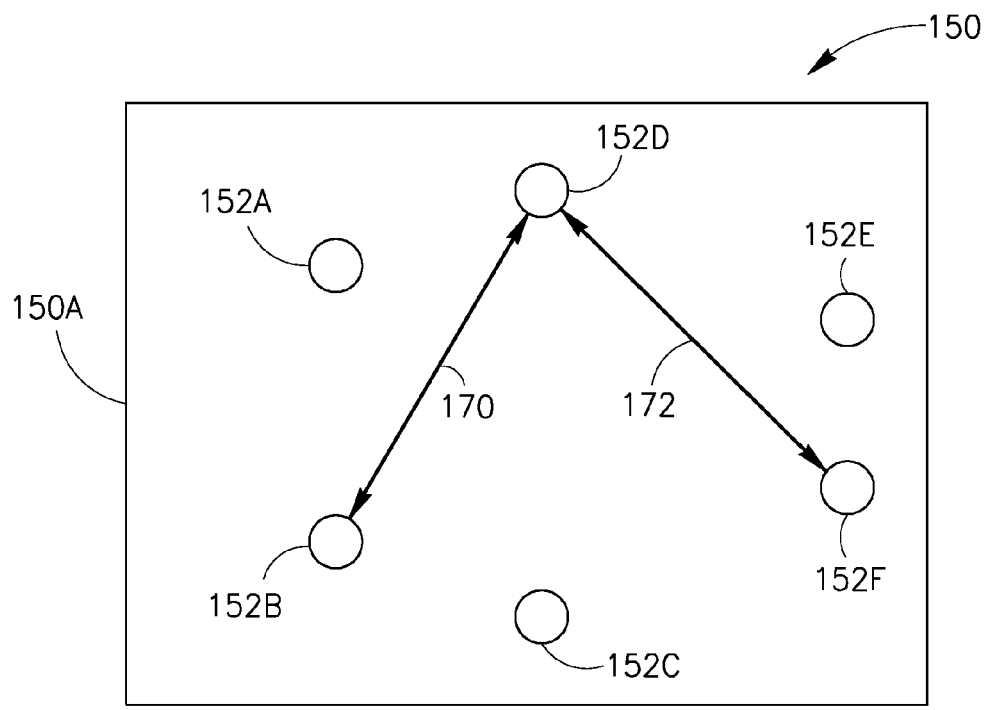

After RF currents have been applied to the skin through the electrode triplet 152A, 152C and 152E for the fifth time period, the controller or switching device included in the device 150 may terminate the application of RF currents through the electrode triplet 152A, 152C and 152E and may begin to apply RF currents to the skin through the electrode triplet 152B, 152D and 152F for the duration of a sixth period of time as is schematically indicated by the double headed arrows 170 and 172 of FIG. 8F. It is noted that when using the electrode triplet 152A, 152C and 152E to apply RF currents to the skin, any single electrode from the triplet 152B, 152D and 152F may be selected as the cathode while the remaining two electrodes are used as the anodes.

Conversely, it may be possible to use any single electrode selected from the triplet 152B, 152D and 152F as the anode while the remaining two electrodes are used as the cathodes. It is also noted that during the sixth period of time no current is applied to the skin through the electrode triplet 152A, 152C and 152E (which were heated by the RF currents during some of the previously described time periods), allowing these electrodes to cool during the entire duration of the sixth time period to avoid or reduce electrode overheating.

It will be appreciated by those skilled in the art that the principle demonstrated hereinabove for electrode pair switching and electrode triplet switching may be extended to any number and any grouping of electrodes. Thus it may be possible to group electrodes into groups including any desired number N of electrodes (wherein N is a positive integer number equal to or greater than 2) and switch between any selected number of such electrode groups or combinations (provided that there is a sufficient number of RF electrodes in the device to enable the electrode group switching to achieve reasonable cooling for non-activated electrodes).

The above disclosed exemplary electrode pair or electrode group switching may continue as described above as long as the device 150 is active (turned on) and some of the RF electrodes are in contact with the skin. The switching of electrode pairs may continue by activating (applying RF currents through) any suitable electrode pair or any suitable combination of electrode pairs (or electrode groups) within the duration of set time periods as described above in the non-limiting examples illustrated in FIGS. 8A-8D.

It is noted that the above described switching between different groups or different pairs of RF electrodes may be implemented in the devices and electrode assemblies of the present application using different types of hardware implementations. In accordance with one possible implementation, the controller used in the device (such as but not limited to the controller unit 8 of FIGS. 1-2) may perform the electrode group switching. However, since the RF power delivered through the RF electrodes may be considerable, the devices and/or electrode assemblies may have to include one or more switching units (not shown) which may be connected between the controller unit 8 (or any other controller type used in the device) and the RF electrodes.

For example, such controllable switching unit(s) may be implemented as part of the controller unit 8 in devices having fixed electrode assemblies (such as, but not limited to the applicator 36 of FIG. 3) or within the housing 40A of the hand-held device 40 (of FIG. 4) However, such controllable switching unit(s) may be implemented, in accordance with another different embodiment of the devices of the present application, as separate independent switching unit(s) which may be included in the detachable electrode assemblies (such as, but not limited to the detachable and/or disposable electrode assemblies 46, 56 and 76 (of FIG. 4) or in hand-held applicators (such as but not limited to the applicator 36 (of FIG. 3). The construction and operation of such switching devices in the RF range is well known in the art, is not the subject matter of present application and is therefore not disclosed in detail hereinafter.

In operation, when switching pairs of electrodes or groups of electrodes, the controller unit 8 (or any other type of controller unit used in implementing the device) of the device may switch off the RF current for a short period of time (typically, but not obligatorily, for a fraction of a second) and then the switching unit (not shown) may switch to the next pair or next group of electrodes in order to prevent sparking in the switching unit. After switching to the next pair or group of electrodes, the controller 8 (or any other type of controller unit used in implementing the device) may switch on the RF current to activate the new electrodes pair or new electrode group.

It will be appreciated by those skilled in the art that the RF electrode pair (and/or RF electrode group) switching method may operate in many modes and variations which are not limited to the examples disclosed hereinabove and illustrated in FIGS. 8A-8D.

In accordance with an embodiment of the method of the present application, the time periods during which different electrode pairs or different electrode pair (or electrode group) combinations are activated may all have an equal duration.

In accordance with yet another embodiment of the electrode switching method, the time periods during which different electrode pairs or different electrode pair combinations are activated may have different non-equal durations.

In accordance with yet another embodiment of the electrode switching method, the time periods during which different electrode pairs or different electrode pair combinations are activated may be separated by time periods during which no RF currents are applied to the skin.

In accordance with still another embodiment of the electrode switching method, the time periods during which different electrode pairs or different electrode pair combinations are activated may be contiguous such that a pair of electrodes or a combination of electrode pairs start delivering RF currents to the skin immediately after the previously active electrode pair or combination of electrode pairs stopped delivering RF currents to the skin.

In accordance with yet another embodiment of the electrode switching method, the time periods during which different electrode pairs or different electrode pair combinations are activated may temporally overlap.

It is noted that the electrode switching (and/or electrode pair switching) methods disclosed hereinabove may be automatically performed by the devices and systems of the present application. For example, the controller unit 8 of FIGS. 1-2 may be programmed to perform any desired electrode pair switching sequence automatically when the device 10 or 20 is activated for delivering RF currents to the skin.

It will be appreciated by those skilled in the art that any type of electrode pair switching sequence may be programmed into the devices of the present application. For example, in accordance with one embodiment of the devices and systems of the present application, the controller unit 8 may be programmed or configured for repeating a specific pre-set or pre-programmed sequence of electrode pair activations as long as the device is turned on and the various safety mechanisms included in the device allow the passing of RF currents to the skin.

In accordance with another embodiment of the skin treating device, the controller unit 8 may be programmed or configured for using a random or a pseudo-random sequence of electrode pair activations as long as the device is turned on and the various safety mechanisms included in the device permit or allow the passing of RF currents to the skin.

In accordance with still another embodiment of the skin treating device, the electrode pair switching and/or the Electrode group switching of the devices and systems may be automatically controlled by the controller unit of the device (such as, but not limited to the controller unit(s) 8 and 13 of FIGS. 1-2, and 14-16, respectively), based on the results of sensing the temperature of one or more of the RF electrodes. For example, in embodiments of the skin treating devices (such as, but not limited to, the devices 10, 20, 280, 300 and 320) which include temperature sensors configured for sensing the temperature of any of the RF electrodes included in the device (either by being attached to or embedded within the RF electrode, or by sensing IR radiation emitted by the RF electrode, or by implementing any other method or sensor type for sensing the temperature of one or more RF electrodes, as is known in the art), The controller of the device may continuously or intermittently determine the temperature of one or more RF electrodes of the device by suitably processing the signals received from such temperature sensors. If the temperature of an RF electrode included in an RF electrode pair or RF electrode group exceeds a threshold value, the controller unit of the device may stop the application of RF energy to the Electrode pair or Electrode group which contains the "hot" RF electrode and may switch on the application of RF energy to another RF electrode pair or another RT electrode group having a temperature which does not exceed the temperature threshold. The RF electrode pair or group which is switched-on may be randomly selected or, alternatively, may be selected according to a pre-programmed or preset sequence stored in a memory device connected to the controller (not shown) or in a program operating on the controller. Thus, by automatically switching off the RF power top electrode pairs or electrode groups including an RF electrode having a temperature exceeding a safety temperature threshold value, the device ensures that the skin of the treated patient or subject will not be damaged by excessive heating of the skin by the RF electrode(s).

Figure 14:
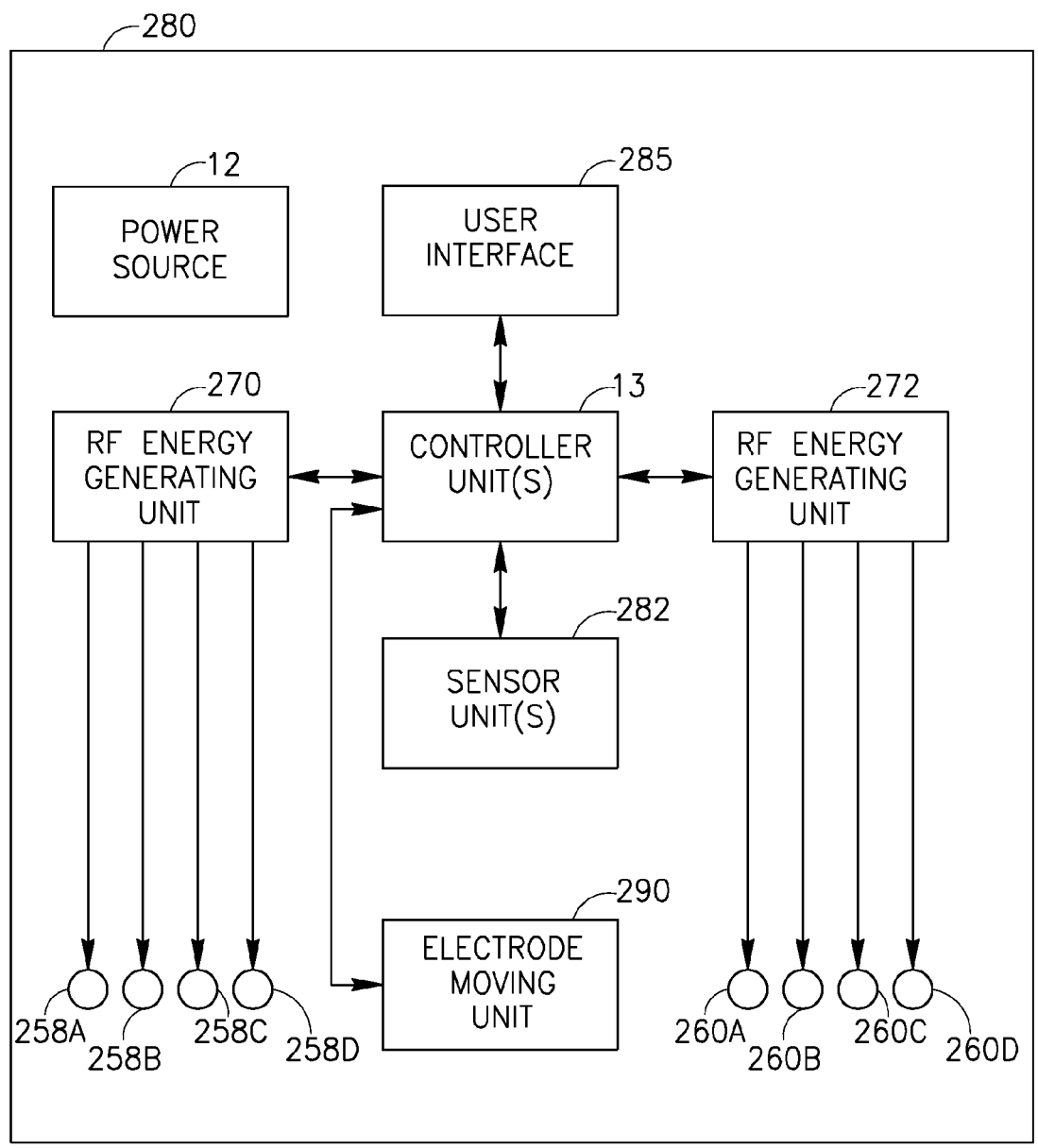
FIG. 14 is a schematic block diagram illustrating the components of a device for skin treatment, having two RF energy generating unit in accordance with an embodiment of the skin treating device.
Figure 15:
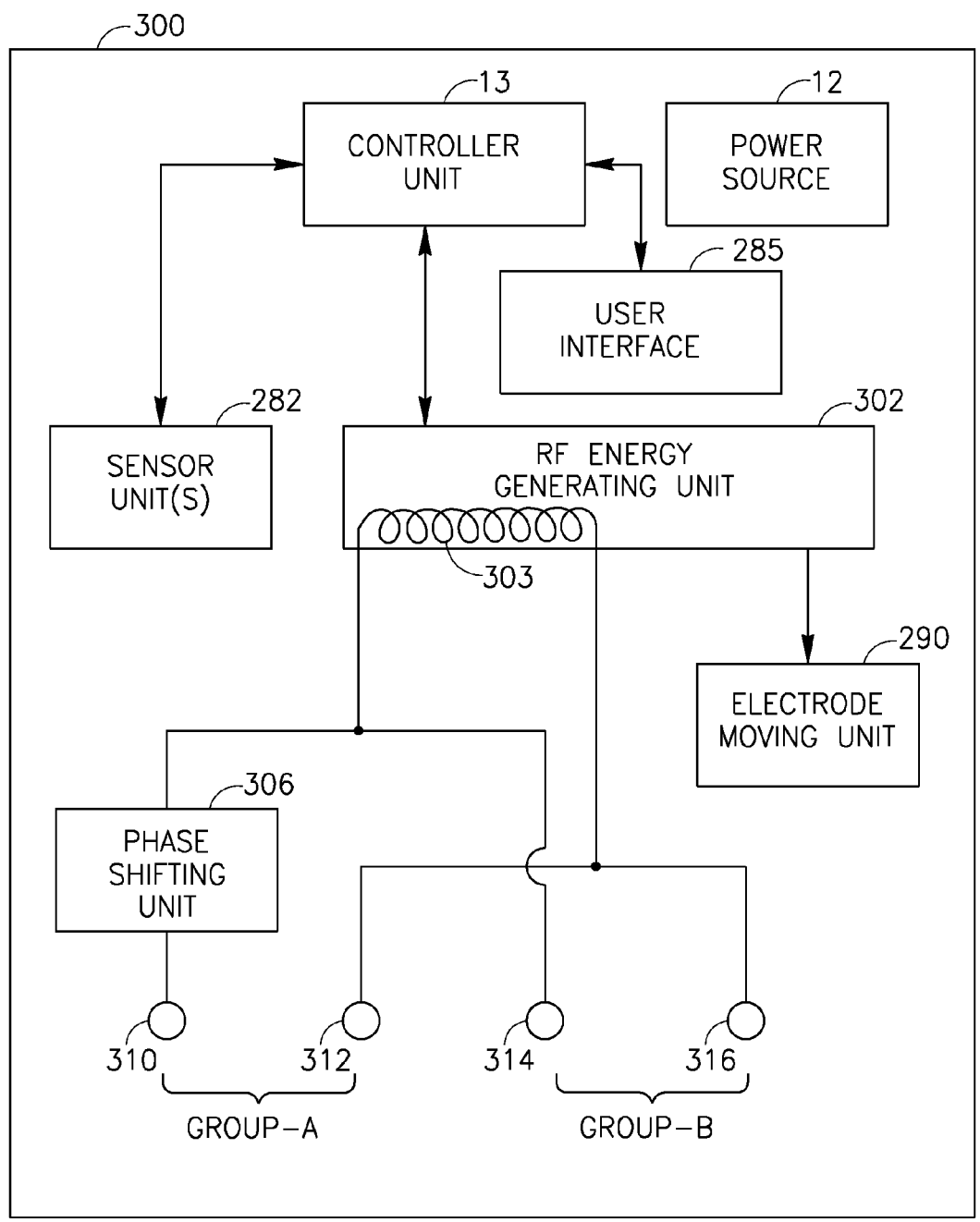
FIG. 15 is a schematic block diagram illustrating the components of a skin treating device including a single RF energy generating unit, a phase shifting unit and two RF electrode groups.
Figure 16:
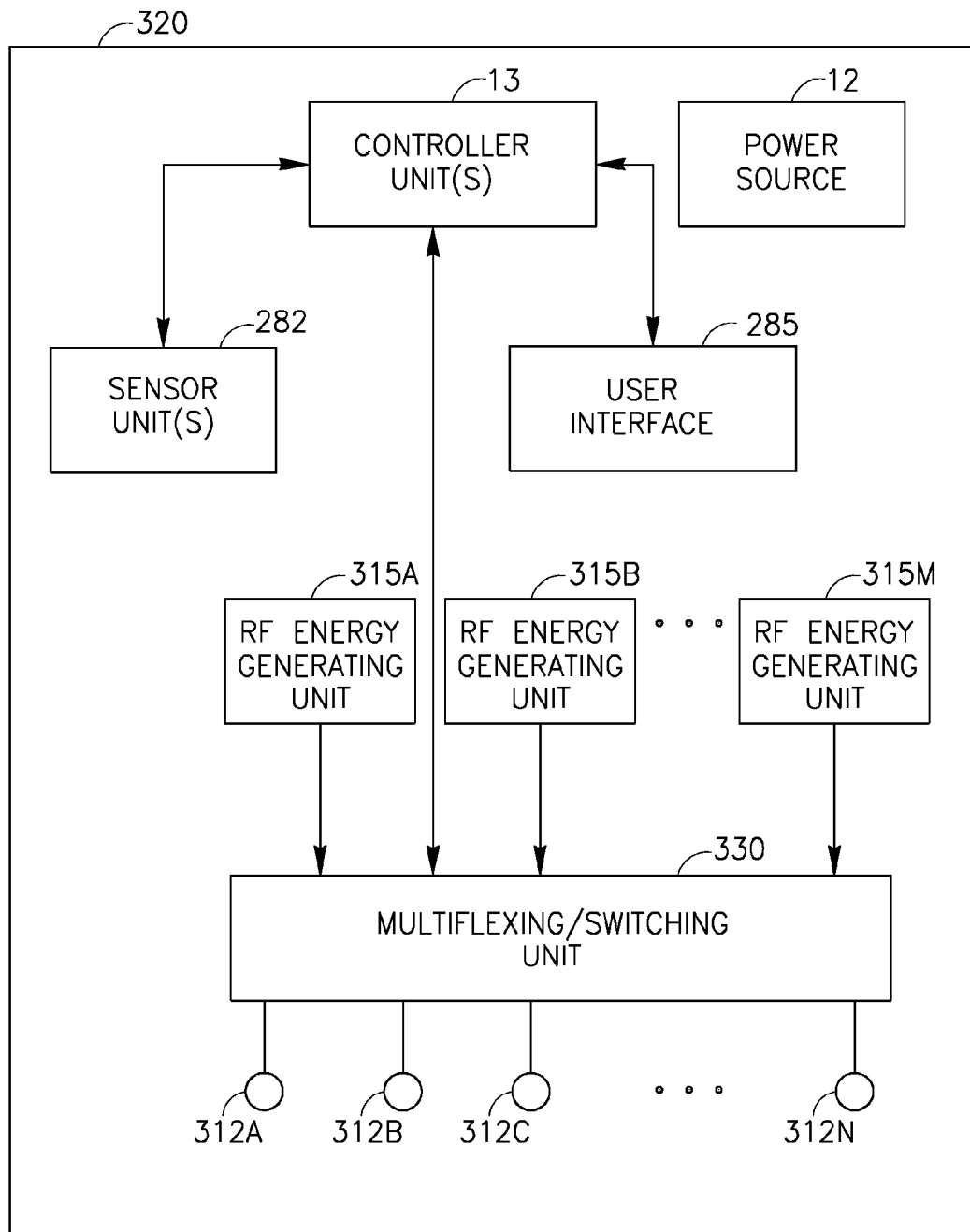
FIG. 16 is a schematic block diagram illustrating the components of a skin treatment device having a plurality of RF energy generating units controllably connectable to a plurality of RF electrodes.

Such an safety electrode temperature threshold is preferably preset at the factory, but may also possibly be set or programmed by the user (for example, by using one of the dials 9 of the system 30 of FIG. 3 or the user interface 285 of FIGS. 14-16).

The RF electrode pair or group including the "hot" RF electrode which has been switched off, is thus allowed to cool down such that its temperature is below the safety threshold value. In accordance with one possible embodiment of this automatic switching method, the RF electrode pair or group including such a "hot" RF electrode is not reintroduced into the group of safely activatable RF electrode pairs or groups until the temperature of the "hot" RF electrode is below the safety threshold value.

In accordance with another possible embodiment of the automatic switching method, the RF electrode pair or group including such a "hot" RF electrode is not reintroduced into the group of safely activatable RF electrode pairs or groups until the temperature of the "hot" RF electrode is below another preset or user settable second threshold value which is substantially lower than the safety threshold value. This may advantageously ensure that RF electrode pairs or RF electrode groups which have not had sufficient time to cool to a temperature substantially below the safety threshold value will not be reactivated (will not be switched on) before it had enough time to cool to a temperature ensuring a sufficiently long period of RF energy delivery to the skin before the pair heats up again to a temperature exceeding the safety threshold value.

In accordance with yet another embodiment of the skin treating device, the controller unit 8 may be programmed or configured such that it may be switched between various different predetermined modes of operation. For example, any of the devices disclosed hereinabove may be configured such that the user of the device may change the mode of operation by choosing a mode of operation selected from a set of available operational modes of the device. Such modes of operation may include but are not limited to, the use of repeated pre-programmed sequences of electrode pair activation, the use of random or a pseudo-random sequences of electrode pair activations, the use of electrode activation sequences having varying predetermined electrode activation times (duty cycles), and the like.

Those skilled in the art will appreciate that many different variations of RF current application regimes and/or modes and/or sequences may be used in implementing the devices and systems of the present application by varying or modifying one or more parameters of the applied RF currents, including but not limited to, RF current intensity, pulsed RF current duty cycle, RF current frequency, RF current application duration, the number and configuration of electrodes or electrode pairs or electrode-pair combinations being used, and any desired or useful combinations of these parameters. All such different modes and variations are considered to be usable in the devices and systems of the present application.

It is further noted that, in accordance with other embodiments of the devices and systems disclosed herein, the shape, size, composition and geometrical arrangement of the RF electrodes of the skin treating devices disclosed hereinabove may be varied to adapt the device for a specific application. Thus, while the RF electrodes used in devices 40, 100, 120 are of equal size and shape, it may be possible, in accordance with another embodiment of the devices and systems disclosed herein to use within the same device or the same RF electrode assembly, RF electrodes having different size and shape. The shape and size of different RF electrodes of devices having different RF electrode sizes may depend, inter alia, on the current intensity needed, the electrode arrangement of the device, the particular region of skin to be treated, the available electrode pair combinations and/or tripolar electrode configurations and other various engineering or practical considerations.

Similarly, the electrode arrangements disclosed hereinabove and illustrated in the drawing figures are given by way of example only and any other desired geometrical arrangement of RF electrodes may be used for implementing the devices, systems and electrode assemblies of the present invention.

It is noted that the exact current paths and current density distribution through the treated skin region may depend, inter alia, on the number of active electrodes, on the electrode polarity (the selection of anode and cathode of each activated electrode pair) of the simultaneously operating electrode pairs, on the skin resistance to the applied current and the precise geometry of the selected electrode pairs which are being simultaneously operated.

It will be appreciated, that the type of electrode assembly with movable RF electrodes disclosed hereinabove is not limited to having two movable electrodes as illustrated in the exemplary electrode assembly 56 of FIG. 4. Rather, in accordance with additional embodiments of the invention, a variety of different types and configurations of devices and/or electrode assemblies having different types, numbers and configurations of movable electrodes may be implemented and used.

Figure 9A:
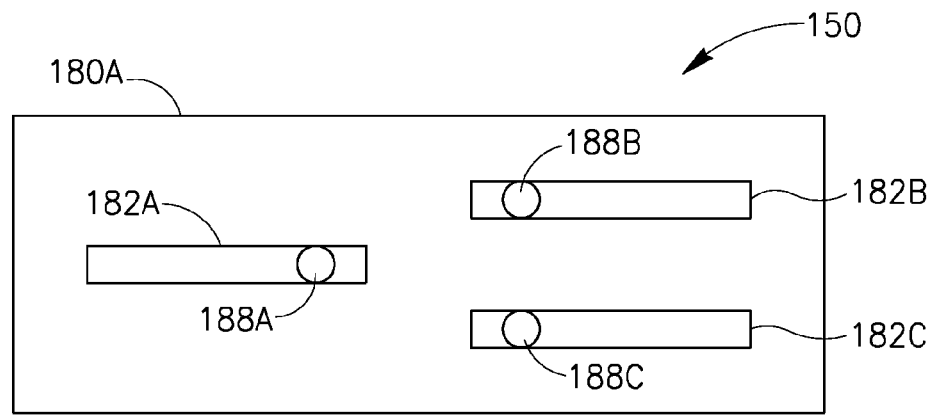
FIGS. 9A-9C are schematic diagrams illustrating top views of three different possible RF electrode configurations of a device having three controllably movable RF electrodes, in accordance with an additional embodiment of the skin treating device.
Figure 9B:
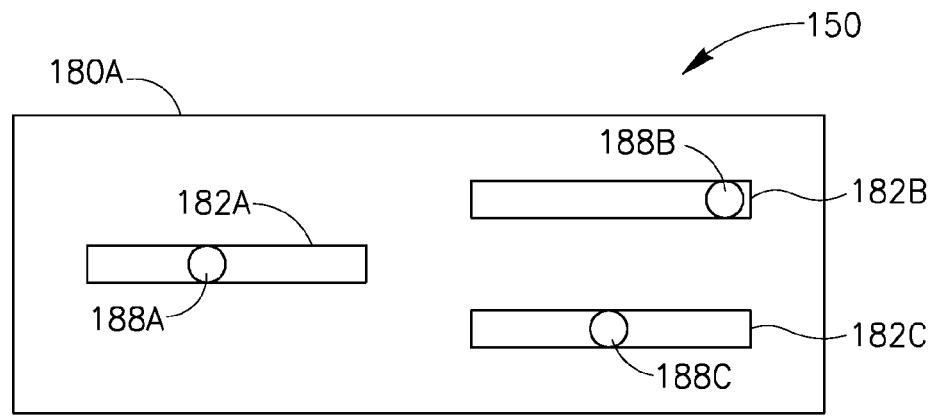
Figure 9C:
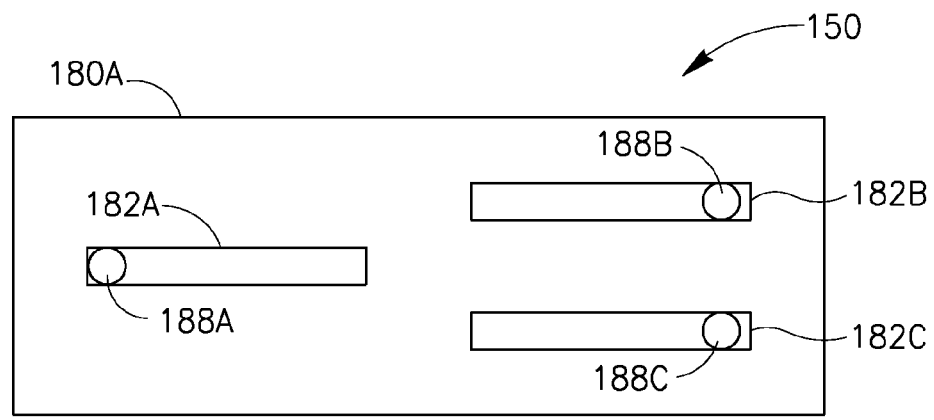

Reference is now made to FIGS. 9A-9C which are schematic diagrams illustrating top views of three different possible RF electrode configurations of a device having three controllably movable RF electrodes, in accordance with an additional embodiment of the present application.

In FIG. 9A, the top part of the device 180 is schematically illustrated. The housing 180 has three elongated (slot-like) openings 182A, 182B and 182C formed therein. Three movable RF electrodes 188A, 188B and 188C are movably disposed in the openings 182A, 182B and 182C, respectively. Preferably (but not obligatorily), the electrodes 188A, 188B and 188C are spring loaded (not shown in detail in the top view of FIGS. 9A-9C), in a way similar to the electrodes 108A-108E of the electrode assembly 120 (of FIG. 6). Each of the electrodes 188A, 188B and 188C may be and controllably moved laterally along the length of the respective opening in which the electrode is disposed. For Example, the RF electrode 188A may be controllably moved to any desired position along the opening 182A. The other RF electrodes 188B and 188C may each be similarly controllably moved within their respective openings 182B and 182C.

Each of FIGS. 9A, 9B and 9C represents a different RF electrode configuration achieved by moving the RF electrodes 188A, 188B and 188C to different positions within the openings 182A, 182B and 182C.

It is noted that in each of the different electrode configurations illustrated in FIGS. 9A, 9B and 9C, the distance between each of the electrodes and the other electrodes of the device 180 are different (as compared to the other remaining electrode configurations illustrated in the remaining figures. When the RF electrodes 188A, 188B and 188C are in contact with the skin and RF currents are passed through the electrodes into the skin, the RF current paths and the pattern of RF current distribution and depth of RF energy distribution in the skin (not shown) will be different for each configuration illustrated in FIGS. 9A, 9B and 9C.

This ability to change the RF electrode configuration of the device (such as for example the device 180 of FIGS. 9A-9C and the device 40 in its configuration including the attachable/detachable electrode assembly 56 of FIG. 4) and inter-electrode distance(s) by moving the electrodes may therefore be advantageously used to vary and to control the distribution of RF energy within the skin.

The RF electrodes 188A, 188B and 188C of the device 180 may be moved using any type of moving mechanism known in the art. For example, in accordance with one embodiment of the devices and systems of the present application, the RF electrodes 188A, 188B and 188C may be suitable movably coupled to suitable linear motors disposed within the device 180.

Figure 10A:
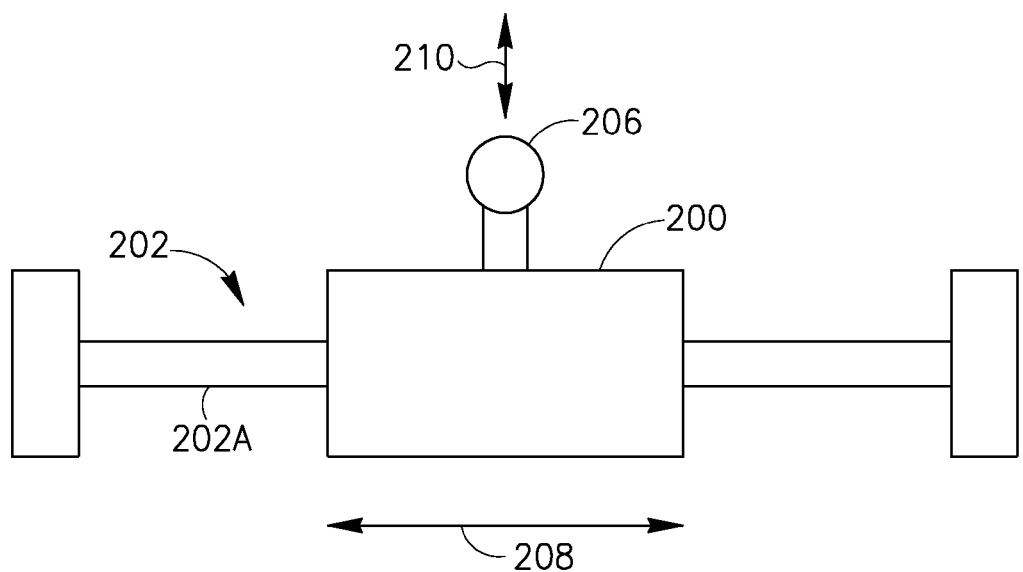
FIGS. 10A and 10B are schematic top view diagrams illustrating two electrode configurations of part of a moving mechanism including a linear motor for moving an RF electrode, in accordance with an embodiment of the skin treating device.
Figure 10B:
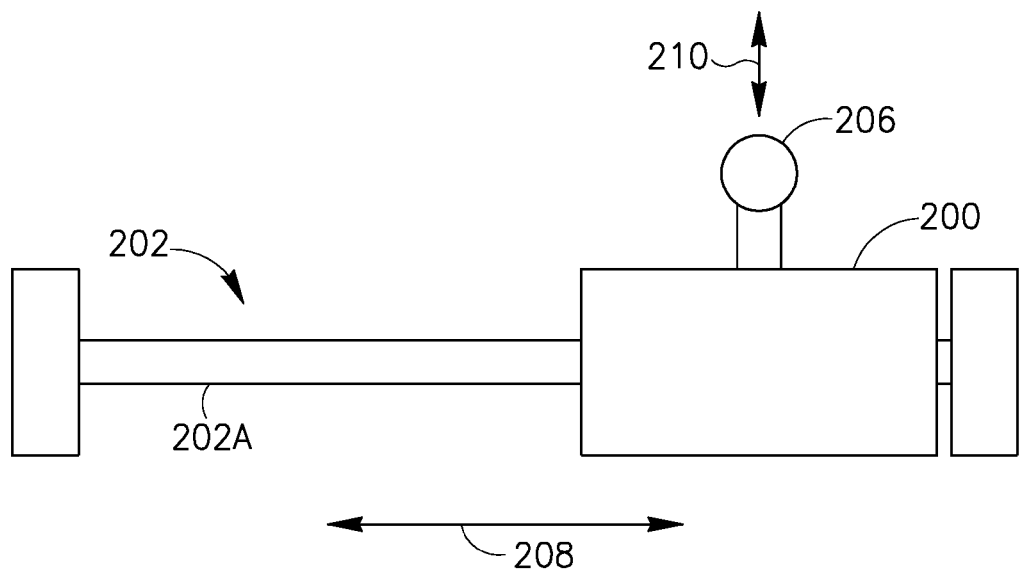

Reference is now made to FIGS. 10A and 10B which are schematic top view diagrams illustrating two electrode configurations of part of a moving mechanism including a linear motor for moving an RF electrode, in accordance with an embodiment of the devices and systems of the present application.

Turning to FIG. 10A, a linear motor 200 is suitably movably attached to an elongated guide member 202A which forms part of a framework 202. By suitably operating the linear motor 200, the linear motor 200 may be moved along the guide member 202A in the directions schematically represented by the double headed arrow 208 (the electrical connections of the motor 200 are not shown in detail for the sake of clarity of illustration). Turning to FIG. 10B, the motor 200 has moved along the guide member 202A to move the RF electrode 206 to a position that is different than the position of the same electrode 206 illustrated in FIG. 10A.

An RF electrode 206 is attached to the linear motor 200 such that it moves along with the motor 200. The RF electrode 206 may be any suitable type of RF electrode as disclosed hereinabove and/or as is known in the art. It is noted that the electrical conductors connected to the RF electrode 206 are not shown in FIGS. 10A-10B for the sake of clarity of illustration. However, such conductors may be implemented as any known type of electrical conductor known in the art, including but not limited to electrically conducting wires or ribbons or the like (insulated and/or non-insulated). Additionally, the guide member 202A and/or the framework 202 or parts thereof, and/or parts of the motor 200 or the housing thereof may be made of electrically conducting materials and may be used to form part of the electrical circuit supplying currents or voltages to the RF electrode. The details of constructing such implementations of electrical connections and circuits are well known in the art and are therefore not discussed in detail hereinafter.

The framework 202 may be suitably attached to a housing (not shown) of a device or an electrode assembly disclosed herein. For example, the framework 202 may be suitably attached to the housing 180A of the device 180 of FIG. 9A or may be suitably attached to the housing 58 of the RF electrode assembly 56 of FIG. 4.

Thus, for example, if the framework 202 is suitably rigidly attached to the housing 180A of the device 180 and the motor 200 is attached to the RF electrode 188A (instead of to the electrode 206 of FIG. 10A), the RF electrode 188A may be controllably moved to any selected position within (or along) the opening 182A (such as, but not limited to the positions of the RF electrode 188A illustrated in FIGS. 9A-9C) by suitably operating the motor 200.

In accordance with an embodiment of the devices of the present application, each of the electrodes 188A, 188B and 188C of the device 180 may be attached to a separate linear motor movably attached to a suitable framework (It is noted that the details of connecting such motors and frameworks to the RF electrodes and to the housing of the device 180 are not shown in FIGS. 9A-9C, but may be easily understood by those skilled in the art with reference to FIGS. 10A and 10B). In this embodiment each of the RF electrodes 188A, 188B and 188C may be independently and controllably moved within its respective opening by controllably operating the motor associated therewith. The three motors (not shown) may be controlled and operated by a suitable controller (not shown in FIGS. 9A-9C), such as, but not limited to, the controller unit 8 (of FIGS. 1-2) or by any other suitable controller or controllers as is known in the art. If the device 180 includes three different independent motor controllers for moving the different RF electrodes 188A, 188B and 188C, the controller unit 8 may be configured for suitably controlling and operating the three motor controllers (not shown) and for coordinating the operation of the three motors being used.

It is noted that while the electrode 206 of FIGS. 10A-10B is illustrated as being fixedly attached to the motor 200, it is possible, in accordance with an additional embodiment of the devices of the present application to implement the electrode 206 as a spring mounted or spring loaded type of RF electrode (the spring is not shown) similar to the spring loaded RF electrodes 108A-108E of FIG. 6. Such a spring loaded arrangement may advantageously allow the movement of the electrode 206 in the directions schematically represented by the double headed arrow 210 (of FIGS. 10A and 10B) to improve the contact of the RF electrode 206 with the skin (not shown in FIGS. 10A and 10B), when the device 180 is pressed against the skin.

In accordance with yet another embodiment of the devices and systems of the present application, it may be possible to change the distance between two different RF electrodes by implementing at least some of the electrodes as fixed RF electrodes (with respect to lateral movements represented by the double headed arrow 208 of FIGS. 10A-10B) that are stationary in the lateral direction, while being preferably (but not obligatorily being) movable in the directions schematically represented by the double headed arrow 210 of FIGS. 10A and 10B.

Figure 11A:
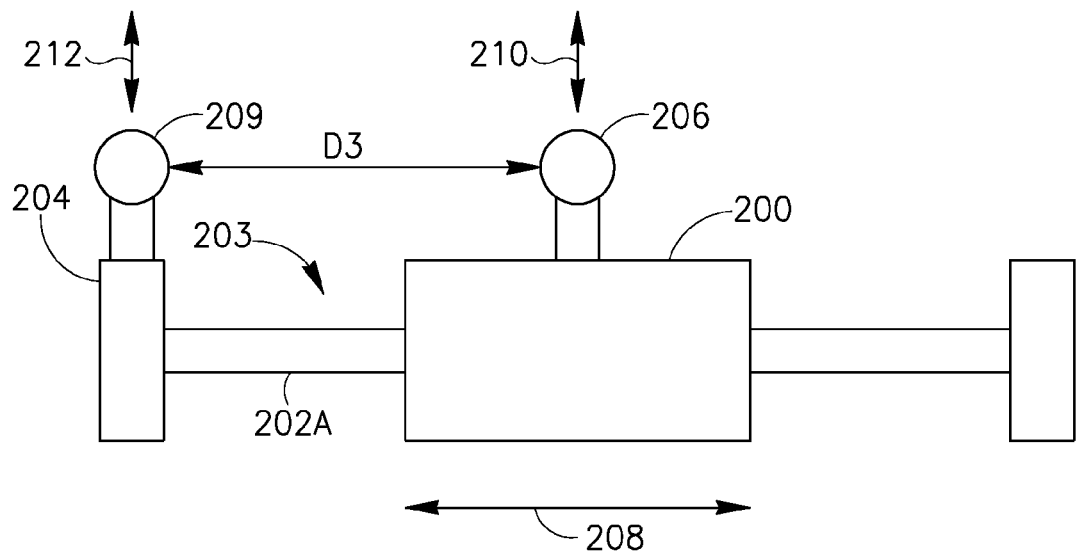
FIGS. 11A-11B are schematic diagrams illustrating two different electrode configurations of part of a moving mechanism including a linear motor for moving a movable RF electrode relative to another laterally stationary RF electrode, in accordance with another embodiment of skin treating device.
Figure 11B:
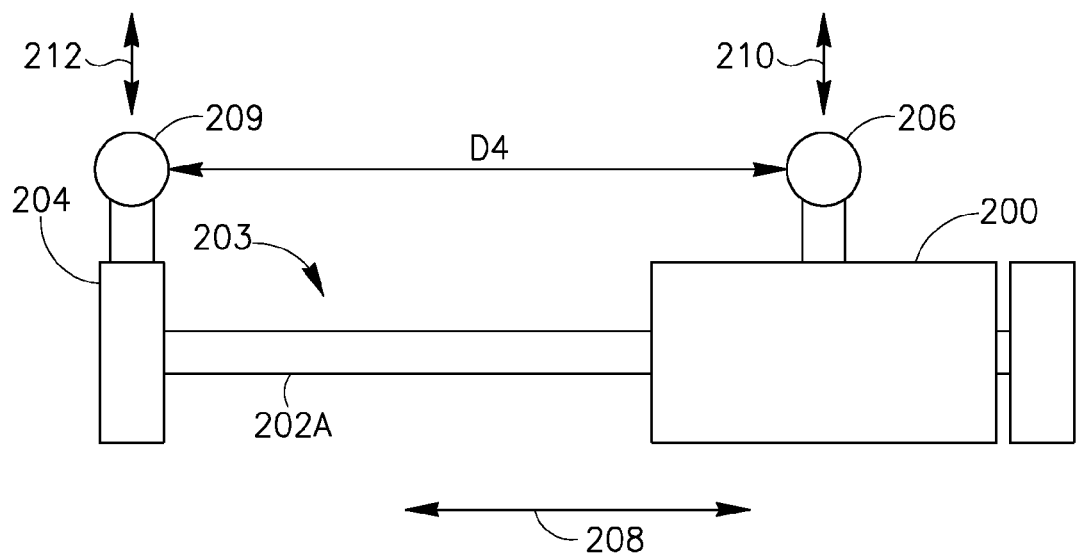

Reference is now made to FIGS. 11A-11B which are schematic diagrams illustrating two different electrode configurations of part of a moving mechanism including a linear motor for moving a movable RF electrode relative to another laterally stationary RF electrode, in accordance with another embodiment of the devices of the present application.

Turning to FIG. 11A, a linear motor 200 is suitably movably attached to an elongated guide member 202A which forms part of a framework 203. A movable RF electrode 206 is suitably attached to the motor 200 as disclosed in detail hereinabove for FIGS. 10A and 10B. A stationary (in the lateral direction) RF electrode 209 is attached to the part 204 of the framework 203. By suitably operating the linear motor 200, the motor 200 may be moved together with the movable RF electrode 206 attached thereto along the guide member 202A in the directions schematically represented by the double headed arrow 208 (the electrical connections of the motor 200 are not shown in detail for the sake of clarity of illustration).

Turning to FIG. 1B, the motor 200 has moved along the guide member 202A to move the RF electrode 206 to a position that is different than the position of the same electrode 206 illustrated in FIG. 11A. Due to the change in the position of the motor 200 in FIGS. 11A and 11B, the distance D3 (FIG. 11A) between the electrodes 206 and 209 is different (smaller) than the distance D4 between the electrodes 206 and 209 of FIG. 11B.

The RF electrodes 206 and 209 may be any suitable type of RF electrode as disclosed hereinabove and/or as is known in the art. It is noted that the electrical conductors connected to the RF electrodes 206 and 209 are not shown in FIGS. 11A-11B for the sake of clarity of illustration. However, such conductors may be implemented as any known type of electrical conductor known in the art, including but not limited to electrically conducting wires or ribbons or the like (insulated and/or non-insulated). Additionally, the guide member 202A and/or the framework 203 or parts thereof, and/or parts of the motor 200 or the housing thereof may be made of electrically conducting materials and may be used to form part of the electrical circuit supplying currents or voltages to the RF electrodes. The details of constructing such implementations of electrical connections and circuits are well known in the art and are therefore not discussed in detail hereinafter.

The framework 203 may be suitably attached to a housing (not shown) of a device or an electrode assembly of the present application as disclosed in detail for the framework 202 hereinabove.

It is noted that while the electrodes 206 and 209 of FIGS. 11A-11B is illustrated as being fixedly attached to the motor 200 and to the framework 203, respectively, it is possible, in accordance with an additional embodiment of the devices and systems of the present application to implement the electrode 206 or the electrode 209 (or both of the electrodes 206 and 209) as a spring mounted or spring loaded type of RF electrodes (spring not shown) similar to the spring loaded RF electrodes 108A-108E of FIG. 6. Such a spring loaded arrangement may advantageously allow the movement of the electrode 206 (and/or the electrode 209) in the directions schematically represented by the double headed arrows 210 and/or 212, respectively, (of FIGS. 11A and 11B) to improve the contact of the RF electrode 206 and/or of the electrode 209 with the skin (not shown in FIGS. 11A and 11B), when the device including the electrodes 206 and 209 is pressed against the skin.

It will be appreciated by those skilled in the art that the implementation of movable electrodes of the devices and electrode assemblies disclosed herein is not limited to the use of linear motors and of movable RF electrodes disposed within linear slots or openings as disclosed hereinabove. Rather, the scope of the present application includes any combination of movable RF electrodes and/or and of movable and stationary (or fixed) RF electrodes which are disposed within and/or moved along any types of openings and/or slots, including linear openings, curved openings and any suitable combinations and configurations of linear and curved openings. Such curved openings may include but are not limited to circular openings, elliptical openings, openings that are shaped as (non-closed) sections or parts of circles or ellipses, or any other irregularly or regularly shaped openings known in the art.

Reference is now made to FIGS. 12A-12B which are schematic top view diagrams, illustrating two different electrode configurations of part of a skin treatment device having one stationary RF electrode and some RF electrodes that are movable within elliptically shaped openings, in accordance with still another embodiment of the devices and systems of the present application.

Turning to FIG. 12A, a top view of the skin treatment device 220 is illustrated with the side of the device 220 which includes the RF electrodes facing the viewer. The housing 220A of the device 220 has two generally elliptical openings 222 and 224 formed therein with the outer elliptical opening 222 surrounding the inner elliptical opening 224. Two RF electrodes 226 and 227 are movably disposed within the inner opening 224 and may be controllably moved along the inner opening 224. An additional RF electrode 228 is movably disposed within the outer opening 222 and may be controllably moved along the outer opening 222.

An additional RF electrode 230 is attached to the housing 220A of the device 220. The RF electrode 230 may be fixed or may be spring mounted (as disclosed for the electrodes 108A-108E of FIG. 6, for example). However, in contrast to the movable electrodes 226-227 and 228 which may be moves within the openings 224 and 222 respectively, the RF electrode 230 may only be moved in a direction normal (generally perpendicular) to the surface of the housing 220A in the case that a spring mounted electrodes is used or may be immovably fixed to the housing 220A if a fully stationary or fixed RF electrode is used. Thus, the movable RF electrodes 226-227 and 228 may be controllably moved (within the openings 222 and 224, respectively, on the surface of the housing 220A) while the stationary RF electrode cannot be moved sideways (laterally) on the surface of the housing 220A.

The device 220 includes suitable moving mechanism(s) (not shown in FIGS. 12A-12B) which are coupled to the movable electrodes 226-227 and 228 and are arranged to controllably move the RF electrodes 226-227 and 228 within the openings 224 and 222, respectively. Such moving mechanisms are well known in the art, and may be easily constructed by those skilled in the art. For Examples many different types of motors, cogwheels, cams, pulleys or the like may be used to construct such electrode moving mechanisms. Such moving mechanisms may be controlled by separate multiple control mechanisms or control circuits or may also be controlled by a central controller or by any suitable combination of a central controller and additional motor controllers. Any motors used in such moving mechanisms may be a linear electrical motor(s), rotating shaft motor(s), or any other suitable type of motor(s) which may also be coupled to any other movement mechanism known in the art and capable of moving the RF electrodes 226-227 and 228 within their respective openings 224 and 222, respectively.

The device 220 also includes three temperature sensors 225A, 225B and 225C for sensing the skin temperature of the skin (not shown). The temperature sensors may be any suitable type of temperature sensors, such as but not limited to, thermistors, bollometers, IR sensors in the appropriate IR frequency range, or any other type of suitable temperature sensors known in the art.

The sensors 225A, 225B and 225C may be used for closed loop control of electrode group switching by sensing the skin temperature near the RF electrodes or by sensing the temperature of the RF electrodes 226-228 and 230 and switching to another group or another pair of electrodes if the skin temperature near an electrode or if the temperature of an electrode exceeds a certain threshold value. The threshold value (or values, if more than one threshold is used for different electrodes or for different skin regions, in accordance with another embodiment of the methods of the present application) may be factory preset or may be set by the user or operator of the device 220. Optionally, different electrode temperature thresholds may be used for different electrodes depending, inter alia, on the electrode shape, mass and thermal inertia. The controller of the device 220 (such as, but not limited to, the controller unit 8 of FIGS. 1-2) may receive the sensed signals from the temperature sensors 225A-225C and may use the signals to compute the skin temperatures near or at the RF electrodes to control the RF current application to the RF electrodes by group switching or pair switching as described in detail hereinabove.

It is noted that typically for sensing the temperature of one or more electrodes of the device 220 (or of any of the devices disclosed herein), the sensor(s) are preferably implemented as small solid state type temperature sensors attached to or embedded within the RF electrode(s). For example, small thermistor based temperature sensors may be used by attaching the thermistor(s) or any other suitable temperature sensors to the RF electrode or by embedding the sensors within the RF electrode, such that there is a good thermal contact between the temperature sensor and the RF electrode. Such temperature measurement methods and sensors are well known in the art and may be easily implemented by those skilled in the art, and are therefore not described in detail hereinafter. However, it may also be possible to use any other suitable type of temperature sensors (using contact or non-contact temperature measuring method) to determine the temperature of the RF electrode(s), as is known in the art.

In operation of the device 220, RF currents may be applied to the skin through any suitable pair of RF electrodes or group of RF electrodes selected from the RF electrodes 226-228 and 230. Any of the RF electrode pair switching or RF electrode group switching methods disclosed hereinabove may be used in operation of the device 220. Additionally or alternatively, one or more of the movable RF electrodes 226-228 may be controllably moved to change the distance(s) between the RF electrodes 226-228 and 230 or between some of the RF electrodes 226-228 and 230.

Turning to FIG. 12B, a new electrode configuration is illustrated resulting from moving each of the RF electrodes 226-228 to a new position which is different then their former position illustrated in FIG. 12A. Note that the stationary RF electrode 230 has not moved while the movable RF electrodes 226-228 have all moved to new positions.

It will be appreciated by the person skilled in the art that the changing of the positions of the electrodes 226-228 may change the pattern of distribution of RF currents and the distribution of RF energy deposition within the skin due to the resulting difference in the current paths and depth and three dimensional current density pattern of within the skin.

Thus, it is noted that the moving of any of the movable RF electrodes 226-228 to new positions may advantageously contribute to changing the RF energy heating of both superficial and deeper skin regions in such a way as to improve the more uniform heating of both superficial and deeper skin tissue regions.

It is further noted that, in accordance with one possible embodiment of the methods of the present application, the device 220 may be operated by using the electrode pair switching methods and/or electrode group switching methods as disclosed hereinabove, with or without moving any of the movable RF electrodes 226-228.

Similarly, in accordance with another possible embodiment of the methods of the present application, the device 220 may be operated by moving any of the movable RF electrodes 226-228 with or without using the electrode pair switching methods and/or electrode group switching methods as disclosed hereinabove.

Additionally, it may be possible to move any selected electrode or electrode combination of the movable electrodes 226-228 of the device 220 with or without moving the remaining movable electrodes.

It is also noted that many different modes of operation may be used in moving the movable electrodes of the present application. For example, in accordance with one possible mode of operation, one or more electrodes may be continuously moved during the operation of the device 220.

In another exemplary mode of operation in accordance with an embodiment of the methods of the present application, one or more of the movable RF electrodes 226-228 may be intermittently moved during the operation of the device 220 such that one or more of the RF electrodes 226-228 is moved for a certain period of time and remains stationary for another period of time (this sequence may be optionally repeated, with or without using electrode pair switching or electrode group switching as disclosed in detail hereinabove).

Similarly, various different RF electrode moving regimes and or sequences may be used for each different movable electrode and such movement sequences may be alternated between different movable RF electrodes.

It will be appreciated by those skilled in the art that many other combinations and permutations of electrode movements and/or movement temporal patterns and sequences and of electrode group switching and sequencing methods and/or temporal sequences may be used in various additional different embodiments of the invention. All such permutations and variations are contemplated to be included in the methods of the present application.

It is noted that the movable RF electrodes of the present application may be implemented in hand held applicators with fixed electrode assemblies and in any of the attachable/detachable RF electrode assemblies of the present application.

It is also noted that the anti-sparking methods and switches disclosed hereinabove and illustrated in FIG. 7A-7B may also be implemented in the construction and operation of any of the skin treatment devices and/or RF electrode assemblies (fixed and/or detachable) including movable RF electrodes.

Furthermore, the devices and systems described herein may be configured to have multiple (two or more) RF electrode groups.

Figure 13:
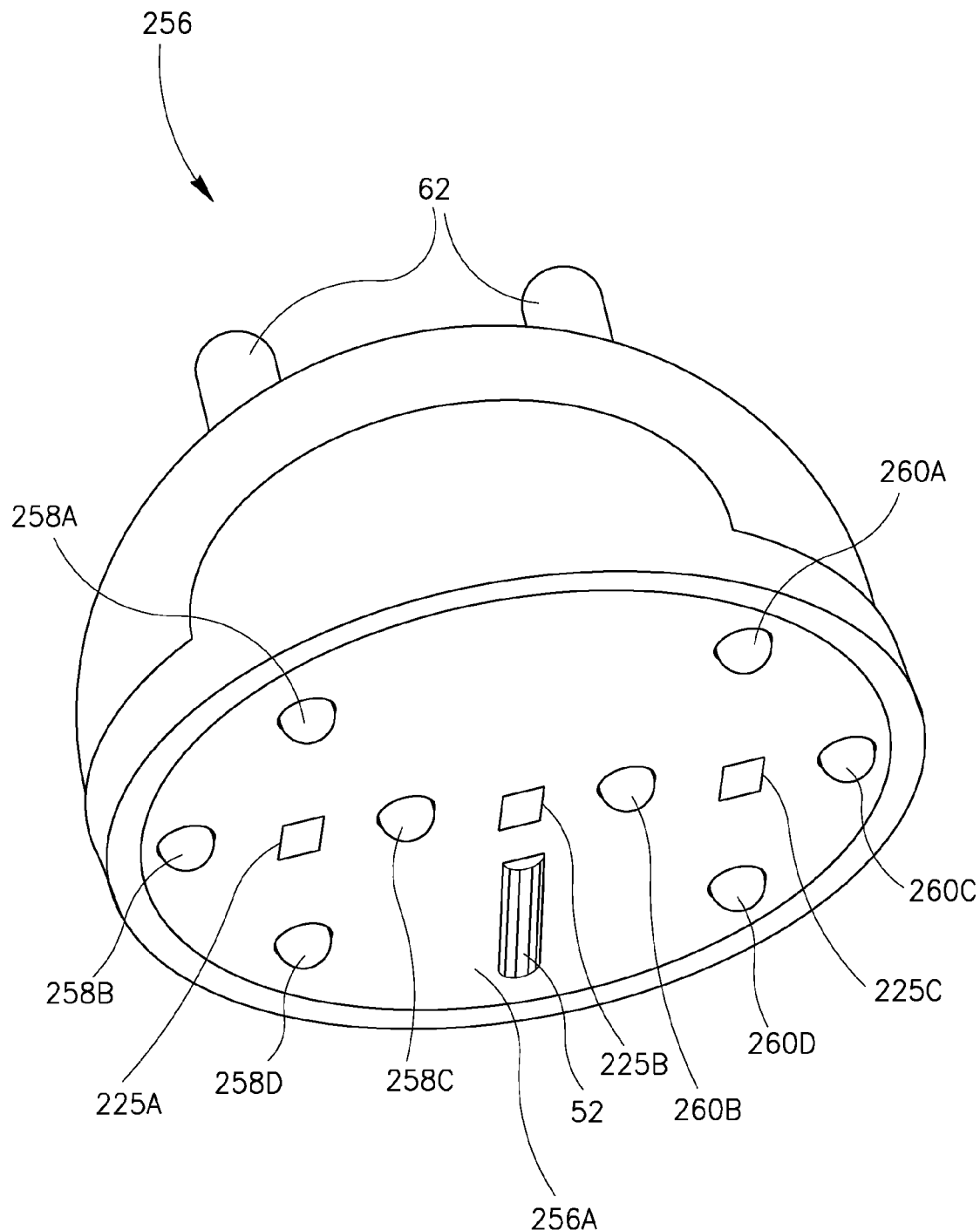
FIG. 13 is a schematic isometric view illustrating an RF electrode assembly having eight RF electrodes arranged in two electrode groups in accordance with an embodiment of the RF electrode assembly.

Reference is now made to FIG. 13 is a schematic isometric view illustrating an RF electrode assembly having eight RF electrodes arranged in two RF electrode groups in accordance with an embodiment of RF electrode assemblies of the present application.

The RF electrode assembly 256 includes an assembly housing 250 (which may be similar in construction to the assembly housing 58 and/or 78 of FIG. 4). The front surface 256A of the RF electrode assembly 256 includes two groups of RF electrodes disposed therein. Each electrode group includes four RF electrodes. The first RF electrode group includes RF electrodes 258A, 258B, 258C and 258D and the second RF electrode group includes RF electrodes 260A, 260B, 260C and 260D. The RF electrode assembly 256 also includes electrical contacts 62 as disclosed in detail hereinabove (See FIG. 4). The RF electrode assembly 256 may also (optionally) include a sensor 52 for determining the velocity of the RF electrode assembly 256 relative to the skin, as disclosed in detail hereinabove, and an (optional) temperature sensor units 225A, 225B and 225C (constructed and operating as disclosed in detail hereinabove with respect to FIGS. 12A and 12B).

The RF electrode assembly 256 may be a detachable electrode assembly similar in construction to the electrode assembly 76 (of FIG. 4), or a permanent (fixed) electrode assembly, as described in detail hereinabove.

In accordance with one possible embodiment, the two electrode groups 258A-258D and 260A-260D may all be energized by a single RF energy generating unit (such as, but not limited to, the RF energy generating unit 4 of FIGS. 1-2). The application of RF currents to the skin through different pairs of RF electrode within each RF electrode group may be performed by any of the electrode pair switching methods as described in detail hereinabove (including, but not limited to bipolar and tripolar RF electrode configurations as described in detail hereinabove).

It is noted that while in the exemplary embodiment illustrated in FIG. 13, the number of electrodes, the geometrical arrangement and the size and type of RF electrodes within the electrode group including RF electrodes 258A-258D are identical to the number of electrodes, the geometrical arrangement and the size and type of the RF electrodes within the electrode group including RF electrodes 260A-260D, this is by no way obligatory. Thus, the number of electrodes, the geometrical arrangement of the electrodes and the size and type of electrodes included in each RF electrode group may vary according to need and purpose of different embodiments of the device and may differ in different RF electrode groups of the same device.

In accordance with another possible embodiment, each of the two electrode groups 258A-258D and 260A-260D may be energized by a different RF energy generating unit.

Reference is now made to FIG. 14 which is a schematic block diagram illustrating the components of a device for skin treatment, having two RF energy generating units in accordance with an embodiment of the devices and systems of the present application.

The device 280 includes a power source 12 for providing power to the various components of the device 280. The power source 12 is preferably an electrical power source as described in detail hereinabove (with respect to FIGS. 1-2). The power source 12 may be internal to the device 280 (as illustrated in FIG. 14) but may also be disposed external to the device 280 (similar to the configuration illustrated in FIG. 2). It is noted that the connections of the power source 12 with the power consuming components of the device 280 (of FIG. 14) are not shown for the sake of clarity of illustration.

The device 280 also includes one or more controller unit(s) 13, suitably connected to two RF energy generating units 270 and 272. The RF energy generating unit 270 is suitably connected to RF electrodes 258A-258D to provide RF energy to the electrodes 258A-258D and the RF energy generating unit 272 is suitably connected to RF electrodes 260A-260D to provide RF energy to the electrodes 260A-260D.

The device 280 also includes a user interface 285 suitably connected to the controller unit(s) 13 for receiving output signals and data from the controller unit(s) 13 and for inputting user commands or control signals to the controller unit(s) 13. The user interface 285 may be any type of user interface known in the art and may include any components usable for communicating user commands or control input to the device 280 and from outputting data signals and/or and status signals and/or alarm signals to the user.

For example, the user interface 285 may include but is not limited to any combination of display units (such as, for example the display unit 29 of FIG. 3) for presenting visual output to the user, audible signal units (such as, for example, the speaker unit 28 of FIG. 3) for producing indicating audible signals and/or alarm signals to the user, keyboards, keypads, light-pens, touch-screens, a mouse, one or more pointing devices useable for receiving input from the user, and any other input or output devices for allowing communication between the user and the device as is known in the art.

While, preferably, the controller unit(s) 13 is implemented as a single controller unit, it may be possible to implement the controller unit(s) 13 as two or more different controller units, if desired. If more than one controller unit 13 is used, the different controller units 13 may be in communication by being suitably connected (not shown in FIG. 14) in order to synchronize their operation. Alternatively, each of the different controller units in a multi-controller implementation of the device 280 may be operated independent of any other controller unit. For example, if two controller units are used, the first controller unit may be used for independently controlling the application of RF energy to the skin through the electrode group including the RF electrodes 258A-258D and the second controller unit may be used for independently controlling the application of RF energy to the skin through the electrode group including the RF electrodes 260A-260D.

It is noted that if any of the RF electrodes 258A-258-D and 260A-160D of the device 280 are implemented as laterally movable electrodes, as disclosed in detail hereinabove, the device 280 may also include an electrode moving unit 290, suitably connected to the controller unit(s) 13. The electrode moving unit 290 may be implemented as any type of suitable moving mechanism known in the art, including but not limited to the linear motors disclosed in detail herein (with respect to FIGS. 9A-9B, 10A-10B and 11A-11B) or as any other suitable type of motor or moving mechanism disclosed herein or known in the art. Such moving mechanisms may include but are not limited to, linear motors, non-linear motor(s), gear coupled motors, electromechanical moving mechanisms and devices, electromagnetic moving mechanisms, solenoid actuated moving mechanisms, stepper motors, or any other moving mechanism capable of moving an RF electrode in any suitable direction, as is known in the art. The controller unit(s) 13 may in such a case control the operation of such an electrode moving unit 290, by suitably controlling the operations of any motors and/or moving mechanisms used for changing the positions of the RF electrode(s) relative to each other.

The application of RF energy to the skin through each of the electrode groups 258A-258D and 260A-260D may be implemented using any method of RF electrode switching described hereinabove, including but not limited to electrode pair switching, bipolar and/or tripolar electrode configurations, as disclosed hereinabove.

The electrode pair switching methods and/or electrode group switching methods used within each RF electrode group may be identical or may be different within each RF electrode group of the device 280. For example, the application of RF energy to the skin by the RF electrode group including RF electrodes 258A-258D may be operated separately and/or independently and/or non-synchronously from the application of RF energy to the skin by the RF electrode group including the RF electrodes 260A-260D.

However, it is also contemplated in accordance with another embodiment of the device 280 to synchronize or at least partially coordinate the operation of RF energy to the skin through the two (or more than two) RF electrode groups.

It is noted that while the RF electrode assembly 256 of FIG. 13 is illustrated as an embodiment having stationary RF electrodes, in accordance with an additional embodiment, all or some of the electrodes 258A-258D and 260A-260D may be movable and/or spring mounted to enable movement in a direction generally perpendicular to the surface 256A of the RF electrode assembly 256 as disclosed in detail hereinabove and illustrated in FIGS. 5-6 and 7A-7B and may also have micro-switch (or other sensor type) implemented spark prevention mechanisms.

Furthermore, while the RF electrode assembly 256 of FIG. 13 is illustrated as an embodiment having laterally stationary electrodes, other embodiments may be implemented using laterally movable electrodes that may disposed in suitable slot-like openings (not shown in FIG. 13) formed in the housing 250 of the RF electrode assembly 256. Such movable electrode arrangement may be implemented using any of the methods and moving mechanisms disclosed in detail hereinabove with respect to FIGS. 4, 9A-9C, 10A-10B, 11A-11B and 12A-12B and may be controllably moved laterally within such slots as described hereinabove to change the distance between some or all of the RF electrodes 258A-258D and/or 260A-276D, as described in detail hereinabove. It is noted that any other suitable methods and mechanisms known in the art for moving the RF electrodes 258A-258D and/or 260A-276D may be implemented.

In a non-limiting example, if an electrode pair switching method is used, the order of operation and or selection of the electrode pair(s) in the two (or more than two) different RF electrode groups may be identical within each of the RF electrode groups (provided that the number and type of RF electrodes within each RF electrode group is identical).

In another non-limiting example, if an electrode pair switching method is used, the order of operation and or selection of the electrode pair(s) in the two (or more than two) different RF electrode groups may be different within each of the RF electrode groups.

It is noted that using a plurality of RF energy generating units in the device 280 may be used to enable the implementation of devices for treatment of large skin regions, without having to resort to the use of a single, large high power (and therefore expensive) power RF energy generating unit. The advantages of the use of such multiple RF energy generating units may include, inter alia, reduction of component cost, and more efficient and economical heat dissipation in the device.

Furthermore, in accordance with an embodiment of the device 280, the RF energy generating unit 270 is similar to the RF energy generating unit 272. In operation, the RF energy generating units 270 and 272 are operated at similar (but not necessarily identical) RF frequencies. For Example, in accordance with one embodiment of the device 280, both RF energy generating units 270 and 272 are operated at the nominal RF frequency of 1 MHz. However, since the RF energy generating units 270 and 272 are typically not operating in phase (as the RF frequency oscillators of the two units may be out of phase with each other), this may result in location dependent interference of the RF waves along and within the treated skin region. Thus in skin regions in which there is a superposition of peaks of RF waves, the RF wave amplitude may be up to twice the amplitude of the wave peak of a single wave from a single RF energy generating unit) and the instantaneous RF power dissipation may be up to four times that of the single wave from a single RF energy generating unit operated alone), as the power dissipation within the skin is proportional to the squared wave amplitude.

Thus, by operating two (or more than two) non-phase synchronized RF energy generating units to treat a skin region it is possible to advantageously reach higher levels RF power delivery in at least some skin regions (where there is constructive wave interference) with concomitant increase in local skin temperatures in such skin regions.

When movable and/or switchable electrode pairs and/or electrode group configurations are being used as described in detail hereinabove, the regions of constructive interference will vary and shift within the skin in accordance with electrode pair activation and/or electrode movements (lateral movements and/or movements generally perpendicular to the electrode assembly surface), to average the power dissipation over time (thus, effectively avoiding permanent "hot spot" formation).

It is noted though that in accordance with another embodiment of the device the same RF wave superposition may be achieved by using a single RF energy generating unit in combination with a phase shifting device.

Reference is now made to FIG. 15 which is a schematic block diagram illustrating the components of a skin treating device including a single RF energy generating unit, a phase shifting unit and two RF electrode groups.

The skin treating device 300 includes the controller unit(s) 13 and a user interface 285 suitably connected to the controller unit(s) 13 as described in detail hereinabove with respect to FIG. 14. The device 300 also includes an RF energy generating unit 302 suitably connected to the controller unit 13 and one or more (optional) sensor units 282 suitably coupled to the controller unit(s) 13. The sensor units(s) 282 may include any type of desired sensor or sensors combination, including but not limited to the various temperature sensor types described herein (such as but not limited to the temperature sensors 225A-225C of FIGS. 12A-12B and FIG. 13), velocity sensor units (such as, but not limited to the velocity sensors units 52 and 114 of FIGS. 4 and 6, respectively), micro-switch type sensors (such as but not limited to the micro-switch 140 of FIGS. 7A-7B), or any other type of sensor known in the art.

The device 300 further includes a power source 12 as disclosed hereinabove. In the embodiment illustrated in FIG. 15, the power source 12 is an internal power source included within the device 300. However, in accordance with an additional embodiment, the power source 12 may be an external power source disposed outside the device 300 (not shown in FIG. 15). It is noted that the electrical connections of the power source 12 with the various electrical power requiring components of the device 300 are not shown in FIG. 15 for the sake of clarity of illustration.

The device 300 further includes RF electrodes 310, 312, 314 and 316 arranged in two electrode groups. A first group of electrodes labeled Group-A, includes RF electrodes 310 and 312. A second group of electrodes labeled Group-B includes RF electrodes 314 and 316. Electrodes 310 and 314 are electrically connected to the first end of the output (secondary) transformer coil 303 of the RF energy generating unit 302 and RF electrodes 312 and 316 are electrically connected to the other end of the output transformer coil 303. A phase shifting unit 306 is electrically connected between the RF electrode 310 and the first end of the output transformer coil 303 (as illustrated in FIG. 15). This type of arrangement introduces a phase shift in the waveform of the RF wave applied to the skin (not shown in FIG. 15) by electrodes 310 and 312 relative to the RF wave applied to the skin by RF electrodes 314 and 316.

The phase shifting unit 306 may be any suitable phase shifting unit or circuit operable in the RF frequency range. For example, the phase shifting unit 306 may be an RC circuit (including a combination of resistive and capacitive electrical elements) or an RLC (including resistive, capacitive and inductive electrical elements), as is well known in the art. However, any suitable type of device or electrical circuit capable of introducing a phase shift into an electromagnetic waveform may be used to implement the phase shifting unit 306.

It is noted that while the RF energy generating unit 302 of FIG. 15 includes a single secondary output coil 303 which provides RF energy to all the RF electrodes 310, 312, 314 and 316 of groups A and B of RF electrodes, it may be possible in accordance with another embodiment of the device 300 to use an RF energy generating unit having multiple secondary output coils (not shown in FIG. 15) as is known in the art. In such a case, each electrode pair (such as, for example, the electrode pair including RF electrodes 310 and 312 and the electrode pair including the RF electrodes 314 and 316) may be electrically connected to the output terminals of a different output (secondary) coil of the plurality of multiple output coils of the RF energy generating unit. In such a case multiple phase shifting units may be used and each different phase shifting unit may be connected between one terminal of each output (secondary) coil and one of the RF electrodes of an RF electrode pair.

It is noted that while the embodiment of the device 300 illustrated in FIG. 15 discloses an implementation including only two electrode pair groups (group-A and Group-B) it is possible to implement other embodiments of the device having more than two electrode pairs by suitably increasing the number of electrode pairs to include any desired number of electrode pairs (with additional phase shifting units, where necessary).

Similarly, while the device 300 of FIG. 15 includes RF electrode pairs, it may be possible to use different embodiments of the device using electrode groups that may include more than two RF electrodes per group. For example, in accordance with another embodiment of the skin treating device, one or more of the RF electrode groups may include three RF electrodes arranged and operated in a tripolar configuration. In such RF electrode triplets, the phase shifting unit of the tripolar electrode group may be connected to only one of the three RF electrodes of each RF electrode triplets.

Thus, in accordance with other different embodiments of the skin treating device 300, any suitable combination of RF electrode groups and configurations may be used with or without phase shifting, such as but not limited to, multiple RF electrode groups, any selected number of RF electrodes within any of the electrode groups. And any suitable number and type of phase shifting units implemented to introduce a phase shift of the RF waveform(s) of at least one RF electrode group relative to the phase of at least one other RF electrode group of the device.

Furthermore, some or all of the RF electrodes used in the multiple RF electrode groups of skin treatment devices using phase shifting methods may be stationary (fixed) electrodes or movable electrodes as disclosed in detail hereinabove. Such movable electrodes may be movable in a direction generally perpendicular to the surface of the RF applicator (such as, for example, the RF electrode 128 of FIGS. 7A-7B and the RF electrodes 10A-108E of FIGS. 5 and 6), or may be laterally movable as disclosed in detail hereinabove (such as, but not limited to the laterally movable RF electrodes 68A-68B of the electrode assembly 56 of FIG. 4, the laterally movable RF electrodes 188A-188C of FIGS. 9A-9C, the laterally movable RF electrode 206 of FIGS. 10A-10B and the laterally movable RF electrodes 226 227 and 228 of FIGS. 12A-12B). If any of the RF electrodes 310, 312, 314, and 316 are implemented as movable electrodes, the device 300 may include the electrode moving unit 290 which may be connected to the controller unit(s) 13, as disclosed in detail hereinabove with respect to the electrode moving unit 290 of the device 280 (of FIG. 14).

Alternatively or additionally, some or all of the RF electrodes of the skin treating devices described herein may be movable electrodes which may be moved in a direction generally perpendicular to the front surface of the RF applicator as well as in lateral direction (generally parallel to the surface of the RF applicator in which the RF electrodes are disposed).

It is noted that in accordance with another embodiment of the skin treatment device, more than two RF energy generating units may (optionally) be used in the devices to provide RF energy to more than two groups of RF electrodes. Thus the devices may include any desired practical number N of RF energy generating units for operating M groups of RF electrodes (where N and M are integer numbers, and wherein M may be equal to or different than N). The construction and operation of such device embodiments with multiple RF electrode groups and multiple RF energy sources may be easily achieved by those skilled in the art based on the Examples and principles described herein.

The use of multiple RF energy generating units operating at different RF frequencies may be implemented in different types of RF energy application methods and device configurations. The first type of device is a device including several (two or more than two) different RF energy generating units in the same device with each RF energy generating unit operating in a different RF frequency or in a different RF frequency band while each group or pair of RF electrodes is electrically coupled to a single RF energy generating unit operating in a single RF frequency or in a single RF frequency band.

Turning back to FIG. 14, in accordance with another embodiment of the device 280, the RF energy generating unit 270 may be different than the RF energy generating unit 272. The differences between the RF energy generating units 270 and 272 may include but are not limited to differences in the RF frequency used, the RF frequency band used the total power delivery capacity, the duty cycle (if pulsed RF is being used), or any other characteristic of the RF application to the skin.

For example, in accordance with one exemplary embodiment of the device 280, the RF energy generating unit 270 may operate using RF frequencies at or about 1.0 MHz, and the RF energy generating unit 272 may operate using RF frequencies at or about 10.0 MHz.

It is known that different frequencies of RF may be differentially absorbed by different types of tissues. For example, RF frequencies in the range of 0.35-1.5 MHz are preferentially more efficiently absorbed by fatty tissues such as, for example sub-dermal or hypodermal adipose tissues, while RF frequencies in the range of 4.0-15.0 MHz are preferentially more efficiently absorbed by non-fatty epidermal and/or dermal tissues.

Thus, in applications in which it is desired to preferentially heat deeper fatty tissues such as hypodermal adipose tissues or rete pegs (such as, for example, in cellulite reduction applications), it is possible to operate the device 280 in a first mode by switching on only the RF energy generating unit 270 and applying RF frequencies at or about 1.0 MHz to the skin through the electrode group including the RF electrodes 258A-258D for preferentially heating fatty skin tissues. In such a mode of operation, the RF energy generating unit 272 is switched off so that no RF energy is applied to the skin through the remaining electrode group including RF electrodes 260A-260D.

Thus, the RF frequency or frequencies applied in different operating modes of the devices and systems disclosed in the present application may be selected for preferentially heating different types of skin tissues selected from fatty skin tissue, hypodermal adipose tissue, rete pegs, non-fatty dermal tissue, epidermal tissue and various combinations thereof.

Alternatively, in applications in which it is desired to heat the skin layer substantially uniformly (such as, for example, in skin-tightening applications in which it is desired to heat both superficial and deeper skin layers to effect contraction of collagen as uniformly as possible throughout all skin layers), it is possible to operate the device 280 in a second mode by switching on both of the RF energy generating units 270 and 272 to apply RF frequencies having frequencies at or about 1 MHz to the skin through the electrode group including the RF electrodes 258A-258D RF while simultaneously applying RF frequencies at or about 10.0 MHz to the skin through the remaining electrode group including RF electrodes 260A-260D.

In a third operation mode of the device 280, it is possible to switch on only the RF energy generating unit 272 (while the RF energy generating unit 270 is switched off) and to apply RF energy to the skin using RF frequencies at or about 10.0 MHz through the RF electrodes 260A-260D. Such a mode of operation may be used if it is desired to preferentially heat non-fatty skin tissues.

It is noted that while the device 280 is configured for using two different RF frequencies or two different RF frequency bands), it may also be possible to use more than two RF frequencies or two RF frequency bands by including additional RF generating units (not shown in FIG. 14) capable of delivering additional appropriate RF frequencies or RF frequency bands. Such additional RF energy generating units may be suitably connected to suitable additional RF electrodes (not shown in FIG. 14) for applying the Additional RF frequencies to the skin.

It is noted that while the device 280 is configured such that the RF electrodes 258A-258D are hard-wired to the RF energy generating unit 270 and the RF electrodes 260A-260D are hard-wired to the RF energy generating unit 272, this is not obligatory and devices may be configured such that different various combinations of RF frequencies or RF frequency bands may be flexibly and controllably applied to the skin through any selected RF electrodes and/or RF electrode groups.

Reference is now made to FIG. 16 which is a schematic block diagram illustrating the components of a skin treatment device having a plurality of RF energy generating units controllably connectable to a plurality of RF electrodes.

The skin treating device 320 of FIG. 16 includes the one or more controller units 13, the user interface 285, the power source 12 and the sensor unit(s) 282 interconnected as disclosed in detail for FIG. 15 hereinabove.

The device 320 also includes a plurality M of RF generating units 315A, 315B . . . 315M. Each of the RF generating units 315A-315M is constructed to operate at a specific RF frequency or a specific RF frequency band. The RF frequencies and/or RF frequency bands of the different RF generating unit may be different for each RF energy generating unit or at least for some of the RF energy generating units 315A-315M. If RF frequency bands are used The RF frequency bands of at least some of the RF energy generating units 315A-315M may be different (i.e. completely non-overlapping frequency bands). Alternatively or additionally, for at least some (or for all) of the different RF energy generating units 315A-315M, the RF frequency bands may completely or partially overlap.

The device 320 further includes a multiplexing/switching unit 330 suitably connected to each of the RF energy generating units 315A-315M. The multiplexing/switching unit 330 is suitable electrically connected to a plurality N of RF electrodes 312A, 312B, 312C . . . 312N.

The multiplexing/switching unit 330 includes a plurality of controllable switches (not shown in FIG. 16 for the sake of clarity of illustration) such that the controller unit(s) 13 may individually control each and every of the switches included in the multiplexing/switching unit 330. The multiplexing/switching unit 330 is configured such that any combination of RF energy generating units selected from the RF generating units 315A-315M may be electrically connected or coupled to any combination of RF electrodes selected from the plurality of RF electrodes 312A-312N. The construction details of such multiplexing/switching units (including electromechanical multiplexers and solid state multiplexers) is well known in the art, is not the subject matter of the present application and is therefore not described in detail hereinafter.

By using the multiplexing/switching unit 330 under the control of the controller unit(s) 13, it is possible to apply to any selected pair or pairs of RF electrodes or to each selected group of RF electrodes any combination of RF frequencies or any combination of RF frequency bands by controllably changing (by connecting or disconnecting) the connectivity of the RF energy generating units 315A-315M to any of the RF electrodes 312A-312N.

It is noted that in accordance with another embodiment of the multi-frequency skin treating device disclosed herein, the multiplexing/switching unit 330 may include any suitable number of phase shifting devices (not shown in detail in FIG. 16 for the sake of clarity of illustration) which may be controllably electrically connectable between one or more of the M RF energy generating units 315A-315M and one or more RF electrodes selected from the plurality of N RF electrodes 312A-312N. Such phase shifting units may be used to shift the phase of the RF electromagnetic wave of some RF electrodes relative to the phase of other RF electromagnetic waves applied through other RF electrodes. This may be useful for creating interference of RF waveforms in the skin with the same localized or region specific increase of RF power dissipation as disclosed hereinabove with respect to the device 300 of FIG. 15.

It is noted that in accordance with another embodiment of the multi-frequency skin treating device disclosed herein, any RF electrodes selected from the plurality of RF electrodes 312A-312N may be movable RF electrodes (such as, but not limited to the movable electrodes 68A and 68B of FIG. 4 or any of the movable electrodes illustrated in FIGS. 9A-9C, 10A-10B, 11A-11B, 12A-12B) and the device 320 may also include the electrode moving unit 290 (of FIG. 15) connected to the controller unit(s) 13 for controlling the moving of such movable electrodes as disclosed in detail hereinabove.

In accordance with one possible non-limiting example of the device 320, if M=2 (i.e. there are two RF energy generating units in the device 320) and N=4 (i.e. there are four RF electrode 312A, 312B, 312C and 312D in the device 320), and if the RF energy generating unit 315A is constructed to operate at the RF frequency of 0.5 MHz and the RF energy generating unit 315B is constructed to operate at the RF frequency of 10.0 MHz, and if there are two bipolar electrode pairs, an electrode pair A including RF electrodes 312A-312B and an electrode pair B including RF electrodes 312C-312D, it may be possible to deliver to the skin the following RF frequency combinations:

1) Each of the electrode pairs A and B applies a combination of both RF frequencies (0.5 MHz+10.0 MHz) to the skin.

2) The RF frequency 0.5 MHz is applied to the skin through electrode pair A and the RF frequency 10.0 MHz is applied to the skin through electrode pair B.

3) The RF frequency 0.5 MHz is applied to the skin through electrode pair B and the RF frequency 10.0 MHz is applied to the skin through electrode pair A.

4) The RF frequency 0.5 MHz is applied to the skin through electrode pair A and the RF frequency combination of 0.5 MHz+10.0 MHz is applied to the skin through electrode pair B.

5) The RF frequency 0.5 MHz is applied to the skin through electrode pair B and the RF frequency combination of 0.5 MHz+10.0 MHz is applied to the skin through electrode pair A.

6) The RF frequency 10.0 MHz is applied to the skin through electrode pair B and the RF frequency combination of 0.5 MHz+10.0 MHz is applied to the skin through electrode pair A.

7) The RF frequency 10.0 MHz is applied to the skin through electrode pair A and the RF frequency combination of 0.5 MHz+10.0 MHz is applied to the skin through electrode pair B.

8) The RF frequency 10.0 MHz is applied to the skin through electrode pair A (no RF energy is applied through the RF electrode pair B).

9) The RF frequency 10.0 MHz is applied to the skin through electrode pair B (no RF energy is applied through the RF electrode pair A).

10) The RF frequency 0.5 MHz is applied to the skin through electrode pair A (no RF energy is applied through the RF electrode pair B).

11) The RF frequency 0.5 MHz is applied to the skin through electrode pair B (no RF energy is applied through the RF electrode pair A).

12) The RF frequency combination of 0.5 MHz+10.0 MHz is applied to the skin through electrode pair A and no RF frequency is applied to the skin through the electrode pair B.

13) The RF frequency combination of 0.5 MHz+10.0 MHz is applied to the skin through electrode pair B and no RF frequency is applied to the skin through the electrode pair A.

14) No RF Frequency is applied to the skin through the electrode pairs A and B.

It is noted that since the RF electrode pairs A and B have different spatial locations on the skin, each of the above fourteen possible electrode and frequency combinations represents a different and unique RF energy application pattern to the skin (including the fourteenth combination which represents zero RF energy application to the skin).

When we add to this the fact that M an N may be varied at will, and that any of the electrodes 312A-312N may be implemented as a stationary or as a laterally movable electrode, and that any of the phase shifting methods described hereinabove may also be applied to the device 320 by proper inclusion of suitable phase shifting units in the device 320, it is apparent that the device 320 may enable a very large number of RF electrode and RF frequency combinations which may be used to achieve a very fine degree of control over the distribution pattern of RF energy and the resulting heating of various regions of the skin.

Furthermore, any of the above indicated combinations and any other possible higher numbers of combinations with higher numbers of RF electrodes and of application of different multiple RF frequencies and/or multiple frequency bands to the skin (including all possible combinations with or without phase shifting, different RF electrode distances using different movable electrode configuration and distances, and multiple different electrode group switching methods as disclosed hereinabove) may be activated and/or inactivated at different time periods during the skin treatment to enable fine control of treatment parameters, including but not limited to, differential heating of different skin layers or skin regions, prevention of sparking and of exceeding safe skin temperature and/or RF electrode temperatures, and the degree of uniformity of heat distribution within selected skin layers or regions.

All such RF energy application regimes and modes may be effected by automatic control of the timing of activation of various electrode groups, the applied RF frequencies, active electrode group selection, active control of inter-electrode distance modifications and active control of RF phase shifting, by the processing of different signals received from any of the above disclosed sensor(s) or sensor combinations controlling changes in any of the above described RF energy application modes and configurations based on data obtained by the controller unit through processing of the signal received from the sensor(s).

Alternatively or additionally, control of RF energy application to the skin may be achieved by selecting (by the user, through the appropriate user interface) of selected preset or user programmable sequences of RF energy application available for the device or system by using any of the control methods and combinations disclosed hereinabove to determine the treatment mode (such as, but not limited to, cellulite reduction mode or skin tightening mode or face sculpturing mode or any other suitable mode of operation of the device or system).

In accordance with an embodiment of the devices and systems of the present application, the selection of any such modes by the user does not interfere with any of the safety features included in the device (such as, but not limited to the sparking prevention or reduction methods, the skin and/or electrode temperature threshold based safety methods, or any other safety method or mechanism being used by the device or system) which may continue to operate independently and which may have a programmed priority or overriding control over RF energy application (by possible termination thereof) in cases where any of the safety threshold(s) have been exceeded or the indication of possible sparking has been detected, as described in detail hereinabove.

It is noted that all possible different combinations, permutations and sub-combinations of the RF application methods described herein may be used in implementing and operating the devices and systems disclosed in the present application, including but not limited to, any possible combinations, sub-combinations and permutations of the methods of RF electrode pair switching, RF electrode group switching, application of Multiple different RF frequencies and/or RF frequency bands though multiple different RF electrode combinations, RF electrode moving methods, and phase shifting methods, as described herein.

Similarly, all possible different combinations, permutations and sub-combinations of the device and/or system configurations described in the present application may be used in implementations, embodiments and operation of the devices and systems of the present application, including but not limited to, any possible combinations, sub-combinations and permutations of RF electrode structure, RF electrode geometrical arrangement, RF electrode group configuration, RF energy generating unit(s) structure, the number of RF energy generating units per device, RF energy generating unit(s) operating frequency and/or operating frequency band characteristics, frequencies, the inclusion of Multiplexing/switching unit(s), the use of stationary and/or perpendicularly movable RF electrodes and/or laterally movable RF electrodes as well as any combinations thereof, the structure, number and configuration of phase shifting unit(s), the type, number and configuration of the various sensor units for sensing the temperature of the skin and/or the temperature of one or more RF electrodes as described herein, the type, structure, number and configuration of (optional) velocity determining sensor units for controlling the application of RF energy depending on the velocity of device movement relative to the skin, the type, structure, number and configuration of sensing units for sensing the presence or absence of contact of RF electrode with the skin, and type, number, structure and configuration of the user interface(s) included in the device and/or system.

Thus, any of the embodiments of the devices and/or systems disclosed herein may include but are not limited to, devices having multiple fixed (stationary) RF electrodes configured for using electrode pair switching methods and/or electrode group switching methods, as disclosed in detail hereinabove, devices having perpendicularly movable RF electrodes configured for using electrode pair switching methods and/or electrode group switching methods, as disclosed in detail hereinabove, devices having one or more laterally movable RF electrodes configured for using electrode pair switching methods and/or electrode group switching methods, as disclosed in detail hereinabove, devices having one or more perpendicularly and laterally movable and RF electrodes configured for using electrode pair switching methods and/or electrode group switching methods, as disclosed in detail hereinabove, devices having one or more laterally movable RF electrodes that are not configured for performing electrode pair switching and/or electrode group switching, as disclosed in detail hereinabove.

Furthermore, any of the embodiments of the devices and/or systems disclosed herein may be configured as a system having a main unit attached to applicator unit (as disclosed hereinabove and illustrated in FIG. 3), or as an independent hand held embodiment with an internal power source, as disclosed hereinabove and illustrated in FIG. 4.

Further yet, any of the embodiments of the devices and/or systems disclosed herein may have integrated, non-removable RF electrodes, or may include an attacheable/detacheable and/or removable and/or replaceable and/or disposable RF electrode assembly and/or RF electrode assemblies (such as, but not limited to, any of the different RF electrode assemblies 46, 56 and 76 disclosed hereinabove and illustrated in FIG. 4).

Furthermore, any of the devices and/or systems disclosed herein may (optionally) include any combination and type of sensor(s) for sensing skin temperature and/or the temperature of one or more RF electrodes, and/or velocity sensor(s) for determining the rate of movement of the RF applicator relative to the skin, and/or for sensing contact of one or more of the RF electrodes with the skin. Such sensor(s) may be configured for implementing any of the safety measures operable to control and/or terminate the application of RF energy to the skin and/or to decrease and/or prevent sparking as disclosed in detail hereinabove.

Furthermore, any of the devices and/or systems disclosed herein may (optionally) include any combination and type of indicator devices (including, but not limited to, analog and/or digital temperature displays, LED based or other visible light source based indicator devices known in the art, and or speakers or other audible signal emitting devices as disclosed hereinabove and as known in the art) for providing visible and/or audible and/or other indications of the operational status of the device and/or of electrode or skin temperatures to the user or operator of the device and/or system.

Finally, any of the devices and/or systems disclosed herein may (optionally) include any combination and type and number of user interface devices (such as, but not limited to control buttons, dials, sliders, switches, keyboards, pointing devices and the like) for controlling the operation of the system and/or device and for providing input and/or receiving output from the device or system. Such input and/or output may include but are not limited to, user commands, and/or programming signals, and/or data and/or system status and operating parameters, and the like.

It will be appreciated by those skilled in the art that many types of safety features and output devices may be implemented in the skin treating systems and devices of the present application.

For example, in accordance with one embodiment of the devices and systems disclosed herein the system or device may include a temperature indicator. Such temperature indicator may be implemented as a suitable display unit for displaying the temperature of the skin or the temperature of one or more of the RF electrodes (as determined by measurement of any of the temperature sensors disclosed hereinabove).

For example, the display unit 29 of the main unit 32 of the system 30 (of FIG. 3) is an analog display which may provide an indication of the temperature of the skin and/or of one or more of the RF electrodes 38 by using suitable temperature sensors (such as but not limited to, any temperature sensors included in the sensor unit(s) 2 of FIGS. 1-2, the temperature sensors 225A-225C of FIGS. 12A-12B and FIG. 13 and any temperature sensor included in the Sensor unit(s) 282 of FIGS. 14-16).

Furthermore, any type of display unit or indicator may be used instead of the analog display unit 29 of FIG. 3. Such display units may include but are not limited to, digital display units, LCD display units, LED based unit, OLED based display units, alphanumeric display unit, a graphic symbol display unit, or any other type of display unit or visual indicator device known in the art. Such display units may also be included in any of the hand held units or applicators and/or RF electrode assemblies disclosed in the present application, instead of, or in addition to the display unit 29 of the main unit 32 of the system 30.

The inclusion of such display unit in the devices and systems disclosed herein is useful for providing a temperature indication to the user (such as, for example, a cosmetician or physician treating the patient) by constantly providing the user a visible indication that the temperature range which is both safe and efficient for the desired treatment is indeed being maintained.

Any desired combinations of visual display units may be used in the devices and systems disclosed in the present application. For example any of the hand held units or applicators disclosed hereinabove may include a combination of an alphanumeric display unit (not shown) for indicating the actual temperature of one or more of the RF electrodes and/or the temperature of one or more skin region, and a warning indicator unit (such as but not limited to a LED based warning indicator light). In such an exemplary non-limiting example, during skin treatment the user may monitor the actual skin temperature and/or RF electrode(s) temperature on the alphanumeric display (preferably but not obligatorily disposed on the hand held applicator or RF electrode assembly).

If the measured temperature is within the safe range (which may be factory pre-programmed or set by the user), a green LED in the warning indicator unit is activated enabling the user to quickly ensure proper and safe operation of the device without having to actually read the temperature value in the alphanumeric display unit. If the temperature of the skin and/or of an RF electrode exceeds the safe temperature, the green LED is switched off and a red LED in the warning indicator unit is activated, indicating to the user that the safe temperature value has been exceeded so that the user may terminate treatment and allow the skin and/or RF electrode(s) to cool down to a safe temperature.

It is noted that in addition to or instead off such visual display units and warning indicator lights, the devices and systems of the present application may be configured such that the controller unit included in the device or system (such as, but not limited to the controller units 8, 13 disclosed hereinabove) may process the signals received from the temperature sensor(s) included in the device and automatically terminate the application of RF energy to the skin through any or all of the RF electrodes when the skin temperature and/or RF electrode temperature exceed a threshold value. The threshold value may be fixed, or factory preset or pre-programmed or may be user programmable as is known in the art.

Additionally or alternatively, if the device or system is configured to operate in multiple modes (such as but not limited to the cellulite reduction mode and the skin tightening mode as described in detail hereinabove with respect to the devices 280 and 320 of FIGS. 14 and 16, respectively), it may be possible that different modes of operation will have efficient skin temperature ranges. Thus, it may be possible to add an additional LED to the warning indicator unit which will indicate that the skin temperature is not below the efficient temperature required for the current operating mode of the device.

For example, the controller of the device may use two or more pre-programmed (or user programmable) lowest efficient temperature threshold values, each lower value being used in conjunction with a specific mode of operating the device. For example, if the third LED is an orange LED, the controller unit of the device will switch on the green LED and the orange LED if the temperature is below the skin temperature safety threshold and above the lowest efficient temperature threshold for any operational mode of the device.

It is noted that indicating means different than visual means may be used instead of or in addition to the visual indicators such as the temperature display unit and the warning light indicators described hereinabove, for example a sound signal such as, but not limited to a beep or ring-tone or any other type of audible alarm signal as is known in the art may be used to indicate to the user that the temperature safety threshold has been exceeded. Thus, additional embodiments of the devices and systems of the present application may include a proper audible alarm unit (such as but not limited to the speaker unit 28 of FIG. 3), in addition to or instead of any visual display units as described herein.

The present application also provides an electrode assembly for an RF applicator unit of the systems and devices disclosed herein. The RF electrode assembly may be any of the electrode assemblies 46, 56 and 76 (of FIG. 4) or the electrode assemblies 100 and 120 (of FIGS. 5 and 6, respectively) or the electrode assembly 256 (of FIG. 13) as described in detail hereinabove. In an exemplary embodiment of the RF electrode assembly, the RF electrode assembly includes a housing (such as, for example, the housing 58 of electrode assembly 56 or any other Electrode assembly housing disclosed hereinabove and illustrated in the drawings), two or more RF electrodes (such as, but not limited to the RF electrodes 48 of Electrode assembly 46, and/or the movable RF electrodes 68A-68B of RF electrode assembly 56 and/or the perpendicularly movable RF electrodes of RF electrodes 108A-108E of RF electrode assemblies 100 and 120, or any other electrode types and combinations of the various electrode types of any of the RF electrode assemblies disclosed herein and illustrated in the drawings) and at lease two electrical connecting members, electrically connected to the RF electrodes. The RF electrodes may be disposed in or mounted in or attached to the housing of the RF electrode assembly in any of the different ways disclosed hereinabove and illustrated in the drawings, depending, inter alia, on the number, type and (optional) electrode moving mechanism(s) implemented.

The RF electrode assembly may (optionally) include any number and type of sensors and/or switching mechanisms disclosed herein such as, but not limited to, temperature sensor(s) for sensing the temperature of the skin or of an electrode, electrode contact sensors for detecting electrode contact with the skin (such as, but not limited to, micro-switch based sensors as described herein or any other type of sensor capable of detecting contact of the RF electrodes with the skin, including impedance sensing based electrical sensors and the like, as is known in the art), velocity sensors for sensing and/or determining the velocity of the RF electrode assembly relative to the skin or any other type of usable sensor disclosed herein.

It is noted that while typically (but not obligatorily) most or all of the electrical and/or electronic components of the devices and/or systems described herein such as, for example, the power source, the RF energy generating unit(s), the controller unit(s), the multiplexing/switching unit(s), the user interface, and other components are included in the main unit of the system (such as, for example, the main unit 32 of FIG. 3) or in the applicator unit or hand held unit or hand held device (such as, but not limited to, the applicator unit 6 of FIG. 2, and the hand held unit 36 of FIG. 3 and the device 40 of FIG. 4), this is by no means obligatory.

Thus, the housing of the RF electrode assembly may also include any combination of components selected from, the power source(s), the RF energy generating unit(s), the controller unit(s), the multiplexing/switching unit(s), and the user interface(s) of the skin treatment device and/or system. This may typically (but not obligatorily) apply to devices in which the RF electrode assembly is non-detachably attached to the device or applicator or hand-held unit. However, any of the above additional components and/or any combinations thereof may also be included in detachable embodiments and/or disposable embodiments of the RF electrode assembly. The decision whether to include any of the above additional components in the RF electrode assembly or in other parts of the system and/or device may depend, inter alia, on engineering considerations, component size and cost, component MTBF, the expected useable life of the RF electrode assembly, the size and shape of the RF electrode assembly, and other design, manufacturing and economical considerations.

The RF electrode assemblies of the devices and systems may include fixed (non-detachable) electrode assemblies, detachable (and attachable) electrode assemblies, multiple use electrode assemblies, single-use electrode assemblies and disposable electrode assemblies (for multiple uses or for single use). Such assemblies may be sold and/or distributed separately from the entire device or system or in addition thereto.

It is further noted that a single type of device or hand-held unit or applicator may be designed to accept and be operable with any number of different types of RF electrode assemblies. Thus, for example, any of the RF electrode assemblies 46, 56, 76 and 256 may be interchangeably attached to and operated by the device 40 of FIG. 4.

The present application also provides a kit including a device or systems selected from the devices and systems disclosed herein and one or more RF electrode assembly selected from any of the different types of RF electrode assemblies disclosed hereinabove. This type of kit may allow a user to use different types of RF electrode assemblies for skin treatment, improving the flexibility of the system and the available treatment modes and treatment types.

It is noted that when movable RF electrodes are used in an embodiment of the devices and systems disclosed herein, the moving of any of the movable RF electrodes may be performed at any desired time during the operation of the device, including but not limited to moving any of the movable electrode(s), before, during or after any time period of applying RF energy to the skin through any electrode group containing such movable RF electrode(s).

Thus, in accordance with an embodiment of the device or system each and any of the movable electrodes may be moved continuously and/or intermittently during any time of operation of the device, and/or any time period of application of RF energy to the skin through any of the RF electrodes or electrodes groups as disclosed in detail hereinabove.

Furthermore, any suitable sequence of moving of any of the movable electrodes may be implemented and used in operating the devices of the present application. And any combination of different velocity of electrode movement(s) and of sequence of electrode movements (during intermittent movements of electrode(s) may be implemented by suitable control of movement parameters of any of the electrode moving units disclosed herein by the controller unit(s) included in the device or system (such as, but not limited to the Controller unit(s) 13 of FIG. 14).

It is further noted that while all the embodiments and examples disclosed hereinabove are adapted for use with electromagnetic radiation energy in the RF range, the methods, devices and systems of the present application is not limited to the use of RF electromagnetic energy, and the RF electrodes may be substituted with electrodes suitable for use in delivering energy to the skin in other frequency ranges different than the RF frequency range. Thus, the devices systems, methods and electrodes disclosed in the present application may be adapted to use with other electromagnetic radiation in other frequency ranges such as but not limited to electromagnetic energy in the microwave frequency range, and the like. For example, in such cases, the RF energy generating unit 4 of the device 10 of FIG. 1 and the device 20 of FIG. 2 may be replaced with another suitable type of electromagnetic energy generating unit in the microwave frequency range. Thus, while RF electromagnetic radiation is a practical frequency range for use in the devices and systems disclosed hereinabove, this frequency range is not obligatory and other electromagnetic radiation frequencies ranges may be used in other embodiments of the devices systems and methods of the present application depending, inter alia, on the particular application being implemented and on cost, device size, engineering considerations and safety considerations.

What is claimed is:

1. A device for treatment of skin tissues, the device comprising:
    at least one RF electromagnetic energy generating unit;
    a plurality of non-invasive electrodes electrically connectable to said at least one RF electromagnetic energy generating unit for applying RF electromagnetic energy to the skin; and
    at least one controller unit operatively connected to said at least one RF electromagnetic energy generating unit for controlling the application of electromagnetic energy by said at least one RF electromagnetic energy generating unit to at least one group of electrodes controllably selected from said plurality of electrodes and for controllably changing the selected group of electrodes during the operation of said device,
    wherein the depth of penetration of said RF electromagnetic energy into said tissues is controlled by controlling the distance between electrodes in said group of electrodes to which said RF electromagnetic energy is applied,
    and wherein at least one electrode of said plurality of electrodes is a spring mounted electrode movable within a corresponding opening and associated with a respective switching element, and wherein when said spring mounted electrode is moved within the corresponding opening in a contracting direction against the biasing force of the spring, its associated switching element is closed to energize the electrode, and when said spring mounted electrode is moved within the opening by the biasing force of the contracted spring in an extending direction to more than a certain extent, its associated switching element is opened to terminate the energizing of the electrode.

2. The device according to claim 1 further comprising a power source for energizing said at least one RF electromagnetic energy generating unit and said at least one controller unit.

3. The device according to claim 1 wherein said at least one group of electrodes is selected from, a pair of electrodes in a bipolar configuration, three electrodes in a tripolar configuration and more than three electrodes in a multipolar configuration.

4. The device according to claim 1 wherein said at least one RF energy generating unit is adapted to operate at any frequency or frequency band in the range of 0.35 MHz-250 MHz.

5. The device according to claim 1 further comprising at least one sensor.

6. The device according to claim 5 wherein said at least one sensor is connected to said at least one controller unit for providing output signals to said controller unit.

7. The device according to claim 5 wherein said at least one sensor is selected from one or more skin temperature sensors, one or more electrode temperature sensors, one or more velocity sensors, one or more electrode contact sensors, and any combinations thereof.

8. The device according to claim 5 wherein said at least one sensor is selected from a sensor for sensing at least one physical parameter of at least one electrode of said plurality of electrodes, a sensor for sensing the velocity of said device relative to said skin and a sensor for sensing at least one physical parameter of the skin.

9. The device according to claim 8 wherein said at least one physical parameter of the skin is temperature of at least one region of said skin.

10. The device according to claim 8 wherein said at least one physical parameter of said at least one electrode is selected from the temperature of at least one region of said electrode and the presence or absence of contact between said electrode and said skin.

11. The device according to claim 8 wherein said at least one controller is configured for processing signals received by said at least one sensor to obtain processed data and for performing based on said data one or more actions selected from,
    terminating the application of RF electromagnetic energy to the skin through one or more groups of said electrodes,
    initiating the application of RF electromagnetic energy to the skin through one or more groups of said electrodes,
    terminating the application of RF electromagnetic energy to the skin through at least a first group of said electrodes and initiating the application of RF electromagnetic energy to the skin through at least a second group of electrodes different than said first group of electrodes, and
    terminating the application of RF electromagnetic energy to the skin through all currently energized electrodes of said device.

12. The device according to claim 1 further comprising a housing for housing one or more components selected from said plurality of electrodes, said at least one controller unit, a power source, said at least one RF electromagnetic energy generating unit, one or more sensor units and any combinations thereof.

13. The device according to claim 1 wherein said device comprises an applicator unit configured to be applied to the skin, said applicator unit comprises a housing for housing one or more components selected from said plurality of electrodes, said at least one controller unit, a power source, said at least one RF electromagnetic energy generating unit, one or more sensor units and any combinations thereof.

14. The device according to claim 13 wherein said device includes an RF electrode assembly comprising a housing and at least said plurality of RF electrodes attached to said housing.

15. The device according to claim 13 wherein said one or more sensors are attached to said RF electrode assembly.

16. The device according to claim 15 wherein said RF electrode assembly is selected from a fixed RF electrode assembly and a detachable RF electrode assembly detachably attachable to said device.

17. The device according to claim 15 wherein said RF electrode assembly is a detachable RF electrode assembly detachably attachable to said device, and wherein said housing of said RF electrode assembly also includes electrical contacts for electrically connecting said RF electrodes to said at least one RF energy generating unit.

18. The device according to claim 17 wherein said electrical contacts are also shaped to mechanically attach said RF electrode assembly to said device.

19. The device according to claim 15 wherein said RF electrode assembly is selected from a re-useable RF electrode assembly and a disposable RF electrode assembly.

20. The device according to claim 1 wherein said at least one controller unit is configured to control the application of said RF electromagnetic energy to the skin through different groups of electrodes of said plurality of electrodes at different times during the application of said RF electromagnetic energy to said skin.

21. The device according to claim 1 wherein at least one electrode of said plurality of electrodes is a movable electrode.

22. The device according to claim 21 wherein said movable electrode is selected from an electrode movable in a direction generally perpendicular to the surface of the skin, an electrode laterally movable along the surface of the skin and an electrode movable in directions generally perpendicular to and generally lateral along the surface of the skin.

23. The device according to claim 21 wherein said device further includes at least one electrode moving unit coupled to said at least one electrode for moving said at least one electrode relative to at least one other electrode of said plurality of electrodes.

24. The device according to claim 23 wherein said electrode moving unit comprises a an electrode moving mechanism selected from a motor, a linear motor, a non-linear motor, a gear coupled motor, an electromechanical moving mechanism, an electromagnetic moving mechanism and a solenoid actuated moving mechanism.

25. The device according to claim 23 wherein said at least one controller unit is configured to controllably activate said electrode moving unit to change the distance between said at least one electrode coupled to said electrode moving mechanism and at least one other electrode of said plurality of electrodes.

26. The device according to claim 1 wherein said at least one RF energy generating unit comprises a single RF generating unit operable at or about a single RF frequency or a single RF frequency band.

27. The device according to claim 26 wherein said device also includes a phase shifting unit connected to at least one RF electrode and to said RF energy generating unit for shifting the phase of the RF electromagnetic waves applied to the skin through said at least a first RF electrode relative to the phase of an RF electromagnetic wave applied to the skin through at least a second RF electrode different than said first RF electrode.

28. The device according to claim 1 wherein said at least one RF energy generating unit comprises a plurality of RF energy generating units, each RF generating unit is operable at or about a single RF frequency or a single RF frequency band, wherein the RF frequencies or the RF frequency of at least some of said plurality of RF energy generating units are different.

29. The device according to claim 28 wherein said device also includes at least one phase shifting unit connected to at least one RF electrode and to one or more RF energy generating units of said plurality of RF energy generating units for shifting the phase of the RF electromagnetic waves applied to the skin through said at least a first RF electrode relative to the phase of an RF electromagnetic wave applied to the skin through at least a second RF electrode different than said first RF electrode.

30. The device according to claim 28 also including a multiplexing switching unit connected to said plurality of RF energy generating units, said plurality of electrodes and said at least one controller unit for controllably applying RF energy from any combination of RF energy generating units selected from said plurality of RF energy generating units to any electrode or electrode combination selected from said plurality of electrodes.

31. The device according to claim 30 wherein said multiplexing switching unit comprises one or more phase shifting units.

32. The device according to claim 28 wherein said device is configured for being controllably operable in a plurality of different operating modes and wherein in each different operating mode the RF frequency or RF frequencies applied to the skin are different than the RF frequency or RF frequencies applied to the skin in other operating modes.

33. The device according to claim 28 wherein the RF frequency or frequencies used in at least some operating mode of said plurality of operating modes are selected to preferentially heat selected different types of skin tissues.

34. The device according to claim 33 wherein said different types of skin tissues are selected from, fatty skin tissue, hypodermal adipose tissue, rete pegs, non-fatty dermal tissue, epidermal tissue and combinations thereof.

35. The device according to claim 28 wherein the device is configured for simultaneously applying combinations of different RF frequencies or different RF frequency bands through any suitable electrodes for simultaneously heating combinations of different type of skin tissues.

36. The device according to claim 28 wherein the RF frequency or RF frequencies applied to the skin in a first operating mode are in the range of 0.35-1.5 MHz and the RF frequency or RF frequencies applied to the skin in a second operating mode are in the range of 4-15 MHz.

37. The device according to claim 28 wherein the RF frequency or RF frequencies applied to the skin in a first operating mode are in the range of 0.35-1.5 MHz, the RF frequency or RF frequencies applied to the skin in a second operating mode are in the range of 4-15 MHz, and the RF frequencies applied to the skin in a third operating mode include frequencies in the range of 0.35-1.5 MHz and in the range of 4-15 MHz.

38. An RF electrode assembly for use in a skin treating device, said RF electrode assembly comprising:
   a housing; and
   a plurality of non-invasive RF electrodes for applying RF electromagnetic energy to the skin from at least one group of electrodes controllably selected from said plurality of electrodes, the RF electrodes attached to said housing and connectable to an RF electromagnetic energy generating unit of said device, wherein the depth of penetration of said RF electromagnetic energy into said tissues is controlled by controlling the distance between electrodes in said group of electrodes to which said RF electromagnetic energy is applied, and wherein at least one electrode of said plurality of electrodes is a spring mounted electrode movable within a corresponding opening and associated with a respective switching element, and wherein when said spring mounted electrode is moved within the corresponding opening in a contracting direction against the biasing force of the spring, its associated switching element is closed to energize the electrode, and when said spring mounted electrode is moved within the opening by the biasing force of the contracted spring in an extending direction to more than a certain extent, its associated switching element is opened to terminate the energizing of the electrode.

39. A kit including the device according to claim 1 and one or more attachable RF electrode assemblies each including a plurality of electrodes, said one or more RF electrode assemblies are detachably attachable to said device.

* * * * *